(12) United States Patent
Martin et al.

(10) Patent No.: US 7,381,713 B2
(45) Date of Patent: Jun. 3, 2008

(54) TREATMENT OF CANCER BY REDUCTION OF INTRACELLULAR ENERGY AND PYRIMIDINES

(75) Inventors: Daniel S. Martin, Pound Ridge, NY (US); Joseph R. Bertino, Branford, CT (US); Jason Koutcher, New Rochelle, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 10/172,346

(22) Filed: Jun. 13, 2002

(65) Prior Publication Data

US 2003/0139331 A1 Jul. 24, 2003

(51) Int. Cl.
A61K 31/70 (2006.01)
A61K 31/66 (2006.01)
A61K 31/505 (2006.01)
A61K 31/21 (2006.01)
A61K 31/26 (2006.01)

(52) U.S. Cl. .................. 514/45; 514/75; 514/269; 514/561

(58) Field of Classification Search .......... 514/45, 514/269, 75, 561; 536/27.21; 546/310, 546/348; 562/11, 571, 8, 533; 564/112–3, 564/47; 568/926

See application file for complete search history.

(56) References Cited

U.S. PATENT DOCUMENTS 5,641,670 A 6/1997 Treco et al.
2003/0139331 A1* 7/2003 Martin et al. ............... 514/12

FOREIGN PATENT DOCUMENTS

WO  W O 93/23014 A1 * 11/1993
WO  WO 02/45720 A1    6/2002
WO  PCT/US03/18716    6/2003
WO  WO 93/23014 A1   11/2003
WO  WO 03/105862 A1  12/2003

OTHER PUBLICATIONS

Stolfi et al., "Biochemical Modulation of Tumor Cell Energy: Regression of Advanced Spontaneous Murine Breast Tumors with a 5-Fluorouracil-containing Drug Combination," *Cancer Research*, 52(15), 4074-4081 (Aug. 1, 1992).*
Colofiore et al., "Biochemical Modulation of Tumor Cell Energy IV. Evidence for the Contribution of Adenosine Triphosphate (ATP) Depletion to Chemotherapeutically Induced Tumor Regression," *Biochemical Pharmacology*, 50(11), 1943-1948 (Nov. 27, 1995).*
Martin et al. (III), "Marked Enhancement in vivo of Paclitaxel's (Taxol's) Tumor-Regressing Activity by ATP-Depleting Modulation," *Anti-Cancer Drugs*, 7, 655-659 (1996).*
Koutcher et al., "Radiation Enhancement by Biochemical Modulation and 5-Fluorouracil," *Intl. J. Radiation Oncology Biology Physics*, 39(5), 1145-1152 (Dec. 1, 1997).*

(V) Kamatani et al., "Selective Killing of Human Malignant Cell Lines Deficient in Methylthioadenosine Phosphorylase, a Purine Metabolic Enzyme," Proc. National Acad. Sciences USA, 78(2), 1219-1223 (Feb., 1981); copy supplied by, but not cited by applicant.*
Herceg Z. & Z. -Q. Wang. Failure of poly (ADP-ribose) polymerase cleavage by caspases leads to induction of necrosis and enhanced apoptosis. Mol. Cell Biol. 19:5124-5133 (1999) [Exhibit 1].
Hirsch, T. et al. The apoptosis-necrosis paradox. Apoptogenic proteases activated after mitochondrial permeability transition determine the mode of cell death. Oncogene 15:1573-1581 (1997) [Exhibit 2].
Geschwind, J.-F. H., et al. Novel therapy for liver cancer: direct intraarterial injection of a potent inhibitor of ATP production. Canc. Res. 62:3909-3913 (2002) [Exhibit 3].
Green, D.R. & Reed, J.C. Mitochondria & apoptosis. Science 281:1309-1312 (1998) [Exhibit 4].
Leist, M. et al. Intracellular adenosine triphosphate (ATP) concentration: a switch in the decision between apoptosis and necrosis. J. Exp. Med. 185:1481-1486 (1997) [Exhibit 5].
Lemaire, et. al. Inhibition of caspase activity induces a switch from apoptosis to necrosis. FEBS Lett. 425:266-270 (1998) [Exhibit 6].
Martin, D.S., et al. ATP depletion + pyrimidine depletion can markedly enhance cancer therapy: fresh insight for a new approach. Canc. Res. 60:6776-6783 (2000) [Exhibit 7].
Mehmet, H., et al. Relation of impaired energy metabolism to apoptosis and necrosis following transient cerebral hypoxia-ischaemia. Cell Death Differ. 5:321-329 (1998) [Exhibit 8].
Nicotera, P. & Leist, M. Energy supply and the shape of death in neurons and lymphoid cells. Cell Death Differ. 4:435-442 (1997) [Exhibit 9].
Nieminen, A.-L., et al. ATP depletion rather than mitochondrial depolarization mediates hepatocyte killing after metabolic inhibition. J. Am. Phys. 267:C67-C74 (1994) [Exhibit 10].
Nord, L.D., et al. Apoptosis induced in advanced CD8F1-murine mammary tumors by the combination of PALA, MMPR and 6AN precedes tumor regression and is preceded by ATP depletion. Canc. Chemo. Pharm. 40:376-384 (1997) [Exhibit 11].
Sane, A.-T. & Bertrand, R. Caspase inhibition in camptothecin-treated U-937 cells is coupled with a shift from apoptosis to transient G1 arrest followed by necrotic cell death. Canc. Res. 59:3565-3569 (1999) [Exhibit 12].
Sweet, S. & Singh, G. Accumulation of human promyelocytic leukemic (HL-60) cells at two energetic cell cycle checkpoints. Canc. Res. 55:5164-5167 (1995) [Exhibit 13].

(Continued)

Primary Examiner—L. E. Crane
(74) Attorney, Agent, or Firm—Law Offices of Albert Wai-Kit Chan, PLLC

(57) ABSTRACT

This invention provides a method for treating a cancer subject comprising administering to the subject a combination of ATP-depleting agents at concentrations which deplete the ATP level to at least 15% of normal in cancer cells, a pyrimidine antagonist, and an anticancer agent to which the treated cancer is sensitive. This invention also provides a composition comprising a combination of ATP-depleting agents at concentrations which deplete the ATP level to at least 15% of normal in cancer cells, a pyrimidine antagonist, and an anticancer agent to which the treated cancer is sensitive. Finally this invention provides a pharmaceutical composition comprising the above composition or a combination thereof and a pharmaceutically acceptable carrier.

8 Claims, 3 Drawing Sheets

OTHER PUBLICATIONS

Figure 1:
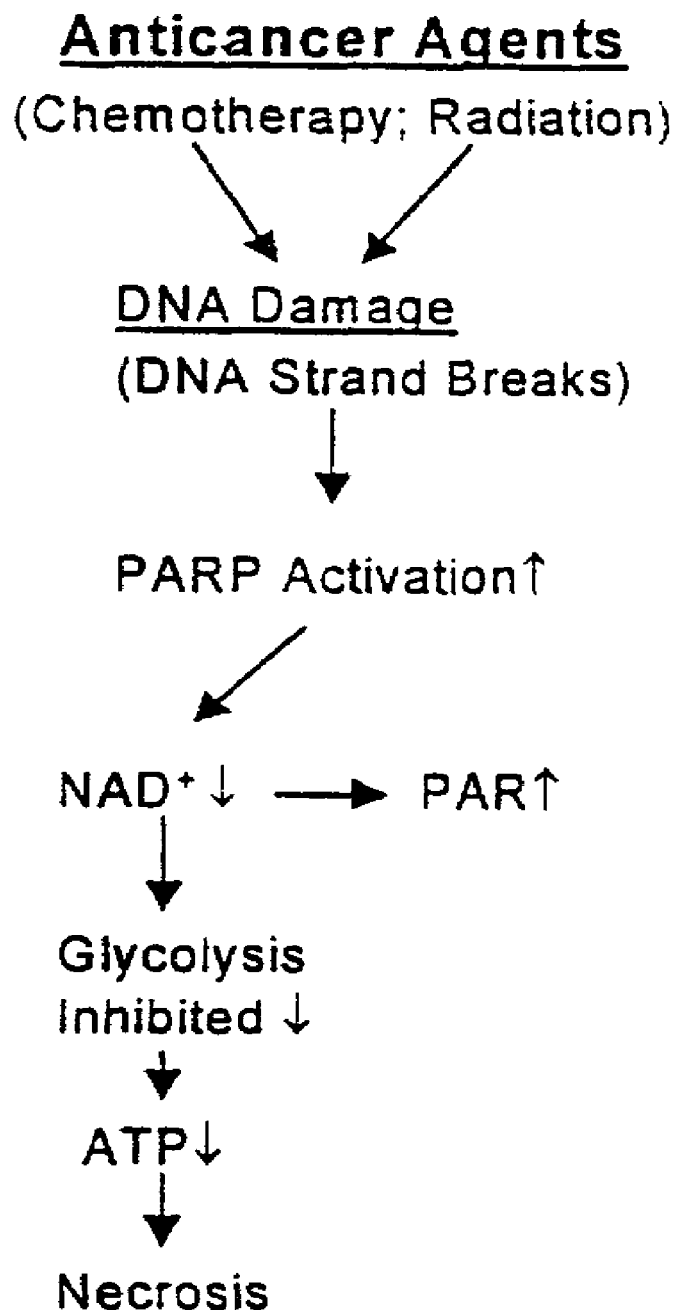

Tsujimoto, Y. Apoptosis and necrosis: intracellular ATP level as a determinant for cell death modes. Cell Death Differ. 4:429-434 (1997) [Exhibit 14].

PCT International Search Report for Sloan-Kettering Institute for Cancer Research, et al., Int'l App'l No. PCT/US01/46886, Filed on Dec. 4, 2001, Dated May 22, 2002.

PCT Written Opinion for Sloan-Kettering Institute for Cancer Research, et al., Int'l App'l No. PCT/US01/46886, Filed on Dec. 4, 2001, Dated Apr. 17, 2003.

PCT International Preliminary Examination Report for Sloan-Kettering Institute for Cancer Research, et al., Int'l App'l No. PCT/US01/46886, Filed on Dec. 4, 2001, Dated Sep. 6, 2003.

Hageboutros, A., Judes, G.R., Brennan, J., Green, F., Joffman, J., LaCreta, F.P., Colofiore, J., Martin, D.S., Ozols, R.F., O'Dwyer P.J., Phase I trail of fluorouracil modulation by N-phosphonacetyl-L-aspartate and 6-methylmercaptopurine ribonucleoside. Cancer Chemother. Pharmacol.; 1996, 37(3):229-234.

Kelsen, D., Martin, D.S., Colofiore, J., Sawyer, R., Coit, D., A phase II trial of biochemical modulation using N-phosphonacetyl-L-aspartate, high-dose methotrexate, high-dose 5-fluorouracil, and leucovorin in patients with adenocarcinoma of unknown primary site. Cancer; 1992, 70(7): 1988-1992. (Oct. 1, 1992).

Kemeny, N., Schneider, A., Martin D.S., Colofiore J, Sawyer, R.C., Derby, S., Salvia, B., Phase I trial of N-phosphonacetyl-L-aspartate, methotrexate, and 5-fluorouracil with leucovorin rescue in patients with advanced cancer. Cancer Res.; 1989, 49(16): 4636-4639. (Aug. 15, 1989).

Kemeny, N.E., Schneider, A., Martin, D.S., Phase I trial of PALA, methotrexate, fluorouracil, leucovorin, and uridine rescue in patients with advanced cancer. The use of uridine to decrease fluorouracil toxicity. Cancer Invest.; 1990, 8(2):263-264.

Koutcher, J.A., Alfieri, A.A., Matie, C., Meyer, K.L., Street, J.C., Martin, D.S., Effect of 6-aminonicotinamide on the pentose phosphate pathway: 31P NMR and tumor growth delay studies. Magn. Reson. Med., 1996, 36(6):887-892.

Koutcher, J.A., Alfieri, A.A., Tsai, J.C., Matei, C., Stolfi, R.L., Ballon, D., Martin, D.S., Evaluation of chemotherapy and radiation enhancement and 31P NMR spectral changes induced by biochemical modulation. Cancer Invest., 1997, 15(2)111-120.

Mahmood, U., Street, J.C., Matei, C., Ballon, D., Martin, D.S., Koutcher J.A., In vivo detection by 31P NMR of pentose phosphate pathway block secondary to biochemical modulation. NMR Biomed.; 1996, 9(3):114-120.

Martin D.S., Kemeny NE. 1992. Modulation of fluorouracil by N-phosphonacetyl-L-aspartate: a review. Semin. Oncol.; 19(2 Suppl 3):49-55. (Mar. 1992).

Martin, D.S., Kemeny, N.E., Overview of N-phosphonacetyl-L-aspartate + fluorouracil in clinical trials. Semin. Oncol.; 1992, 19(2 Suppl 3):228-233. (Mar. 1992).

Martin, D.S, Stolfi, R.L., Colofiore, J.R., Nord, L.D., Sternberg, S., Biochemical modulation of tumor cell energy in vivo: II. A lower dose of Adriamycin is required and a greater antitumor activity is induced when cellular energy is depressed. Cancer. Invest.; 1994, 12(3):296-307.

Martin, D.S., Schwartz, G.K., Chemotherapeutically induced DNA damage, ATP depletion, and the apoptotic biochemical cascade. Oncol. Res.; 1997, 9(1):1-5.

Martin, D.S., Spriggs, D., Koutcher, J.A., A concomitant ATP-depleting strategy markedly enhances anticancer agent activity. Apoptosis; 2001, 6(1-2):125-131.

Martin, D.S. Purine and pyrimidine biochemistry, and some relevant clinical and preclinical cancer chemotherapy research In: G. Powis and R.A. Prough (eds), Metabolism and Action of Anti-Cancer Drugs,91-140. London, Taylor and Francis, 1987.

Martin, D.S., Stolfi, R.L., Sawyer, R.C., Spiegelman, S. Casper, E.S. and Young, C.W. Therapeutic utility of utilizing low doses of N-{phosphonacetyl)L-aspartic acid in combination with 5-fluoroucil; a murine study with clinical relevance. Cancer Res. 43:2317-2321, (May 1983).

Martin, D.S., Alfieri, A., Koutcher, J.A., et al., Selective-killing of drug-resistant mammary carcinomas by exploiting the tumor cell ATP-viability threshold. Proc. AACR 45:570 (Abstract 2462), 2004.

Martin, D.S., Stolfi, R.L., Colofiore, J.C., Koutcher, J.A., Alfieri, A., Sternberg, S., and Nord, L.D. Apoptosis resulting from anti-cancer agent activity in vivo is enhanced by biochemical modulation of tumor cell energy. In: M. Lavin and D. Walters (eds.) Programmed Cell Death. The Cellular and Molecular Biology of Apoptosis 279-296, New York: Harwood Academic 1993.

Martin, D.S., Stolfi, R.L., Nord, L.D. and Colofiore, J.R. Enhancement of chemotherapeutically-induced apoptosis in vivo by biochemical modulation of poly-(ADP-ribose) polymerase. Oncol. Rep. 3:317-322, 1996.

Martin, D.S Cancer chemotherapy: past is prologue. Mt. Sinai. J. Med. 52:426-434, 1985. (Jun. 1985; Issue No. 6).

Martin, D.S., Bertino, J.R., and Koutcher, J.A. ATP depletion. + pyrimidine depletion can markedly enhance cancer therapy. Fresh insight for a new approach. Cancer Res. 60:6776-6783, 2000. (Dec. 15, 2000).

Koutcher, J.A., Alfieri, A., Stolfi, R.L., Devitt, M.L., Colofiore, J.R., Nord, L.D., and Martin, D.S. Potentiation of three drug chemotherapy regimen by radiation. Cancer Res. 53:3518-3823, 1993.

Colofiore, J.R., Stolfi, R.L., Nord, L.D., and Martin, D.S. On the relationship of ATP-depletion to chemotherapeutically-induced tumor regression. Int. J. Oncol. 7:1401-1404, 1995.

Nord, L.D. Stolfi, R.L., Colofiore, J.R., Martin, D.S., Correlation of retetniton of tumore methylmercaptopurine riboside-5'-phophate with effectiveness in CD8F1 murine mammary tumor regression. Biochem Pharmacol; 1996, 51(5):621-627.

Nord, L.D., Stolfi, R.L., Alfieri, A.A., Netto, G., Reuter, V., Sternberg, S.S., Colofiore, J.R., Koutcher, J.A., Martin, D.S., Apoptosis induced in advanced CD8F1-murine mammary tumors by the combination of PALA, MMPR and 6AN precedes tumor regression and is preceded by ATP depletion. Cancer Chemother. Pharmacol.; 1997, 40:376-384.

O'Dwyer, P.J., Judes, G.R., Colofiore, J., Walczak, J., Hoffman, J., LaCreta F.P., Comis, R.L., Martin, D.S., Ozols, R.F., Phase I trial of flurorauracil modulation by of N-phosphonacetyl-L-aspartate and 6-methylmercaptopurine riboside: optimization of tumor biopsy specimens. J. Natl. Cancer Inst.; 1991, 83(17):1235-1240.(Sep. 4, 1991).

Stolfi, R.L., Martin, D.S., Enhancement of anticancer activity by selective inhibition of rapidly proliferating tissues of the host. Pharmacol. Ther.; 1991, 49(1-2):43-54.

Stolfi, R.L., Colofiore, J.R., Nord, L.D., Martin, D.S., Enhanced antitumor activity of an Adriamycin + 5-fluorouracil combination when preceded by biochemical modulation. Anticancer Drugs; 1996, 7(1):100-104.

Ko, et al., Advanced cancers: eradication in all cases using 3-bromopyruvate therapy to deplete ATP. Biochemical and Biophysical Research Communications, 2004, 269-275.

Jurkowitz, et al., Adenosine, Inosine, and Guanosine Protect Glial Cells During Glucose Deprivation and Mitochondrial Inhibition: Correlation Between Protection and ATP Preservation. Journal of Neurochemistry, 1998, 71(2):535-548.

Lieberthal, et al., Graded ATP depletion can cause necrosis or apoptosis of cultured mouse proximal tubular cells. American Physiological Society; 1998, F315-F327.

Lu, et al., Cellular ATP Depletion by LY309887 as a Predictor of Growth Inhibition in Human Tumor Cell Lines. Clinical Cancer Research; Jan. 1, 2000, 5:271-277.

Venkatachalam, et al., Energy Thresholds That Determine Membrane Integrity and Injury in a Renal Epithelial Cell Line (LLC-PK1). J. Clin. Invest.; 1988, 81:745-758.

Anundi, et al., Fructose prevents hypoxic cell death in liver. The American Journal of Physiology; Sep. 1987;253(3 Pt 1):G390-G396.

Cannon, et al., The Effects of Fructose on Adenosine Triphosphate Depletion following Mitochondrial Dysfunction and Lethal Cell Injury in Isolated Rat Hepatocytes. Toxicology and Applied Pharmacology; 1991, 108(3):407-416.

Yager, et al., Correlation between Content of High-Energy Phosphates and Hypoxic-Ischemic Damage in Immature and Mature Astrocytes. Elsevier Science Publishers, Amsterdam; 1994, 82(1-2):62-68.

PCT Notification of Transmittal of the International Search Report or the Declaration for Sloan-Kettering Institute for Cancer Research, Int'l App'l No. PCT/US03/18716, Filed on Jun. 13, 2003, Dated Nov. 25, 2003.

Supplementary European Search Report from the European Patent Office for Application No. EP 01 98 6104.6—2123 PCT/US0146886 for Sloan-Kettering Institute for Cancer Research dated Mar. 28, 2007.

PCT International Preliminary Examination Report for Sloan Kettering Institute fro Cancer Research, PCT/US01/46886 (Atty. Dkt. #636-A-PCT), "Treatment of cancer by reduction of intracellular energy and pyrimidines," filed Dec. 4, 2001, Dated Jul. 25, 2003.

Amarante-Mendes, G.P., finucane, D.M., Martin, S.J., Cotter, T.G., Salvesen, G.S. and Green, D.R., 1998, "Anti-apoptotic oncogenes prevent caspase-dependent and independent commitment for cell death," Cell death Differ., 5:298-306.

Batova, A., Diccianni, M.B., Omura, Minamisawa, M., Yu, J., Carrera, C.J., Bridgeman, L.J., kung. F.H., Pullen, J., Amyulong, M.D. and Yu A.L., 1999, use of alanosine as a methyladenosine phosphorylase-selective therapy for T-cell acute lymphoblastic leukemia in vitro, Cancer Res., 59:1492-1497.

Berner, N.A., and Berger, S.J., 1986, "Metabolic consequences of DNA damage: the role of poly (ADP-ribose) polymerase as mediator of the suicide response,"In: L. Grossman, A.C. Upton, (eds.) Mechanisms of DNA Damage and Repair, pp. 357-363. New York; Plenum Publishing Corporation.

Berns, A., May 2002, "Senescence: A companion in chemotherapy?" Cancer Cell, 309-311.

Bertino, J.R., 1990, "Leucovorin rescue revisited: Editorial," J. Clin. Oncol., 8(2):193-195.

Bissett, D., Mcleod, H.L., Sheedy, B., Collier, M., Pithavala, Y., Paradiso, L., Pitsiladas, M. and Cassidy, J., 2001, "Phase 1 doseescalation and pharmacokinetic study of a novel folate analogue A G 2034," Br. J. Cancer, 84:308-312.

Bonfoco, E., Krainc, D., Ankarcrona, M., Nicotera, P. and lipton, S.A. 1995, "Apoptosis and necrosis; two distinct ebents induced, respectively, by mild and intense insults with N-methyl-D-aspartate or metric oxide/superoxide in cortical cell cultures," Proc. Natl. Acad. Sci. USA, 92:7162-7166.

Bose, R., Verheji, M., Haimovitz-Friedman, A. Scotto. K., Kucks, Z. and Kolesnick, R., 1995 "Ceramide synthase mediates daunorubicin-induced apoptosis: an alternative mechanism for generating death signals," Cell, 82:405-411.

Boulares, A.H., Yokovlev, A.G., Ivanova, V., Stoica, B.A., Wang, G., Iyer, S. and Smulson, M., 1999, "Role of poly (ADP-ribose) polymerase (PARP) cleavage in apoptosis. Caspase-3 resistant PARP mutant increases rates of apoptosis in transfected cells," J. Biol. Chem., 274:22932-22940.

Britten, C.D., Rowinsky, E.K., Baker, S.D., Weiss, G.R., Smith, L., Staphenson, J., Rothenberg, M., Smetzer, L., Cramer, J., Collins, W., Von Hoff, D.D., and Eckhardt, S.G., 2000, "A Phase 1 and pharmacokinetic study of the mitochondrial-specific chodacyanine dye analog MKT 011," Clin. Cancer res., 6:42-49.

Bronder, J.L. and Moran, R.G., 2002, "Antifolates targeting purine synthesis allow entry of tumor cells into S phase regardless of p53 function," Cancer res., 62:5236-5241.

Budihardjo, II, Walker, D.L., Svingen, P.A. Buckwalter, C.A. Desnoyers, S., Eckdahl, S., Shah, G.M., Poirier, G.G., reid, J.M., Ames, M.M., and Kaufmann, S.H., 1998. "6-Aminonicotinarride sensitizes human tumor cell lines to cisplatin," Clinical Cancer Research, 4:117-30.

Cahill, D.P., Kinzler, K.W., Vogelstein, B. and Lengauer, C., 1999, "Genetic instability and Darwinian selection tumors," Trends Cell bio., 57-60.

Carson, D.A., Seto, S., Wasson, B., and Carrera, C., 1986, "DNA strand breaks, NAD metabolism, programmed cell death," Exp. Cell. Res., 164:273-281.

Cayman Chemicals, "F16" Product Information sheet, Catalog No. 10022, Product Chemical Name is 4 [(1E)-2-(1H-indol-3-yl)ethenyl]-1-methyl-pyridium iodide, Ann Arbor Michigan, Mar. 16, 2006, one data sheet.

Chalterjee, S., Hirota, H., Belfi, C.A., Berger, S.J. and Berger, N.A., 1997, "Hypersensitivity to DNA cross-linking agents associated with up-regulation of glucose-regulated stress protein GRP 78," Cancer res., 57:5112-5116.

Chen, Z.H., Zhang, H. and Savarese, T.M., 1996, "Gene deletion chemoselectivity: codeletion of the genes for p16INK4, methylthioadenosine phosphorylase, and the _-and_-interferons in human pancreatic cell carcinoma lines and its implications for chemotherapy," Cancer Res., 56:1083-1090.

Constantini, P., Chemyak, B.V., Petronilli, V. and Bernardi, P., 1996, "Modulation of the mitochondrial permeability transition pore by pyridine nucleotides and dithiol oxidation at two separate sites," J. Biol. Chem., 271:6746-6751.

Cory, A.H. and Cory, J.G., 1994, "Use of nucleoside Kinase deficient mouse leukemia L1210 cell lines to determine metabolic routes of activation of antitumor nucleoside analogs," Adv. enzyme regul., 34:1-12.

Cotter, T.G., Lenon, S.V., Glynn, J.G. and Martin, S.J., 1990, "Cell death via apoptosis and its relationship to growth, development and differentiation of both tumor and normal cells," Anticancer res., 10:1153-1160.

Dang, C.V. and Semenza, G.L., 1999, "Oncogenic alterations metabolism," Trends Biochem. Sci., 24:68-92.

Dietrich, L.S., Kaplan, L., and Friedland, I.M., 1958, "Pyridine nucleotide metabolism: mechanism of action of the niacin antagonist, 6-aminonicotinamide," J. Biol. Chem. 233:964-968.

Droin, N., Beauchemin, M., Solary, E. and Bertrand, R., 2000, "Identification of a casepase-2 isoform that behaves as endogenous inhibitor of the casepase cascade," Cancer Res., 60:7039-7047.

Eguchi, Y., Shimizu, S., and Tsujimoto, Y., 1997, "Intracellular ATP levels determine cell fate by apoptosis or necrosis," Cancer Res., 57:1835-1840.

Evtodienko, Y.V., Teplova, V.V., Sidosh, S.S., Ichas, F. and Mazal, J.P., 1996, "Microtubule-active drugs suppress the closure of the permeability transition pore in tumor mitochondria," FEBS Lett., 393-86-88.

Fantin et al., Jul. 2002, "A Novel Mitochondriac Small Molecule [F16] That Effectively Inhibits Tumor Cell Growth," Cancer Cell, 2(1):29-42.

FItchen, J.H., Riscoe, M.K., Dana, B.W., Lawrence, H.J. and Ferro, A.J., 1986, "Methylthioadenosine phosphorylase defiency in human leukemias and solid tumors," Cancer Res., 46:5409-5412.

Formigli, L., Papucci, L., Tani, A., Schivone, N., Tempestine, A., Orlandini, G.E., Capaccioli, S. and Orlandini, S.Z., 2000, "Aponecrosis: Morphological and biochemical exploration of a syncretic process of cell death sharing apoptosis and necrosis," J. Cell Physiol, 182:41-49.

Forrester, H.B, Albright, N., Ling, C.C. and Dewey, W.C., 2000, "Computerized video time-lapse analysis of apoptosis of REC: Myc cells X-radiated in different phases of the cell cycle," Radiat. Res., 154:625-639.

Gaal, J.C., Smith, K.R., and Pearson, C.K. 1987, "Cellular euthanasia mediated by nuclear enzyme: A central role for nuclear ADP-ribosylation in cellular metabolism," Trends Biochem. Sci., 12:129-132.

Gewirtz, D.A., 1999, "A critical evaluation of mechanisms of action proposed for the antitumor effects of the anthracycline antibiotics adriamycin and daunorubicin," Biochem. Pharm., 57:727-741.

Goldin, A., Kendetti, J.M., MacDonald, J.S., Muggla, F., Henney, J. and DeVita, V.T., 1981, "Current results of the screening program at the Division of Cancer Treatment, National Cancer Institute," Eur. J. Cancer, 17:129.

Green, D.R., 1998, "Apoptotic pathways: the roads to ruin," Cell, 94:695-698.

Grindey, G.B., Lowe, J.K., Divekey, A.Y., and Halaka, M.T., 1976, "Potentiation by guanine nucleosides of the growth-inhibitory effects of adenosine analogues on L1210 and Sarcoma 180 cells in culture," Cancer Res., 36:379-383.

Halmovitz-Friedman, A. Kan, C.C., Ehleiter, D., Persaud, R.S., McLoughlin, M., Fuks, Z. and Kolesnick, R.N., 1994, "Ionizing radiation acts on cellular membranes to generate ceramide and initiate apoptosis," J.Exp. Med., 180:525-535.

Herceg, Z. and Wang, Z.Q., 1999, "Failure of poly (ADP/ribose) polymerase cleavage by caspases leads to induction of necrosis and enhanced apoptosis," Mol. Cell. Biol., 19:5124-5133.

Herken, H., Lange, K. and Kolbe, H., 1969, "Brain disorder induced by pharmacological blockage of the pentose phosphate pathway," Biochem. Biophys. red. Commun., 36:93-100.

Herter, F., Weissman, S.G., Thompson, H.G. et al., 1961, "Clinical experience with 6-aminonicotinamide," Cancer Res. 21:31-37.

Hickman, J.A., 1992, "Apoptosis induced by anticancer drugs," Cancer Metast. Rev., 11:121-139.

Hunting, D., Gowans, B., and Henderson, J.F., 1985, "Effect of 6-AN on cell growth, poly (ADP-ribose) synthesis and nucleotide metabolism," Biochem. Pharmacol., 34:3999-4003.

Janicke, R.V., Sprengart, M.L., Wati, M.R. and Porter, A.G., 1998, "Caspase-3 is required for DNA fragmentation and morphological changes associated with apoptosis," J. Biol. Chem., 273:9357-9360.

Janicke, R.U., Ng, P., Sprengart, M.L., and Porter, A.g., 1998, "Casepase-3 is required for alpha-fodrin cleavage but dispensable for cleavage of other death substrates in apoptosis," J. Biol. Chem., 273:15540-5.

Jones, M., 1980, "Pyrimidine nucleotide biosynthesis in animals: Genes, enzymes and regulation of UMP synthesis," Ann. Rev. Biochem., 49:253-279.

Kass, G.E., Eriksson, J.E., Weis, M., Orrenius, S., and Chow, S.C., 1996, "Chromatin condensation during apoptosis requires ATP," Biochem. J., 318:749-52.

Kerr, J.F.R., Wyllie, A.H., and Currie, A.R. 1972, "Apoptosis: a basic biological phenomenon with wide-ranging implications in tissue kinetics," Brit. J. Cancer, 26:239-257.

King, M.P., and Attardi, G., 1989, "Human cells lacking mtDNA: Repopulation with exogenous mitochondria by complementation," Science, 246:500-503.

King, K.L. and Cidlowski, J.A., 1995, "Cell cycle and apoptosis: Common pathways to life and death," J. Cell Biochem., 58:175-180.

Kroemer, G., 1997, "Mitochondrial implication in apoptosis. Towards an endosymbiont hypothesis of apoptosis evolution," Cell Death Differ., 4:443-456.

Kroemer, G., Zamzami, N., and Susin, S.A., 1997, "Mitochondrial control of apoptosis," Immunol. Today, 18:44-51.

Krug, L.M., Ng, K.K., Kris, M.G., Miller, V.A., Tong, W., Heelan, R.J., Leon, L., Leung, D., Kelly, J., Grant, S.C. and Sirotnak, F.M., 2000, "Phase I and pharmacokinetic study of 10-propargyt-10-deazaaminopterin a new antifolate," Clin. Cancer Res., 3493-3498.

Kuida, K., Hayder, T.F., Kuan, C.Y., Gu, Y., Taya, C., Karasuyama, H., Su, M.S.S., Radic, P. and Flavell, R.A., 1998, "Reduced apoptosis and cytochrome c- mediated caspase activation in mice lacking caspase activation in mice lacking casepase 9," Cell, 94:325-337.

Lemasters, J.J., 1999, "Necraptosis and the mitochondrial permeability transition: shared pathways to necrosis and apoptosis," Am. J. Physiol., 276:G1-6.

Li, H., Zhu, H., Xu, C.J., 1998, "Cleavage of BID by caspase 8 mediates the mitochondrial damage in the Fas pathway of apoptosis," Cell, 94:491-501.

Li, W.W., Cole, P., Martin, D., Banerjee, D. and Bertino, J.R., 2000, "Methylthioadenosine phosphorylase (MTAP) status determines sensitivity to L-alanosine in human soft tissue sarcoma cell lines and is enhanced by 6-methylmercaptopurine riboside (MMPR)," Proc. AM. Assoc. Cancer Res., 41:240.

Liu, X., Kim, C.N., Yang, J., Jemmerson, R. and Wang, X., 1996, "Induction of apoptotic program in cell-free extracts: requirement for dATP and cytochrome C.," Cell, 86:147-157.

Lowe, S.W., 1995, "Cancer therapy and p53," Curr. Opin. Oncol., 7:547-553.

Marks, D.I., and Fox. R.M., 1991, "DNA damage, poly(ADP-ribosyl)action and apoptotic cell death as a potential common pathway of cytotoxic drug action," Biochem. Pharmacol. 42:1859-1867.

Martin, D.S., Fugman, R.A., Stolfi, R.L. and Hayworth, E., 1975, "Solid tumor animal model therapeutically predictive for human breast cancer," Cancer Chemother, Rep. Part 2, 5:89.

Martin, D.S., Stolfi, R.L., and Colofiore, J.R., 1997, "Perspective: The chemotherapeutic relevance of apoptosis and a proposed biochemical cascade for chemotherapeutically-induced apoptosis," Cancer Invest., 15:372-381.

Martin, D., Matel, C., and Koutcher, J., 2000, "Marked enhancement of radiotherapy-induced tumor regression by an NAD antagonist, 6-aminonicotinamide (6-AN)," Proc. Am. Assoc. Cancer Res., 41:283 (Abstract 1800).

Modica Napolitano, J.S. and Aprille, J.R., 2001, "Delocalized lipophilic cations selectivity target the mitochondria of carcinoma cells," Adv. Drug Deliv. Rev., 49:63-701.

National Institute of Health Consensus Development Conference Statement, 2001, "Adjuvant Therapy for Breast Cancer, Nov. 1-3, 2000," J. Natl. Cancer Inst., 93:979-989.

Ngyuyen, B.T., El Sayed, Y.M., and Sadee, W., 1984, "Interaction among the distinct effects of adenine and guanine depletion in mouse lymphoma cells," Cancer Red., 44:2272-2277.

Nicotera, P. and Leist, M., 1997, "Mitochondrial signals and energy requirement in cell death," Cell Death Differ, 4:516.

Nobori, T., Karras, J.G., Della Ragione, F., Waltz, T.Z., Chen P.P. and Carson, D.A., 1991, "Absence of methylthioadenosine phosphorylase in human gliomas,"Cancer Res., 51:3193-3197.

Nobori, T., Szinai, I., Arnox, D., Parker, B., Olopade, O.I., Buchhagen, D.L. and Carson, D.A., 1993, "Methylthioadenosine phosphorylase deficiency in human non-small cell lung cancers," Cancer Res., 53:1098-1101.

Presta, M., Rusunati, M., Belleri, M., Morbedelli, L., M. and Ribatti, D., 1999, "Purine analouge 6-methylmercaptopurine riboside inhibits early and late phases of the angiogenesis process," Cancer Res., 59:2417-2424.

Raffray, M. and Cohen, G.M., 1997, "Apoptosis and necrosis in toxicology: a continuum or distinct modes of cell daeth?" Pharmacol. Ther., 75:153-177.

Reed, J.C., 1995, "Regulation of apoptosis by bcl-2 family proteins and its role in cancer and drug resistance," Curr. Opin. Oncol., 7:541-546.

Roy, N., Dveraux, Q.L., Takahashi, R., Salvesen, G.S. and Reed, J.C., 1997, "The c-IAP-1 and c-IAP-2 proteins are direct inhibitors of specific caspases," EMBO J., 16:6914-6925.

Sausville, E.A. and Feigal, E., 1999, "Evolving approaches to cancer drug discovery and development at the National Cancer Institute," USA Ann. Oncol., 10:1287-1291.

Schmitt, C.A. and Lowe, S.W., 2002, "A senescence program controlled by p53 and p16 ink4a contributed to the outcome of cancer therapy," Cell, 109:335-346.

Schmitt, C.A. and Lowe, S.W., 2002, "Apoptosis and chemoresistance in transgenic cancer models," J. Mol. Med., 80:137-146.

Schraufstaffer, I.U., Hinshaw, D.B., Hyslop, P.S., Sragg, R.H., and Cochrane, C.G., 1986, "Oxidant injury of cells DNA strand-breaks activate polyadenosine diphosphate polymerase and lead to depletion of nicotinamide adenine dinucleotide," J. Clin. Invest., 77:1312-1320.

Scudiero, D.A., Monks, A., and Sausville, E.A., 1998, "Cell line designation change: Multidrug-resistant cell line in the NCI anticancer screen," J. Natl. Cancer Inst., 90:862.

Serafino, A., Sinibaldi-Vallebono, P., Lazzarino, G., Tavazzi, B., DiPiarro, D., Rosi, G. and Ravagnan, G., 2000, "Modifications of mitochondria in human tumor cells during enthracycline-induced apoptosis," Anticancer Res., 20:3383-3394.

Shantz, G.D., Smith, C.M., Fontanella, L.J., Lau, H.K.F., and Henderson, J.F., 1973, "Inhibition of purine nucleotide metabolism by 6-methlmercaptopurine ribonucleoside and structurally related compounds," Cancer Res., 33:2867-2871.

Shimizu, S., Equchi, Y., Kamike, W., Itoh, Y., Hasegawa, J., Yamabe, K., Otsuid, Y., Matsuda, H. and Tsujimoto, Y., 1996, "Induction of apoptosis as well as necrosis by hypoxie and predominant prevent of apoptosis by bci-2 and bci-x," Cancer Res., 56:2161-2166.

Sirotnak, F.M., De Graw, J.I., Colwell, W.T. and Piper, J.R., 1998, "A new analogue of 10-deazaaminopterin with markedly enhanced curative effects against human tumor xenografts in mice," Cancer Chemother. Pharmacol., 42:313-318.

Staunton, M.J. and Gaffney, E.F., 1998, "Apoptosis: basic concepts and potential significance in human cancer," Arch. Pathol. Lab. Med., 122:310-319.

Stolfi, R.L., Martin, D.S. and Fugman, R.A., 1971, "Spontaneous murine mammary adecocarcinoma: Model system for the evaluation of combined methods of therapy," Cancer Chemother. rep. Part 1, 55:239.

Stolfi, R.L., Stolfi, L.M. Sawyer, R.C., and Martin, D.S., 1988, "Chemotherapeutic evaluation using clinical criteria in spontaneous, autochthomous murine breast tumors," J. Nat. Cancer Inst., 80:52-5.

Street, J.C., Mahmoud, V., Ballon, D., Alfieri, A.A., and Koutcher, J.A., 1996," 13C and 31p NMR Investigation of effect of 6-aminonicotinamide on metabolism of RIF-1 tumor cells in vitro," J. Biol. Chem., 271:4113-4119.

Street, J.C., Alfieri, A.A., and Koutcher, J.A., 1997, "Quantitation of metabolic and radiobiological effects ogf 6-aminonicotinamide in RIF-1 tumor cells in vitro," Cancer Res., 57:3956-3962.

Susin, S.A., Zamzami, N., Castedo, M.,Hirsch, T., Marchetti, P., Macho, A., Dauges, E., Gauskens, M. and Kroemer, G., 1996, "Bci-2 inhibits the mitochondrial release of an apoptogenic protease," J. Exp. Med., 184:1331-1342.

Tanizawa, A., Kubota, M., hashimoto, H., Shimizu, T., Takimoto, T., Kitoh, T., Akiyama, Y., and Mikama, H., 1989, "VP-16-induced nucteotide pool changes and poly (ADP-ribose) synthesis: The role of VP-16 in interphase death," Exp. Cell Res., 185:237-246.

Tian, W-N., Braunstein, L.D., Apse, K., Pang, J., Rose, M., Tian, X., and Stanton, R.C., 1999, "Importance of glucose-6-phosphate dehydrogenase activity in cell death," Am. J. Physiol., 276 (Cell Physiol. 45):C1121-C1131.

Tian, W-N., Braunstein, L.D., Apse, K., Pang, J., Rose, M, Tian and Stanton, R.C., 1998, "Importance of Glucose-6-phosphate dehydrogenase activity for cell growth," J. Biol. Chem., 273:10609-10617.

Tyagl, A.K. and Cooney, D.A., 1984, "Biomedical pharmacology, metabolism and mechanism of action of L-alanosine, a novel, natural antitumor agent," Adv. Pharmacal. Chemother. 20::69-121.

Warnick, C.T., and Patterson, A.R.P., 1973, "Effect of methylthioinosine on nucleoside concentration in L5158 cells," Cancer Res., 33:1711-1715.

Wielinga, P.R., Reid, G., Chalta, E.E. van der Heijden, I., van Deemter, L., De Haas, M., Mol, C., Kutt, A.J., Groeneveld, E., Schuetz, J.D., Brouwer, C., de Abrau, R.A., Wijnholds, J., Bejnen, J.H. and Borst, P., 2002, "Thicpurine metabolism and Identification of the Thiopurine metabolites transported by MRP4 and MRP5 overexpressed in human embryonic kidney cells," Mol. Pharm., 62:1321-1331.

Williams-Ashman, H.G., Seidenfeld, J. and Galletti, P., 1982, "Trends in the biochemical pharmacology of 5'-deoxy-5'-methylthioadenosine," Biochem. Pharmacal., 31:277-288.

Woods, R.A., Henderson, R.M., and Henderson, J.F., 1978, "Consequences of Inhibition of purine biosynthesis de novo by 6-methylmercaptopurine ribonucleoside in cultured lymphoma L5178 cells," Euro. J. Cancer, 14:765-70.

Wyllie, A.H., 1993, "Apoptosis [The 1992 Frank Rose Memorial Lecture], " Br. J. Cancer., 67:205-208.

Xiang, J., Chao, T. and Korsmyer, S.J., 1996, "Bax-induced cell death may not require interleukin 1-converting enzyme-like proteases," Proc. Natl. Acad. Sci. USA, 93:14359-14563.

Yoshida, H., Kong, Y.Y., Yoshida, R., Elia, A.J., Hakem, R., Penninger, J.M. and Mak, T.W., 1998, "Apaf-1 is required for miltochondrial pathways of apoptosis and brain development," Cell, 94:739-750.

Young, I., Young, G.L. Wiley, J.S. and van der Weyden, M.B., 1985, "Nucleoside transport and cytosine arabinosine (ara C) metabolism in human T lymphoblasts resistant to ara C, thymidine and 6-methyemercap to purine riboside," Eur. J. Cancer Clin. Oncol., 21(9):1077-1082.

Zamzami, N., Susin, S.A., Marchetti, P., Hirsch, T., Gomez-Monterrey, I., Castedo, M., and Kroemer, G., 1996, "Mitochondrial control of nuclear apoptosis (see co=ents)," J. Exp. Med., 183:1533-44.

Zou, H., Li, Y., Liu, X., and Wang, X., 1999, "An apaf-1cytochrome c multimeric complex is a functional apoptosome that activates procaspase-9," J. Biol. Chem., 274:11549-1156.

European Communication for Sloan-Kettering Institute for Cancer Research, European Application No. 01986104.6, Filed Jul. 2, 2003, Dated Sep. 6, 2007.

Office Action for Martin et al., U.S. Appl. No. 10/518,003, Filed Mar. 14, 2005, dated Apr. 2, 2007.

Office Action for Martin et al., U.S. Appl. No. 10/518,003, Filed Mar. 14, 2005, dated Oct. 17, 2005.

Brown, J.M. and B.G. Wouteres, 2001, "Apoptosis; mediator or mode of cell killing by anticancer agents?" Drug Resistance Updates, 4:135-6.

Schmitt, D.A., and S.W. Lowe, 2001, "Apoptosis is critical for drug response in vivo," Drug Resistance Updates, 4:132-134.

Schmitt, E., Sane, A.T. and R. Bertrand, 1999, "Activation and the role of caspases in chemotherapy-induced apoptosis," Drug Resistance Updates 2:21-29.

* cited by examiner

TREATMENT OF CANCER BY REDUCTION OF INTRACELLULAR ENERGY AND PYRIMIDINES

The invention disclosed herein was made with government support under National Cancer Institute RAID Grant Application #153. Accordingly, the U.S. Government has certain rights in this invention.

This application claims priority of U.S. Ser. No. 60/250, 993, filed Dec. 4, 2000, and International PCT/US01/46886, filed Dec. 4, 2001, the contents of which are hereby incorporated into this application by reference.

Throughout this application, various references are referred to. Disclosures of these publications in their entireties are hereby incorporated by reference into this application to more fully describe the state of the art to which this invention pertains.

BACKGROUND OF THE INVENTION AND CANCER RELEVANCE

Drug resistance is the central problem of cancer chemotherapy. Clinically effective combination chemotherapy can cause impressive objective tumor response rates, including complete tumor regressions, but some cancer cells are of lesser sensitivity to the agent (i.e., are drug-resistant), are only damaged, recover, and re-grow. The delayed tumor recurrence yields only a short remissions period with little improvement in survival time.

There are many mechanisms of drug resistance. Multiple independent mechanisms of drug resistance may coexist in a population of tumor cells as well as in the same cancer cells, as they arise from multiple genetic changes in single cell clones, and are part of the heterogeneity of the neoplastic process. Mechanisms of drug resistance have been largely identified, and this knowledge has suggested many specific approaches to overcoming one or another type of clinical drug resistance, but these attempts have failed as they also potentiate drug toxicity towards normal tissues.

The therapeutic research strategy for several decades has been that the administration of multiple drugs with different properties and mechanisms of action at optimal doses and intervals should result in cells resistant to one class of drug being killed by another drug in the regimen. However, the extensive, clinical data over these decades has evidenced only a minor impact on treatment outcome along with troublesome and serious toxic side effects (e.g., emesis, diarrhea, alopecia, asthenia, fatigue, myelosuppression, febrile netropenia requiring hospitalization, neurosensory and neuromotor disturbances, arthralgias and myalgias, heart failure, and treatment-related deaths). Despite the long dismal history of repeated failures to meaningfully improve survival rates by aggressive combination chemotherapy with non-cross-reacting drugs, hope is nevertheless expressed that the future will be different with the new molecularly targeted agents.

However, no matter how many effective mechanistically-different anticancer agents there are, and no matter how superior their therapeutic index, cancer cell demise occurs by only two cell death pathways (necrosis or apoptosis). If the latter two cell death mechanisms are attenuated by drug resistance mechanisms (e.g. p-glycoprotein and/or glutathione prevent intracellular drug levels reaching concentration levels sufficient to fully activate the necrosis pathway; caspase deletions and endogenous caspase inhibitors prevent completion of apoptosis), these tumor cells are only sublethally injured, recover, and proliferate to kill the patient. The history of the results of these clinical trials is therapeutic equivalence between different combination chemotherapy "doublets" and "triplets". The repeated failures of this approach to overcoming clinical drug resistance— i.e., the lack of clinically relevant differences in overall survival—means only continuance of palliative treatment with decisions tailored individually around such issues as differences in toxicity profiles, patients' age and performance status, and quality of life.

New agents, no matter a new molecular target or superior therapeutic index, can only kill cancer cells if there is completion of the cell death pathways through death's door. In drug-resistant cells, it is not the activation of their cell death pathways by clinically effective anticancer agents that is at fault, but rather pathway completion to death of the cell. This reality suggests that continuance of this failed strategy utilizing only aggressive combination chemotherapy with non-cross-reacting drug-will likely result in—to quote Yogi Berra—"déjà vu all over again".

The above facts suggest the development of a treatment (co-administered with the initiation of activity in the cell death pathways by anticancer agents) that complements (augments) the agent-induced initiation of activity in cell death pathways to completion; namely, to cell death. That treatment, focused on severe ATP depletion, has been developed and proven at the preclinical level, and is about to undergo validation by clinical trial with clinical supplies of the ATP-depleting regimen provided by the NCI RAID grant mechanisms.

Heterogeneous neoplastic cell populations likely contain cancer cells of variable sensitivity to the anticancer agents. Less sensitive cells would not receive enough damage to reduce ATP to low levels sufficient to cause necrotic death. We hypothesized that biochemical modulation to further depress ATP to lower lethal-inducing levels would kill these sublethally-injured cells, augment tumor regressions, and perhaps even yield some cures.

SUMMARY OF THE INVENTION

This invention provides a method for treating a cancer subject comprising administering to the subject a combination of ATP-depleting agents, pyrimidine antagonist, and an anticancer agent to which the treated cancer is sensitive at concentrations which deplete the ATP level to at least 15% of normal in cancer cells.

This invention provides a method for induction of cancer cell death comprising contacting said cancer cell with a combination of ATP-depleting agents at concentrations which deplete the ATP level to at least 15% of normal in cancer cells.

This invention provides a method for treating a cancer subject, and for the induction of cancer cell death, comprising administering to the subject a combination of ATP-depleting agents, plus an anticancer agent to which the treated cancer is sensitive, at concentrations which together collectively deplete the ATP levels to at least 15% of normal in cancer cells.

This invention provides a combination of ATP-depleting agents at concentrations which deplete the ATP level to at least 15% of normal in cancer cells, a pyrimidine antagonist, and an anticancer agent to which the treated cancer is sensitive.

Furthermore, this invention provides a composition comprising an effective amount of a combination of ATP-depleting agents at concentrations which deplete the ATP level to at least 15% of normal in cancer cells, a pyrimidine antagonist, and an anticancer agent to which the treated cancer is sensitive.

This invention also provides a method for treating a subject bearing cancer cells comprising administering to the subject an agent at a concentration capable of inducing necrosis in cancer cells.

DETAILED DESCRIPTION OF THE FIGURES

FIG. 1. DNA strand breaks activate PARP which cleaves NAD into PAR moieties. The result is a marked decrease in NAD+ with a consequent fall in ATP until finally there is insufficient ATP to sustain survival of the cell, and cell death by necrosis occurs (PARP=poly (ADP-ribose) polymerase; PAR=poly (ADP-ribose; NAD+=nicotinamide adenine dinucleotide; ATP=adenosie triphosphate.

Figure 2:
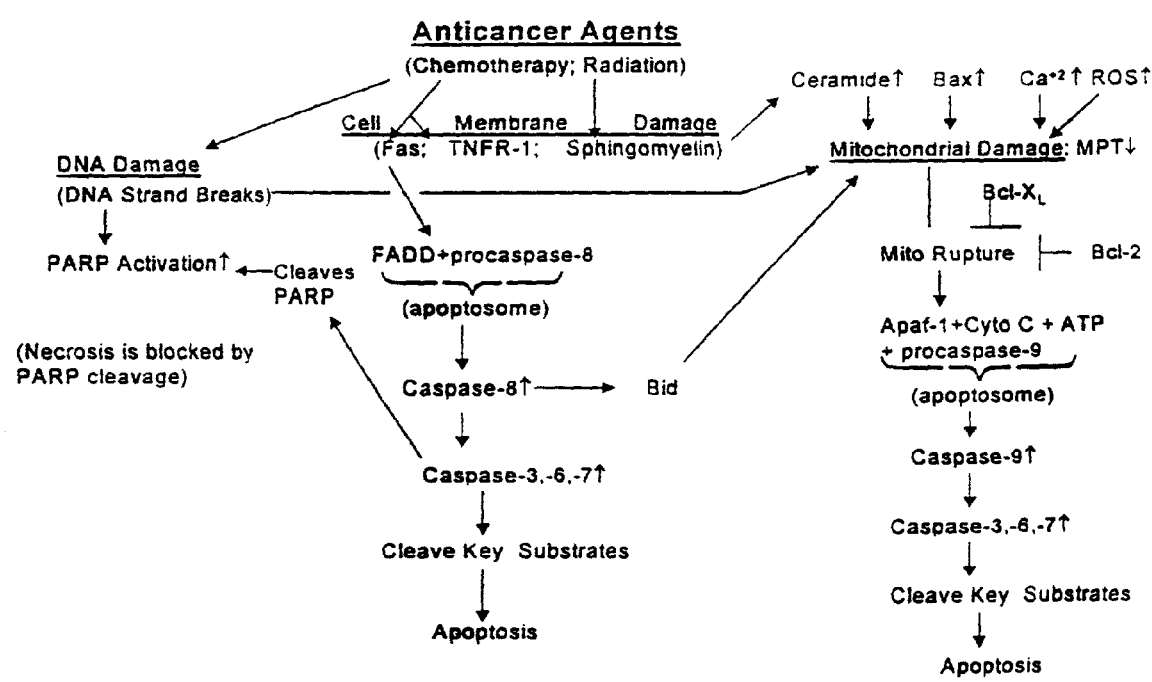

FIG. 2. Schematic outline of sequential biochemical pathways to apoptosis induced by anticancer agents. PARP=poly (ADP-ribose) polymerase. Fas=cell surface membrane receptor; TNFR-1=Tumor Necrosis Factor Receptor-1; ROS=Reactive Oxygen Species; MPT=mitochondrial permeability transition; Cyto c=cytochrome c; Mito=mitochondrial.

Figure 3:
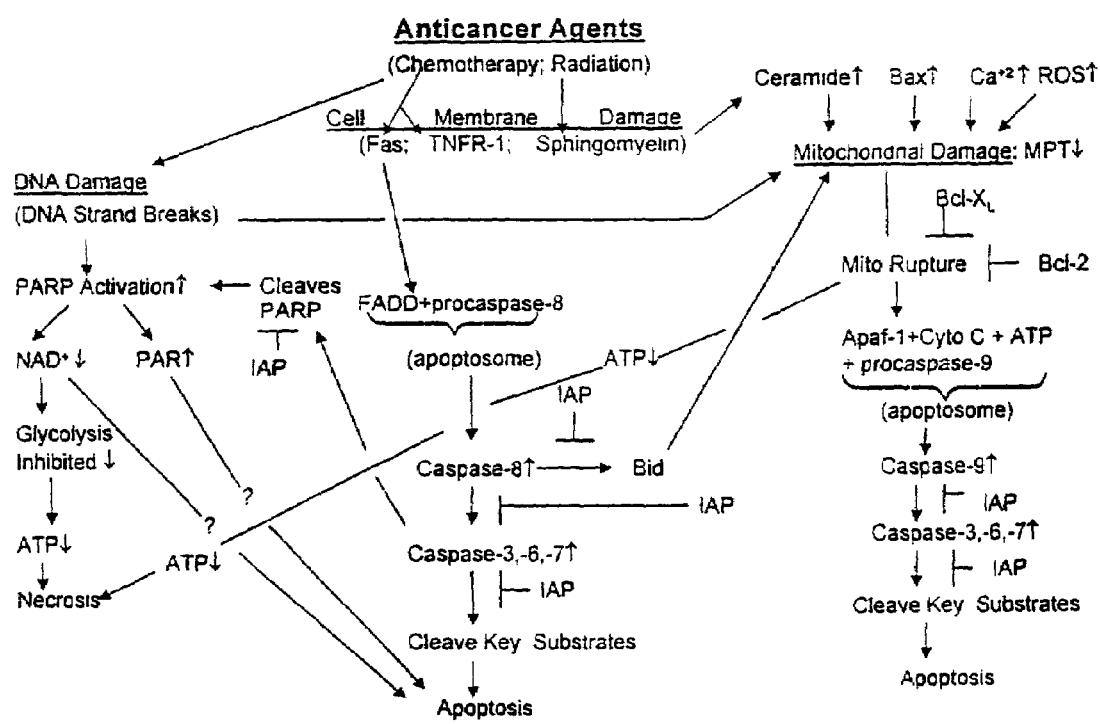

FIG. 3. Schematic outline of necrotic and apoptotic pathways with endogenous inhibitors of apoptosis, IAPs; i.e., inhibitors of caspases (62). If PARP cleavage is prevented, the continued activity of PARP leads to enhancement of both necrosis and apoptosis (70, 42). The ? marks indicate that the possible relevance of NAD+ levels and PAR, poly (ADP-ribose) polymers, to the enhanced apoptosis is not known.

DETAILED DESCRIPTION OF THE INVENTION

This invention provides a method for treating a cancer subject comprising administering to the subject a combination of ATP-depleting agents, pyrimidine antagonist, and an anticancer agent to which the treated cancer is sensitive at concentrations which deplete the ATP level to at least 15% of normal in cancer cells.

This invention provides a method for induction of cancer cell death comprising contacting said cancer cell with a combination of ATP-depleting agents at concentrations which deplete the ATP level to at least 15% of normal in cancer cells. This invention provides the above method, further comprising a pyrimidine-depleting agent. The invention also provides the above method, further comprising an anticancer agent. In an embodiment, the cancer is clinically sensitive to the employed anticancer agent.

This invention provides a method for treating a cancer subject, and for the induction of cancer cell death, comprising administering to the subject a combination of ATP-depleting agents, plus an anticancer agent to which the treated cancer is sensitive, at concentrations which together collectively deplete the ATP levels to at least 15% of normal in cancer cells. In an embodiment, the ATP-depleting agents comprise 6-methylmercaptopurine riboside (MMPR), 6-Aminonicotinomide (6-AN) and alanosien (AL). In an embodiment, the method comprises N-(phosphonacetyl)-L-aspartic acid (PALA). In another embodiment, the ATP-depleting agents comprise 6-methylmercaptopurine riboside (MMPR) and alanosine (AL). In yet another embodiment, the method comprises N-(phosphonacetyl)-L-aspartic acid (PALA). In still another embodiment, the method further comprises dehydroepiandrosterone (DHEA). In a further embodiment, the method comprises oxythiamine (OT). In a separate embodiment, the method comprises dehydroepiandrosterone (DHEA) and oxythiamine (OT). In still another embodiment, the method comprises 6-Aminonicotinomide (6-AN). In a further embodiment, the method comprises an anti-myelosuppression agent. In an additional embodiment, the anti-myelosuppression agent is G-CSF.

This invention further provides a composition comprising a combination of ATP-depleting agents at concentrations which deplete the ATP level to at least 15% of normal in cancer cells, a pyrimidine antagonist, and an anticancer agent to which the treated cancer is sensitive.

In addition, this invention provides a composition comprising an effective amount of a combination of ATP-depleting agents at concentrations which deplete the ATP level to at least 15% of normal in cancer cells, a pyrimidine antagonist, and an anticancer agent to which the treated cancer is sensitive. In an embodiment, the composition comprises a pyrimidine-depleting agent. In another embodiment, the composition comprises an anticancer agent to which the cancer is sensitive. In a separate embodiment, the ATP-depleting agents comprise 6-methylmercaptopurine riboside (MMPR), 6-Aminonicotinomide (6-AN) and alanosine (AL). In yet another embodiment, the composition comprises N-(phosphonacetyl)-L-aspartic acid (PALA). In a separate embodiment, the ATP-depleting agents comprise 6-methylmercaptopurine riboside (MMPR) and alanosine (AL). In a further embodiment, the composition further comprises N-(phosphonacetyl)-L-aspartic acid (PALA). In another embodiment, the composition comprises dehydroepiandrosterone (DHEA). In yet another embodiment, the composition comprises oxythiamine (OT). In a further embodiment, the composition comprises dehydroepiandrosterone (DHEA) and oxythiamine (OT). In another embodiment, the composition comprises 6-Aminonicotinomide (6-AN). In a separate embodiment, the composition comprises an anti-myelosuppression agent. In an additional embodiment, the anti-myelosuppression agent is G-CSF.

This invention further provides a pharmaceutical composition comprising the above composition and a pharmaceutically acceptable carrier.

In addition, this invention provides a method for treating a subject bearing cancer cells comprising administering to the subject an anticancer agent at a concentration capable of inducing necrosis in cancer cells. In an embodiment, the agent is an ATP-depleting regimen. In another embodiment, the method comprises a pyrimidine-depleting agent. In a further embodiment, the method comprises an anticancer agent. In a separate embodiment, the cancer is clinically sensitive to the employed anti-cancer agent.

This invention further provides a method for induction of cancer cell death comprising contacting said cancer cell with an agent capable of inducing necrosis in cancer cells. In an embodiment, the agent is an ATP-depleting regimen. In another embodiment, the method comprises a pyrimidine-depleting agent. In yet another embodiment, the method comprises an anticancer agent.

Finally, this invention provides a pharmaceutical composition comprising a combination as described above and a pharmaceutically acceptable carrier. For the purposes of this invention, "pharmaceutically acceptable carriers" means any of the standard pharmaceutical carriers. Examples of suitable carriers are well known in the art and may include, but are not limited to, any of the standard pharmaceutical carriers such as a phosphate buffered saline solution and various wetting agents. Other carriers may include additives used in tablets, granules and capsules, etc. Typically such carriers contain excipients such as starch, milk, sugar, certain types of clay, gelatin, stearic acid or salts thereof, magnesium or calcium stearate, talc, vegetable fats or oils, gum, glycols or other known excipients. Such carriers may also include flavor and color additives or other ingredients. Compositions comprising such carriers are formulated by well-known conventional methods.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

EXPERIMENTAL DETAILS

First Series of Experiments

The ATP-Depleting and Pyrimidine-Depleting Agents. Biochemical modulation is the manipulation of intracellular metabolic pathways by agents to produce selective enhancement of antitumor effects by the anticancer agent (7). Since damage to the glycolytic generation of ATP in cancer cells was shown to occur following the administration of DNA-damaging anticancer agents (1-6), 6-aminonicotinamide (6-AN), an NAD antagonist, known to inhibit glycolytic production of ATP (8-13), was administered with anticancer agents to further deplete intracellular ATP.

6-Methylmercaptopurine riboside (MMPR), known to inhibit de novo purine biosynthesis (14, 15), and thereby limit adenine supplies for ATP production, was also concomitantly administered. In high dosage, MMPR also decreases pyrimidine ribonucleotide concentrations in vitro (16). Since a de novo pyrimidine synthesis inhibitor, PALA, as a single agent in low non-toxic dosage, can selectively lower pyrimidine nucleotide levels in tumors (17), low-dose PALA was added to MMPR therapy to further lower MMPR's reduction of pyrimidine synthesis. The three agents—PALA, MMPR, and 6-AN—were evaluated alone, in various double combination, and as a triple combination against advanced breast tumors in mice. Pooled experiments (45, 85) demonstrated that neither the maximum tolerated dose of MMPR alone, nor 6-AN alone, nor the double combination of PALA+6-AN produced cell kill. There were no partial regressions of tumors (P.R.,≧50% tumor shrinkage in the volume of the initially measured tumor). However, tumor growth was inhibited in these groups as compared to saline controls.

Cell cycle events (i.e., proliferation) require a minimal ATP content to undergo proliferation. If ATP depletion is reduced to levels above 15% of normal, but is below the minimal level necessary for cell division, only proliferation arrest (i.e., tumor growth inhibition), and not cell death (i.e., tumor regression) will ensue (51-52). Table 1 records that MMPR alone (Group 1), and 6-AN alone (Group 2), depress tumor ATP levels 48 hours after treatment to 34% and 69%, respectively, compared to saline-treated control tumors. These are ATP levels compatible with the tumor growth inhibitions produced by MMPR alone and 6-AN alone in the above-pooled published experiments (48, 85). PALA does not effect ATP depletion, and in the low dosage that was administered reduces pyrimidine biosynthesis, but does not have anticancer activity (17). Hence, the above-noted combination of low dose PALA+6-AN only inhibited tumor growth due to the 6-AN, which alone only reduced ATP to 69% of normal (48 hours, Group 1, Table 1)

In contrast, the double combination of MMPR (a strong ATP depleter—34% of normal, 48 hours, Group 1, Table 1) plus PALA (which is devoid of an ATP depleting effect) produced a very few partial tumor regressions, 7% P.R. (45, 85). The MMPR-induced depletion of ATP to 34% is an average; hence, a few individual tumors likely have an ATP level ≦15% of normal, a level shown to be insufficient to sustain cell viability (51-52), and particularly in the presence of the severe pyrimidine depletion produced by the double combination of PALA+MMPR, as is explained below.

(Please note that the murine tumors in these experiments are first passage subcutaneous transplants from a tumor brei made mixing the cancer cells of 3 or 4 single, spontaneous, autochthonous breast tumors, the $CD_8F_1$, tumor model previously included in the National Cancer Drug Screening Program (86-89). All spontaneous tumors, whether human or murine, have a heterogenous neoplastic cell population. Since each experiment consists of a brei composed of several different spontaneous tumors, the neoplastic cell composition is somewhat different from experiment to experiment, resulting in some quantitative differences between experiments. However, each experiment has its own control, and the results are quantitatively relevant within individual experiments, as are trends among experiments).

In this series of three pooled published experiments, the double combination of MMPR+6-AN produced an objective response rate of 17% P.R. (45, 85). This therapeutic result is compatible with the MMPR+6-AN induced cell-killing average ATP level of 15% of normal (Table 1, Group 3, 48 hours). Note that the low ATP level of 15% induced by MMPR+6-AN is, as expected, unchanged (still 15%) by the

TABLE 1

Effect of MMPR + 6-AN + PALA on tumor ATP pools in $CD_8F_1 mice^d$.

| Group | Treatment | 6 HR$^b$ ug ATP/ mg ± S.E | % Saline Control | 24 HR$^a$ ug ATP/ mg ± S.E | % Saline Control | 48 HR$^a$ ug ATP/ mg ± S.E | % Saline Control | 72HR$^a$ ug/ATP mg ± S.E | % Saline Control |
|---|---|---|---|---|---|---|---|---|---|
| 1. | MMPR$_{150}$ | 3.3$^c$ ± 0.32 | 47 | 3.3$^b$ ± 0.96 | 47 | 1.6$^b$ ± 0.59 | 34 | 9.0$^d$ ± 2.4 | 127 |
| 2. | 6-AN$_{10}$ | 5.5$^b$ ± 0.21 | 77 | 5.3$^b$ ± 0.136 | 75 | 4.9$^b$ ± 0.16 | 69 | 12.0$^c$ ± 3.9 | 169 |
| 3. | MMPR$_{150}$ + 6-AN$_{10}$ | 4.1$^b$ ± 0.49 | 58 | 2.2$^b$ ± 0.08 | 31 | 1.1$^b$ ± 0.36 | 15 | 16.0$^c$ ± 3.6 | 225 |
| 4. | MAP | 3.9$^b$ ± 0.11 | 55 | 2.3$^b$ ± 0.31 | 32 | 1.1$^b$ ± 0.14 | 15 | 8.1$^c$ ± 0.7 | 114 |

$^a$Mean ± S.E. of 10 tumors/group (11 experiments)
$^b$Statistical comparison to group 1 (saline control), Significant = P value less than or equal to 0.05
$^c$Mean ± S.E. of 6 tumors group (4 experiments)
$^d$Subscript = mg/kg body weight; i.p. injections; 1$^{st}$ passage tumor transplants of $CD_8F_1$ spontaneous breast tumors.

addition of PALA to MMPR+6-AN (Group 4, Table 1). However, in the presence of this severe limitation to ATP availability (15% of normal), the triple drug combination of MMPR+6-AN+PALA produced a P.R. rate of 61% (45, 85). The severely depleted ATP levels likely inhibit the salvage pathway formation of pyrimidine di- and triphosphates at the kinase step. Pyrimidine nucleotides serve essential functions in nucleic acid metabolism and sugar nucleotide formation for glycosylation of proteins and lipids. It is not surprising that severe inhibition of pyrimidine biosynthesis (due to PALA+high dose MMPR), in the presence of severe ATP depletion (due to MMPR+6-AN), enhances tumor regressions over MMPR+6-AN (45, 85). The uridine triphosphate pools in the in vivo MAP-treated tumors were sharply reduced to 14% of normal (45). It is the severe lowering of ATP levels (15% of normal) that is the key ingredient that allows the severe pyrimidine depletion to appreciably augment the anticancer activity of MMPR+6-AN+PALA (a 61% P.R.) over that of MMPR+6-AN (a 17% P.R.).

MAP is the acronym for the three-drug combination (MMPR+6-AN+PALA). (In previous publications the acronym PMA, was employed for the same three drugs in combination).

Although MMPR+6-AN effect the all-important ATP depletion to cancer cell-killing levels of ≦15% of normal (51-52), another reason for including PALA with MMPR+6-AN (i.e., MAP) is pertinent to the administration of DNA-damaging anticancer agents. The induction of apoptosis by the anticancer agents causes mitochondrial damage in sublethally injured cancer cells. Pyrimidine de novo synthesis is functionally linked to the respiratory chain in the inner mitochondrial membrane by mitochondrial-bound dihydroorotate dehydrogenase, the fourth enzyme of de novo pyrimidine synthesis. Thus, PALA (+high dose MMPR) should further lower the reduction of pyrimidine levels due to the mitochondrial damage effected by an anticancer agent-induced apoptotic biochemical cascade in surviving but sublethally injured cells. It has been shown previously that cells which had been completely depleted of mitochondria become pyrimidine auxotrophs because of the deficiency of the respiratory-chain-dependent dihydroorotate dehydrogenase (18). A minimal level of pyrimidine nucleotides is essential to sustain cell life. MAP severely reduces both ATP and pyrimidine levels in cancer cells. In anticancer agent-sublethally-injured cancer cells, ATP and pyrimidine levels are depleted by the mitochondrial damage induced by the apoptotic biochemical cascade initiated by the anticancer agent. Anticancer agents produce a tumor regression rate by directly killing many cancer cells by either necrosis or apoptosis, but they also effect sublethal injury to less sensitive cancer cells from which they will recover. MAP targets their sublethally injured cancer cells before they can recover, further decreasing their ATP and pyrimidine levels, killing these cells, and thereby markedly enhances tumor regressions. It is the anticancer agents that preferentially reduce ATP and pyrimidines, two metabolites that are essential for cell viability, to low levels in sublethally injured cancer cells, and thereby create a therapeutic opportunity for biochemical modulation (e.g., MAP) to further reduce them to lower levels insufficient to sustain the recovery of these injured cancer cells.

The central importance of severe ATP depletion to the tumor regressions (i.e., cancer cell deaths) produced by MAP is illustrated in our previously published in vivo experiments (53) investigating the prolonged retention (4 days) of intracellular MMPR-P (i.e., MMPR phosphate) following MAP administration to mice bearing advanced tumors. MMPR is phosphorylated by adenosine kinase to MMPR-P which inhibits de novo purine synthesis at the level of amidophosphoribosylpyrophosphate transferase, and this inhibition causes ATP depletion. The MMPR-depletion of ATP is driven by prolonged MMPR-P levels over an extended period (4-5 days) due to continuous resynthesis of MMPR-P by adenosine kinase. Following MAP administration, tumor ATP measurements (% of control) on days 2,3,4 and 5 averaged 52%, 38%, 35% and 50%, respectively, and MMPR-P was retained in the tumors at a high level over this prolonged period. The average ATP measurements of 38% and 35% likely include cell-killing ATP values ≦15% of normal because 3 partial tumor regressions were produced among ten advanced tumor-bearing mice. Another group of ten mice bearing the same transplants of advanced tumors received the same MAP treatment followed 6 hours later with iodotubercidin, an inhibitor of adenosine kinase, to allow an initial period of synthesis of MMPR-P prior to inhibition of adenosine kinase by iodotubercidin. However, this treatment prevented both the prolonged accumulation of MMPR-P and strong ATP depletion, producing tumor ATP values (% of control) of only 56%, 53%, 74% and 88% on days 2,3,4 and 5. In the presence of such poor ATP depletion there were no partial tumor regressions.

The data (53) demonstrate that severe ATP depletion is necessary and central to MAP-induced tumor regression. Pyrimidine depletion (i.e., PALA) makes a substantial contribution to achieving still more cancer cell deaths (i.e., greater tumor regressions) only in the presence of severe ATP depletion. The biochemical damage done to sublethally injured cancer cells by anticancer agents renders these cells vulnerable to cell death by severe ATP-pyrimidine depletion.

ATP Depletion Clearly Occurs—Even without the ATP-depleting contribution of a DNA-damaging anticancer agent (FIG. 1), the combination of just MMPR+6-AN has been shown to effect severe lowering of tumor ATP levels in tumor-bearing animals. Specifically, the tumors of mice treated with MMPR+6-AN (Group 3, Table 1) show a depletion to 15% of normal 48 hours after administration (19).

MAP+radiotherapy (23)—The MAP regimen, when combined with radiation, produced cures for the first time in the murine advanced spontaneous breast tumor system, demonstrating the potential for this new therapeutic approach to convert merely palliative (i.e., temporary tumor remission) treatment to curative therapy. Cures are claimed because the advanced murine tumors (treated when the tumor-bearing mice were 3 months old with only three intermittent courses of MAP+radiation every 10-11 days ending at day 21) underwent complete tumor regressions which continued in 25% of the mice for more than a year (380 days). In contrast, no complete regressions were obtained with MAP alone and only one short-lived complete tumor regression was obtained in animals treated with radiation alone.

Summary of Preclinical Therapeutic Results with MAP+Cancer Chemotherapy—MAP plus each of eight mechanistically-different anticancer drugs was administered to advanced tumor-bearing mice with a variety of tumor types (murine breast cancers, colon tumors and leukemia, and human breast cancer xenografts). The biochemical modulatory effort with MAP dramatically enhanced treatment of these tumors with agents that included doxorubicin, paclitaxel, cisplatin, 5-fluorouracil, phenylalanine mustard, cyclophosphamide, mitomycin C, etoposide (20-27). The overall antitumor results with a variety of anticancer agents demonstrated safe and impressive significant augmentation of tumor regression, including complete regressions, and even some (25%) cures (23).

The addition of MAP to combination chemotherapy with two anticancer agents (FU+Adria) was safe, without need for dose reduction, and yielded enhanced antitumor activity, including CRs not previously achieved (22). The results encourage the prospect of the safe addition of MAP to a large number of anticancer agents in combination with the likelihood of even greater anticancer results (e.g., after increased CRs comes cures).

Preclinical MAP Toxicity—MAP can cause body weight loss in mice. However, this weight loss is not accompanied by diarrhea or by histopathologic changes in organs (such as the intestine). A severe decrease in eating and drinking for 3-4 days after each of the three courses of intermittent chemotherapy was noted. Treatment-conditioned weight loss due to failure to eat or drink is not unusual for animals receiving intensive chemotherapy. Importantly, weight loss, which can indeed cause inhibition of tumor growth, does not produce tumor regression. The therapeutic activity measured in all of our studies employed the stringent clinical criterion of tumor regression (i.e., 50% or greater decrease in tumor size). We have done separate experiments (unpublished) demonstrating that weight loss does not cause tumor regression. This fact is also clearly apparent in some of our published studies with ATP-depleting therapy. For example, in a pooled series of six experiments, two groups had similar weight loss (−17% and −19%), but one group had 60% tumor regressions and the other had only 2% tumor regressions. Also, in that same series of experiments, two other groups had identical weight loss (−25%) but different tumor regression rates (60% versus 79%) that were statistically significant. (Weight loss would not be a problem in patients who, unlike animals, can be persuaded to drink and eat, or can be supported intravenously).

ATP Depletion in Tumors with Methylthioadenosine Phosphorylase (MTAP) Deficiency—MTAP, an enzyme involved in purine metabolism, is present in normal tissues, but frequently is deleted (deficient) in leukemias, brain tumors, non-small cell lung cancers, breast cancers, melanomas, pancreatic cancers and sarcomas (76-81 and unpublished results). Methylthioadenosine is produced during polyamine synthesis and cleaved to adenine and 5-methylthioribose-1-phosphate by MTAP. The adenine is reconverted to AMP and then to ATP. The deletion of the MTAP gene in many tumors results in the inability of these cancer cells to salvage adenine; the ATP pools in these cells must be depleted. L-Alanosine, a potent inhibitor of de novo AMP synthesis has demonstrated selective anticancer activity in vitro in MTAP-negative cell lines as compared to MTAP-positive cell lines (81).

An examination of MTAP expression in ten human soft tissue sarcoma cell lines found MTAP not detectable in three of the ten cell lines. These three cell lines were greater than 10-fold more sensitive to L-alanosine than the cell lines containing MTAP. The addition of the de novo purine synthesis inhibitor, MMPR, further enhanced the sensitivity of the cells lacking MTAP activity to L-alanosine. These results provide the basis of selective therapy using L-alanosine+MMPR to treat patients with soft tissue sarcomas, and are another example of the therapeutic utility of the ATP-depleting strategy. In vivo studies of L-alanosine+ MMPR, as well as the addition of 6-AN, are being evaluated (82).

Recognition of Apoptosis As the Mechanism of Cancer Cell Death By Effective Anticancer Therapy—By the 1990's, apoptosis (28), a physiological mechanism for controlled cell deletion that is an energy-dependent, inherent gene-directed program of cell death, sometimes referred to as cell suicide and programmed cell death, was considered the cause of anticancer agent-induced cancer cell death (29-30). Apoptosis and necrosis are considered separate entities, not only morphologically, but mechanistically. It is generally believed that clinically effective anticancer agents, despite having different primary biochemical targets—e.g., DNA damage by topoisomerase inhibitors, microtubule damage by paclitaxel and taxotere, fas antibody ligand binding to a fas cell membrane surface receptor, radiation damage to cell membrane sphingomyelin—all ultimately kill by inducing the biochemical cascades of apoptosis and necrosis (29-30).

In the 1980's, necrosis was considered the mode of cell death induced by DNA-damaging anticancer agents due to the activity of poly (ADP-ribose) polymerase (PARP). PARP is activated by the DNA strand breaks caused by anticancer agents, and cleaves the glycolytic coenzyme, $NAD^+$, leading to formation of poly ADP-ribose moieties. The ensuing depletion of $NAD^+$ inhibits glycolytic generation of ATP with consequent ATP depletion eventuating in necrotic cell death. See FIG. 1. (DNA strand breaks activate PARP which cleaves NAD into PAR moieties. The result is a marked decrease in $NAD^+$ with a consequent fall in ATP until finally there is insufficient ATP to sustain survival of the cell, and cell death by necrosis occurs (PARP=poly (ADP-ribose) polymerase; PAR=poly (ADP-ribose; $NAD^+$=nicotinamide adenine dinucleotide; ATP=adenosine triphosphate.)

The sequential biochemical steps of apoptosis are schematically outlined in FIG. 2. Mitochondria play a central role in apoptosis (31). Anticancer-agent-induced DNA damage effects a fall in the mitochondrial permeability transition ($MPT \downarrow$; 31-32). The MPT fall releases apoptosis-inducing stimuli—Reactive Oxygen species (ROS), Bax, (a pro-apoptotic protein), and $Ca^{2+}$ overload (31-32)—are all factors that facilitate rupture of mitochondria. Mitochondrial rupture releases cytochrome c (cyto c) and procaspase-9 to join with cytosolic Apaf-1 and ATP in an apoptosome leading to the activation of caspase-9 (33-34) Activated caspase-9 then leads to other caspase-caspase interactions that activate caspases-3, -6, -7, and the consequent cleavage of key substrates by the activated caspases (35-36). Caspases, cysteine aspartate proteases, are active in proteolysis, and the result is the dismantling of the cell with the morphology of apoptosis (35-36). Radiation injury to cell membrane sphingomyelin activates the sphingomyelin signaling system to induce apoptosis (37). Ceramide is the second messenger of this pathway and is generated by hydrolysis of plasma membrane sphingomyelin through the action of either a neutral acidic sphingomyelinase (37), or by de novo synthesis via the enzyme ceramide synthase (38). Bcl-2 and Bcl-$x_L$ are anti-apoptotic proteins that protect mitochondria from loss of mitochondrial membrane potential (39-40). The release of caspase-8 (32) by Fas activation leads to direct activation of the caspase system to cleave key substrates, dismantling the cell by apoptosis (35). Caspase-8 can also activate the proapoptotic protein, Bid, that can lead to mitochondrial rupture with activation of the mitochondrial-induced caspase/apoptotic death response system (32, 41). Caspase-3 cleaves PARP, halting the pathway to ATP depletion-induced necrosis via PARP-induced $NAD^+$ depletion (42-43). Thus, the destruction of PARP activity permits caspase activity to complete apoptosis before PARP-induced ATP depletion causes necrotic cell death. (It also should be noted that microtubule drugs induce apoptosis, and that there is evidence that interactions between the mitochondria and the cytoskeleton permit microtubule-active drugs to suppress the closure of the permeability transition pore in tumor mitochondria (44)).

Controversy Over ATP Depletion and Apoptosis—It is 28 years since Kerr et al (in 1972) first outlined the morphological criteria that distinguished cell death by apoptosis from necrosis (28). Many years passed before apoptosis became a biological subject of widespread and great scientific interest. Elucidation of its biochemical mechanism essentially began in the early nineties. Thus, in the late eighties the preclinical therapeutic findings with the MAP program based on enhancing cell death by modulating ATP depletion was still compatible with the existing knowledge that necrosis was the mode of anticancer agent-induced cancer cell death.

However, by the early nineties most clinically effective anticancer agents were considered to kill cancer cells by apoptosis (29-30), and the presence of ATP was considered necessary for apoptosis (46-49). For example, ATP is necessary for conversion of procaspase-9 to activated caspase-9 (34). Thus, the remarkable antitumor effects of MAP attributed to MAP-induced ATP depletion was questioned.

New Facts and New Insights into the ATP-Depletion/Necrosis/Apoptosis Paradox—Although clinically-effective anticancer agents frequently kill cancer cells by activation of the biochemical cascade of apoptosis (29-30), the same anticancer agents can induce cancer cell death by necrosis (40, 56-57). Moreover, these two modes of cell death can occur in different cells simultaneously in tumors and cell cultures exposed to the same agent (40, 56-57). The particular mode of cell death induced after drug treatment is dependent on the drug, its concentration, and the particular cell line (57). Since ATP depletion is the cause of necrosis, whereas ATP is necessary for apoptosis, it is noteworthy that necrotic and apoptotic cell death occur in the same tumor (but in different cells) after anticancer treatment. One reason is that different drug concentrations reach different cancer cells; low concentrations induce apoptosis, and higher concentrations cause necrotic cell death (57). However this is not the only reason.

Since activated caspases execute apoptosis, it is noteworthy that the apoptotic mode of cell death can be prevented by an inhibitor of caspases (e.g., Z-VAD-fmk), but instead of cell survival there is a shift to the necrotic mode of cell death (63-69). The reason is that severe ATP depletion, causative of necrosis, is brought about both by the fall in MPT (36) effecting a cessation of mitochondrial oxidative phosphorylation that generates ATP, as well as the block of caspase-3 by Z-VAD-fmk preventing caspase-3 cleavage of PARP, the result being continued PARP activity leading to NAD+ depletion and consequent ATP depletion.

It is important to note that there are genetic deletions of caspases (60-61), and there are endogenous IAPs (inhibitors of apoptosis), i.e., caspase inhibitors (62). Since apoptosis is governed by activated caspases, genetic loss of caspases or block by IAP of caspase activity, prevents apoptosis. In FIG. 3, caspase inhibition by IAPs plus continued activity by PARP (note in FIG. 3, PARP cleavage by caspase-3 is blocked by an IAP), plus the ATP depletion from the loss of electron transport in ruptured mitochondria, drive the cell to necrosis largely due to continuation of PARP-induced ATP depletion (36, 70). It is believed that the purpose of PARP cleavage is to prevent induction of necrosis during apoptosis and ensure appropriate execution of caspase-mediated apoptosis (70). Failure of PARP cleavage (e.g., by IAP-blocked caspases) would be expected to lead to the increased induction of necrosis but, surprisingly, is also reported to enhance apoptosis (42, 70). FIG. 3's question marks (?) indicate that whether this enhancement is influenced by the continued PARP synthesis of PAR, or by a relationship to the NAD+ level, is not understood (42, 70).

In brief, intracellular ATP levels may determine whether anticancer agent-induced cell death fate is by necrosis or apoptosis (58-59). The activation and action of caspases, before ATP depletion can fall to levels causing cell death by necrosis, allows for caspase-executed apoptosis, and the availability of caspases vs IAPs can dictate the propensity of cells to die from apoptosis vs necrosis. There are many reports of inhibition of caspase activity not conferring a survival advantage because the result is a shift from apoptotic cell death to necrotic cell death (36, 40, 48-49, 56, 58-59, 63-69).

A recent review article on mitochondria and apoptosis (36) states that, "The emergent view is that once cytochrome c is released . . . (by mitochondrial rupture) . . . , this commits the cells to die by either an apoptotic mechanism involving Apaf-1-mediated caspase activation or a slower necrotic process due to collapse of electron transport, which occurs when Cyto C is depleted from mitochondria resulting in a variety of deleterious sequelae including generation of oxygen free radicals and decreased production of ATP."

All the above observations reveal that, rather than functional opposition between the two types of cell death, necrosis and apoptosis, there is a functional cooperativity (FIG. 3). The therapeutic implications are that a tumor's heterogeneous neoplastic cell population likely includes cells with IAPs, gene deletions of certain caspases, and lower levels of Bax. These cancer cells are likely to be of lesser sensitivity to an anticancer agent, and escape death because they do not receive enough damage to reduce ATP to low enough levels insufficient to support cell viability. The insight provided by the findings noted above, and in FIG. 3, suggests that biochemical modulation to further depress ATP to still lower levels than that induced by the anticancer agent alone would kill these sublethally injured cells, augment tumor regressions, and even yield some cures. The preclinical enhanced therapeutic results with MAP+anticancer agents support this thesis.

One new understanding of the paradox in obtaining improved therapeutic results by adding ATP-depleting modulatory treatment to the ATP-requiring apoptotic process is that necrosis and apoptosis are sometimes not completely separate entities in a cancer cell "hit" by an anticancer agent. Both modes of cell death are simultaneously induced by the DNA damage; more specifically, PARP activation as well as mitochondrial damage by a fall in the MPT (FIG. 3). If PARP cleavage occurs by activated caspase-3, necrosis is prevented and apoptosis prevails. If PARP cleavage is prevented by an IAP, necrosis prevails with an assist in ATP depletion from the apoptotically-damaged mitochondria in the ongoing process of necrosis. It is understandable that ATP-depleting modulatory therapy would enhance necrosis and improve the therapeutic results. However, under conditions where PARP activity continues (i.e., PAR synthesis and NAD$^+$ consumption continues), not only is there increased necrosis, but, surprisingly, apoptosis also increases (42, 70). The latter situation (i.e., uncleaved PARP leading to increased apoptosis) is not understood. Perhaps the continued activity of PARP induces changes in the pyridine nucleotide pool (NADH/NAD+NADPH/NADP) and nucleotide pool of ADP and ATP that regulate MPT (68, 71), leading to a fall in the MPT of additional mitochondria that affects rupture of these mitochondria releasing apoptogenic factors that result in increased caspase activity and increased apoptosis. Further research will hopefully explain the ? in FIG. 3. If these conjectures apply, the MAP regimen (i.e., its NAD+ antagonist and ATP) could similarly influence the MPT and increase apoptosis.

ATP Depletion is MAP's Primary Mechanism—Most pertinent to the question of whether the MMPR+6-AN mechanism of enhancing ATP depletion has anything to do with enhancing tumor regressions is the demonstration that MMPR alone can reduce ATP levels to 34% in murine breast tumors, but in combination with 6-AN the ATP level is further reduced to 15% of normal (19). Importantly, this low level of ATP, 15%, cannot sustain cell viability (51-52), and tumor regressions ensue. Also of relevance to ATP depletion and cell death, the combination of MMPR+6-AN has been demonstrated to initiate a significant depletion of ATP prior to the onset of cell death (53).

There is published data (54) comparing both the therapeutic results and the ATP-depleting effect of MAP alone, MAP+FU, MAP+Adriamycin (Adr), and MAP+FU+Adr. ATP depletion becomes more profound in conjunction with increasing levels of tumor-regressing therapeutic activity as treatment is increased from MAP, to MAP+FU or MAP+Adr, to MAP+FU+Adr; the latter levels of ATP depletion and tumor regression rates were significantly lower than that observed in tumors from mice treated with MAP+FU or MAP+Adr (54). Thus, a positive correlation was found between increasing levels of ATP depletion and increasing tumor regression. In other studies (55), both the depletion of ATP by MAP+Adr and tumor regressions were significantly greater than that of MAP alone. Thus, this correlative quantitative data supports ATP depletion as a significant factor in the production of tumor regressions.

The recent reports that blocking activated caspases by exogenous caspase inhibitors (Z-VAD-fmk) (40, 48, 56, 58-59, 63-69), or endogenous inhibitors (IAPs/36), prevents the apoptotic mode of cell death but causes the ATP-depleting form of cell death, necrosis, clearly demonstrate that ATP depletion can be made into a primary effector of cell death. Manipulation of cellular energy metabolism (e.g., inhibition of the mitochondrial respiratory chain or provision or withdrawal of substrates for glycolysis) shifts the balance between apoptosis and necrosis (48). All of these shifts to death by necrosis are physiologic effects due to severe ATP depletion; very low levels of ATP cannot sustain cell viability (51-52).

Taken together, all the above facts are compelling evidence that the enhanced antitumor effects observed in our studies are the result of ATP depletion. Similar therapeutic gains have been obtained by concomitantly administering MAP with nine different DNA-damaging agents which, although they damage DNA by different mechanisms, induce in common the same processes of apoptosis and necrosis which evoke ATP depletion. Hence, sublethally-injured cancer cells due to the DNA-damaging agent will have various degrees of ATP depletion that can be further reduced by MAP to cell-killing levels. It seems clear that ATP depletion is the critical biochemical event common to the cell deaths induced by nine mechanistically-different anticancer agents when given with MAP.

Mechanisms of action other than ATP depletion have been ascribed to MMPR and 6-AN. MMPR, as a single agent, is reported to act as an inhibitor of tumor vascularization, but did not kill cancer cells or cause tumor regression (84). 6-AN, as a single agent, is reported to up-regulate the glucose-regulated stress protein, GRP 78, a finding associated with potentiation of cytotoxicity in vitro of certain anticancer agents; however, the effect of 6-AN on ATP depletion, which is the likely cause of the enhanced cytotoxicity, was not measured (83). Multiple mechanisms of action have been demonstrated for almost all anticancer agents. For example, doxorubicin has had at least nine mechanisms demonstrated, but the interaction with topoisomerase II is nevertheless considered the primary triggering event for cell killing through apoptosis (50). The primary mechanism of action for the enhanced antitumor effect obtained by MAP plus an anticancer agent is clearly severe ATP depletion.

Proposed Clinical Trial of MAP—A proposed clinical trial of MAP has potential for a treatment advance in cancer patient care. Single agent 6-AN has been administered in three Phase I clinical trials in patients with disseminated cancer (72-74), and these studies demonstrated that 6-AN toxicity takes two clinical forms, a low dose mixed B complex vitamin deficiency, and a high dose-dependent CNS toxicity. Of note in the early clinical studies, 6-AN was given daily, whereas the proposed clinical trial for MAP is an infrequent intermittent schedule every 2 weeks; this toxicity should be much less.

It is the preclinically-proven ATP-depleting modulatory concept that requires appropriate clinical exploration, and not specific drugs. Thus, the clinical trial need not necessarily be done with the MAP regimen to prove the therapeutic value of the ATP depletion concept at the clinical level. However, the MAP regimen seems a reasonable first choice, not only for the basic scientific data and reasons already given, and the successful preclinical data with MAP, but because a MAP clinical trial could be completed in a relatively short time. All three of the MAP drugs have been independently evaluated clinically, and therefore, their toxicities and some schedules are known. Cancer patients have received MMPR+PALA combined in a single regimen with a concomitantly administered anticancer drug, 5-fluorouracil (75). Thus, evaluating the MAP regimen in the clinic merely requires integration of 6-AN into the clinically established MMPR+PALA regimen. Clearly, less time would be required for evaluating MAP in the clinic compared to new agents.

Conclusions

1. Preclinical in vivo tumor studies have demonstrated that a combination of ATP-depleting agents (that reduce tumor cell ATP levels to below 15% of normal) administered with anticancer agent therapy markedly enhanced tumor regressions, and can even produce cures.
2. The knowledge of the basic mechanisms effecting necrosis and apoptosis and their interrelationships, the correlation of MAP-induced ATP depletion with MAP-induced tumor regressions, the marked enhancement of preclinical anticancer activity by the concomitant administration of MAP+nine mechanistically different anticancer agents—the total data merits a MAP trial at the clinical level.
3. AT the preclinical level, the therapeutic opportunity opened by modulation of $NAD^+$ and ATP levels merits further research. Other pharmacological manipulations may further improve the MAP regimen.

REFERENCES

1. Berger, N. A., and Berger, S. J. Metabolic consequences of DNA damage: The role of poly (ADP-ribose) polymerase as mediator of the suicide response. In: L. Grossman, A C. Upton, (eds.) Mechanisms of DNA Damage and Repair, pp. 357-363. New York: Plenum Publishing Corporation; 1986.
2. Tanizawa, A., Kubota, M., Hashimoto, H., Shimizu, T., Takimoto, T., Kitoh, T., Akiyama, Y., and Mikama, H. VP-16-induced nucleotide pool changes and poly (ADP-ribose) synthesis: The role of VP-16 in interphase death. Exp. Cell Res. 185:237-246, 1989.
3. Carson, D A., Seto, S., Wasson, B., and Carrera, C. DNA strand breaks, NAD metabolism, programmed cell death. Exp. Cell. Res. 164:273-281, 1986.
4. Schraufstaffer, I. U., Hinshaw, D. B., Hyslop, P. S., Spragg, R. H, and Cochrane, C. G. Oxidant injury of cells DNA stand-breaks activate polyadenosine diphosphate polymerase and lead to depletion of nicotinamide adenine dinucleotide. J. Clin. Invest. 77:1312-1320, 1986.
5. Gaal, J. C., Smith, K. R., and Pearson, C. K.: Cellular euthanasia mediated by a nuclear enzyme: A central role for nuclear ADP-ribosylation in cellular metabolism. Trends Biochem. Sci. 12:129-132, 1987.
6. Marks, D. I., and Fox, R. M. DNA damage, poly(ADP-ribosyl)ation and apoptotic cell death as a potential common pathway of cytotoxic drug action. Biochem. Pharmacol. 42:1859-1867, 1991.
7. Martin, D. S., Biochemical modulation: Perspectives and objectives. In: K. R. Harrap (ed.) New Avenues in Developmental Cancer Chemotherapy, pp. 113-162, Academic Press, London, England, 1986.
8. Dietrich, L. S., Kaplan, L., and Friedland, I. M. Pyridine nucleotide metabolism: mechanism of action of the niacin antagonist, 6-aminonicotinamide. J. Biol. Chem. 233: 964-968, 1958.
9. Varnes, M. E. Inhibition of pentose cycle of A54 cells by 6-aminonicotinamide: consequences for aerobic and hypoxic radiation response and for radiosensitizer action. Natl. Cancer Inst. Monogr., 6:199-202, 1988.
10. Herken, H., Lange, K. and Kolbe, H. Brain disorder induced by pharmacological blockade of the pentose phosphate pathway. Biochem. Biophys. Res. Commun., 36:93-100, 1969.
11. Hunting, D., Gowans, B., and Henderson, J. F. Effects of 6-AN on cell growth, poly (ADP)ribose synthesis and nucleotide metabolism. Biochem. Pharmacol., 34:3999-4003, 1985.
12. Street, J. C., Mahmoud, V., Ballon, D., Alfieri, A. A., and Koutcher, J. A. $^{13}$C and $^{31}$P NMR investigation of effect of 6-aminonicotinamide on metabolism of RIF-1 tumor cells in vitro. J. Biol. Chem. 271:4113-4119, 1996.
13. Koutcher, J. A., Alfieri, A. A., Matei, C., Zakian, K. L., Street, J. C., and Martin, D. S. In vivo $^{31}$P NMR detection of pentose phosphate pathway block and enhancement of radiation sensitivity with 6-aminonicotinamide. Magn. Reson. Med. 36:887-892, 1996.
14. Shantz, G. D., Smith, C. M., Fontenella, L. J., Lau, H. K. F., and Henderson, J. F. Inhibition of purine nucleotide metabolism by 6-methylmercaptopurine ribonucleoside and structurally related compounds. Cancer Res. 33:2867-2871, 1973.
15. Warnick, C. T., and Patterson, A. R. P. Effect of methylthioinosine on nucleoside concentration in L5158 cells. Cancer Res. 33:1711-1715, 1973.
16. Grindey, G. B., Lowe, J. K., Divekey, A. Y., and Hakala M. T. Potentiation by guanine nucleosides of the growth-inhibitory effects of adenosine analogues on L1210 and Sarcoma 180 cells in culture. Cancer Res. 36:379-383, 1976.
17. Martin, D. S., Stofli, R. L., Sawyer, R. C., Spiegelman, S., Casper, E. S., and Young, C. W. Therapeutic utility of utilizing low doses of N-(phosphonacetyl)-L-aspartic acid in combination with 5-Fluorouracil: a murine study with clinical relevance. Cancer Res., 43:2317-2321, 1983.
18. King, M. P., and Attardi, G. Human cells lacking mtDNA: Repopulation with exogenous mitochondria by complementation. Science. 246:500-503, 1989.
19. Martin, D. S., Stolfi, R. L., and Colofiore, J. R. Perspective: The chemotherapeutic relevance of apoptosis and a proposed biochemical cascade for chemotherapeutically-induced apoptosis. Cancer Invest. 15:372-381, 1997.
20. Stolfi, R. L., Colofiore, J. R., Nord, L. D., Koutcher, J. A. and Martin, D. S. Biochemical modulation of tumor cell energy: Regression of advanced spontaneous murine breast tumors with a 5-Fluorouracil containing drug combination. Cancer Res. 52:4074-4981, 1992.
21. Martin, D. S., Stolfi, R. L., Colofiore, J. R., et al: Biochemical modulation of tumor cell energy in vivo. II. A lower dose of adriamycin is required and a greater antitumor activity is induced when cellular energy is depressed. Cancer Invest. 12:296-307, 1994.
22. Stolfi, R. L., Colofiore, J. R, Nord, L. D., and Martin, D. S. Enhanced antitumor activity of an adriamycin+5-fluorouracil combination when preceded by biochemical modulation. Anti-Cancer Drugs 7:100-104, 1996.
23. Koutcher, J. A., Alfieri, A., Stolfi, R. L., Devitt, M. L., Colofiore, J. R., Nord, L. D., and Martin, D. S. Potentiation of a three drug chemotherapy regimen by radiation. Cancer Res. 53:3518-3823, 1993.
24. Martin, D. S., Stolfi, R. L., Colofiore, J. C., et al: Apoptosis resulting from anti-cancer agent activity in vivo is enhanced by biochemical modulation of tumor cell energy. In: Programmed Cell Death. The Cellular and Molecular Biology of Apoptosis, edited by M Lavin, D Walters, New York, Harwood Academic, 1993, pp. 279-296.
25. Martin, D. S., Spriggs, D., and Koutcher, J. A. Aminonicotinamide (6-AN), alone, or in combination with 6-methylmercaptopurine riboside (MMPR) and Pala, markedly enhances cisplatin-induced anticancer activity. Apoptosis, in press.
26. Martin, D. S., Stolfi, R. L., Nord, L. D., Colofiore, J. R. Enhancement of chemotherapeutically-induced apoptosis in vivo by biochemical modulation of poly (ADP-ribose) polymerase. Oncol. Rep. 3:317-322, 1996.
27. Martin, D. S., Stolfi, R. L., Colofiore, J. R. and Nord, L. D. Marked enhancement in vivo of paclitaxel's (taxol's) tumor-regressing activity by ATP-depleting modulation. Anti-Cancer Drugs 7:655-659, 1996.
28. Kerr, J. F. R., Wyllie, A. H. and Currie, A. R. Apoptosis: a basic biological phenomenon with wide-ranging implications in tissue kinetics. Brit. J. Cancer 26:239-257, 1972.
29. Hickman, J. A. Apoptosis induced by anticancer drugs. Cancer Metast. Rev. 11:121-139, 1992.
30. Reed, J. C. Regulation of apoptosis by bcl-2 family proteins and its role in cancer and drug resistance. Curr. Opin. Oncol. 7:541-546, 1995.
31. Kroemer, G, Zamzami, N., and Susin, S. A. Mitochondrial control of apoptosis. Immunol. Today 18:44-51, 1997.
32. Green, D. R. Apoptotic pathways: The roads to ruin. Cell 94:695-698, 1998.

33. Zou, H., Li, Y., Liu, X., and Wang, X. An apaf-1-cytochrome c multimeric complex is a functional apoptosome that activates procaspase-9. J. Biol. Chem. 274: 11549-11556, 1999.
34. Liu, X., Kim, C. N., Yang, J., Jemmerson, R., and Wang, X. Induction of apoptotic program in cell-free extracts: requirement for dATP and cytochrome C. Cell 86:147-157, 1996.
35. Schmitt, E., Sane, A. T., and Bertrand, R. Activation and role of caspases in chemotherapy-induced apoptosis. Drug Resistance Updates 2:21-29, 1999.
36. Green D R and Reed J C. Mitochondria and apoptosis. Science 281:1309-1312, 1998.
37. Haimovitz-Friedman, A., Kan, C. C., Ehleiter, D., Persaud, R. S., McLoughlin, M., Fuks, Z., and Kolesnick, R. N. Ionizing radiation acts on cellular membranes to generate ceramide and initiate apoptosis. J. Exp. Med. 180: 525-535, 1994.
38. Bose, R., Verheij, M., Haimovitz-Friedman, A., Scotto, K., Fuks, Z., and Kolesnick, R. Ceramide synthase mediates daunorubicin-induced apoptosis: an alternative mechanism for generating death signals. Cell 82:405-411, 1995.
39. Susin, S. A., Zamzami, N., Castedo, M., Hirsch, T., Marchetti, P., Macho, A., Dauges, E., Gauskens, M. and Kroemer, G. Bcl-2 inhibits the mitochondrial release of an apoptogenic protease. J. Exp. Med. 184:1331-1342, 1996.
40. Shimizu, S., Equchi, V., Kamike, W., Itoh, Y., Hasegawa, J., Yamabe, K., Otsuid Y., Matsuda, H., and Tsujimoto, Y. Induction of apoptosis as well as necrosis by hypoxia and predominant prevention of apoptosis by bcl-2 and bcl-x. Cancer Res. 56:2161-2166, 1997.
41. Li, H., Zhu, H., Xu, C. J. Cleavage of BID by caspase 8 mediates the mitochondrial damage in the Fas pathway of apoptosis. Cell 94:491-501, 1998.
42. Boulares, A. H., Yokovlev, A. G., Ivanova, V., Stoica, B. A., Wang, G., Iyer, S., and Smulson, M. Role of poly (ADP-ribose) polymerase (PARP) cleavage in apoptosis. Caspase-3 resistant PARP mutant increases rates of apoptosis in transfected cells. J. Biol. Chem. 274:22932-22940, 1999.
43. Janicke, R. V., Sprengart, M. L., Wati, M. R., and Porter, A. G. Caspase-3 is required for DNA fragmentation and morphological changes associated with apoptosis. J. Biol. Chem. 273:9357-9360, 1998.
44. Evtodienko, Y. V., Teplova, V. V., Sidosh, S. S., Ichas, F., and Mazal, J. P. Microtubule-active drugs suppress the closure of the permeability transition pore in tumor mitochondria. FEBS Lett. 393:86-88, 1996.
45. Martin, D. S. Purine and pyrimidine biochemistry, and some relevant clinical and preclinical cancer chemotherapy research. In: G. Powis, R A. Prough, (eds.) Metabolism and action of Anti-cancer Drugs, pp 91-140, London: Talyor & Francis 1987.
46. Cotter, T. G., Lenon, S. V., Glynn, J. G., and Martin, S. J. Cell death via apoptosis and its relationship to growth, development and differentiation of both tumor and normal cells. Anticancer Res. 10:1153-1160, 1990.
47. Wyllie, A. H. Apoptosis [The 1992 Frank Rose Memorial Lecture]. Br. J. Cancer 67:205-208, 1993.
48. Nicotera, P., and Leist, M. Energy supply and the shape of death in neurons and lymphoid cells. Cell Death Differ. 4:435-442, 1997.
49. Nicotera, P., and Leist, M. Mitochondrial signals and energy requirement in cell death. Cell Death Differ. 4:516, 1997.
50. Gerwirtz, D. A. A critical evaluation of mechanisms of action proposed for the antitumor effects of the anthracycline antibiotics adriamycin and daunorubicin. Biochem. Pharm. 57:727-741, 1999.
51. Nieminen, A. L., Saylor, A., Herman, B., and Lemasters, J. J. ATP depletion rather than mitochondrial depolarization mediates hepatocyte killing after metabolic inhibition. Am. J. Physiol. 267 (Cell Physiol. 36): C67-C74, 1994.
52. Sweet, S., and Singh, G. Accumulation of human promyelocytic leukemic (HL-60) cells at two energetic cell cycle checkpoints. Cancer Res. 55:5164-5167, 1995.
53. Nord, L. D., Stolfi, R. L., Alfieri, A. A., Netto, G., Reuter, V., Sternberg, S. S., Colofiore J R, Koutcher J A, and Martin D S. Apoptosis induced in advanced $CD_8F_1$-murine mammary tumors by the combination of PALA, MMPR and 6-AN precedes tumor regression and is preceded by ATP depletion. Cancer Chemother. Pharmacol. 40: 376-384, 1997.
54. Colofiore, J. R., Stolfi, R. L., Nord, L. D., Martin, D. S. On the relationship of ATP depletion to chemotherapeutically-induced tumor regression. Int. J. Oncol. 7:1401-1404, 1995
55. Colofiore, J. R., Stolfi, R. L., Nord, L. D., and Martin, D. S. Biochemical modulation of tumor cell energy IV. Evidence for the contribution of adenosine triphosphate (ATP) depletion to chemotherapeutically-induced tumor regression. Biochem. Pharm. 50:1943-1948, 1995.
56. Amarante-Mendes, G. P., Finucane, D. M., Martin, S. J., Cotter, T. G, Salvesen, G. S., and Green, D. R. Anti-apoptotic oncogenes prevent caspase-dependent and independent commitment for cell death. Cell Death Differ. 5:298-306, 1998.
57. Huschtscha, L. I., Andersson, C. E., Bartier, W. A., and Tattersall, M. H. N. Anti-cancer drugs and apoptosis. In: Programmed cell death, the cellular and molecular biology of apoptosis, Ed: M. Lavin and D. Walters, New York, Harwood Academic, 1993, pp 269-278.
58. Eguchi, Y., Shimizu, S., and Tsujimoto, Y. Intracellular ATP levels determine cell fate by apoptosis or necrosis. Cancer Res. 57:1835-1840, 1997.
59. Leist, M., Single, B., Castoldi, A. F., Kuknle, S., and Nicotera, P. Intracellular triphosphate (ATP) concentration: a switch in the decision between apoptosis and necrosis. J. Exp. Med. 185: 1481-1486, 1997.
60. Kuida, K., Hayder, T. F., Kuan, C. Y, Gu, Y., Taya, C, Karasuyama, H., Su, M. S. S., Radic, P., and Flavell, R. A. Reduced apoptosis and cytochrome c-mediated caspase activation in mice lacking caspase activation in mice lacking caspase 9. Cell 94:325-337, 1998.
61. Yoshida, H., Kong, Y. Y., Yoshida, R., Elia, A. J., Hakem, R., Penninger, J. M., and Mak, T. W. Apaf-1 is required for mitochondrial pathways of apoptosis and brain development. Cell 94:739-750, 1998.
62. Roy, N., Dveraux, Q. L., Takahashi, R., Salvesen, G. S., and Reed, J. C. The c-IAP-1 and c-IAP-2 proteins are direct inhibitors of specific caspases. EMBO J. 16:6914-6925, 1997.
63. Sane, A. T., and Bertrand, R. Caspase inhibition in camptothecin-treated U-937 cells is completed with a shift from apoptosis to transient G, arrest followed by necrotic cell death. Cancer Res. 59:3565-3569, 1999.
64. Lemaire, C., Andreau, K., Souvannavong, K., and Adam, A. Inhibition of caspase activity induces a switch from apoptosis to necrosis. FEBS Lett. 425:266-270, 1998.
65. Cappola, S., Nosseri, C., Maresco, V., and Ghibelli, L. Different basal NAD Levels determine opposite effects of poly (ADP-ribosyl) polymerase inhibitors on $H_2O_2$-induced apoptosis. Exp Cell Res 221:462-469, 1995.
66. Kiang, J., Chao, T., and Korsmyer, S. J. Bax-induced cell death may not require interleukin 1-converting enzyme-like proteases. Proc Natl Acad Sci USA 93: 143559-14563, 1996.
67. Shimizu, S., Equchi, Y., Kamuke, W., Waguri, S., Vchiyama, Y., Matsuda, H., and Tsujimoto, Y. Bcl-2 blocks loss of mitochondrial membrane potential with ICE inhibitors act at a different step during inhibition of death induced by respiratory chain inhibitors. Oncogene 13:21-29, 1996.
68. Hirsch, T., Marchetti, P., Susin, S., Dellaporta, B., Zamzami, N., Marzo, I., Geuskens, M., and Kroemer, G. The apoptosis-necrosis paradox. Apoptogenic proteases activated after mitochondrial permeability transition determine the mode of cell death. Oncogene 15:1573-1581, 1997.
69. Mehmet, H., Yue, X., Penrice, J., Cady, E., Wyatt, J. S., Surraf, C., Squier, M, and Edwards, A. D. Relation of impaired energy metabolism to apoptosis and necrosis following transient cerebral hypoxia-ischemia. Cell Death Differ 5:321-329, 1998.
70. Herceg, Z., and Wang, Z. Q. Failure of poly (ADP-ribose) polymerase cleavage by caspases leads to induction of necrosis and enhanced apoptosis. Mol Cell Biol 19:(7):5124-33, 1999.
71. Constantini, P., Chernyak, B. V., Petronilli, V., and Bernardi, P. Modulation of the mitochondrial permeability transition pore by pyridine nucleotides and dithiol oxidation at two separate sites. J Biol Chem 271:6746-6751, 1996.
72. Taylor, S. G., Korman, S, Shy-Peck, H. H., et al. 6-Aminonicotinamide in disseminated human cancer. Lab and Clin Med, p. 950, December 1958.
73. Herter, F., Weissman, S. G., Thompson, H. G., et al. Clinical experience with 6-aminonicotinamide. Cancer Res 21:31-37, 1961.
74. Perlia, C. P., Koffman, S., Sky-Peck, H., et al. Clinical use of 6-aminonicotinamide in patients with disseminated neoplastic disease. Cancer Res 14:644-648, 1961.
75. O'Dwyer, P. J., Hudas, G. R., Colofiore, J., Walczak, J., Hoffman, J., La Creta, F. P., Comis, R. L., Martin, D. S., and Ozols, R. F. Phase I trial of fluorouracil modulation by N-phosphonacetyl-Laspartate and 6-methylmercaptopurine riboside: Optimization of 6-methylmercaptopurine dose and schedule through biochemical analysis of sequential tumor biopsy specimens. J Natl Cancer Inst 83:1235-1240, 1991.
76. Kamatani, N., Nelson-Rees, W. A., and Carson, D. A. Selective killing of human malignant cell lines deficient in methylthioadenosine phosphorylase, a purine metabolic enzyme. Proc. Natl. Acad. Sci. USA, 78:1219-1223, 1981.
77. Fitchen, J. H., Riscoe, M. K., Dana, B. W., Lawrence, H. J., and Ferro, A. J. Methylthioadenosine phosphorylase deficiency in human leukemias and solid tumors. Cancer Res., 46:5409-5412, 1986.
78. Nobori T, Karras J G, Della Ragione F, Waltz T Z, Chen P P, and Carson D A. Absence of methylthioadenosine phosphorylase in human gliomas. Cancer Res., 51:3193-3197, 1991.
79. Nobori, T., Szinai, I., Amox, D., Parker, B., Olopade, O. I., Buchhagen D L, and Carson D A. Methylthioadenosine phosphorylase deficiency in human non-small cell lung cancers. Cancer Res. 53:1098-1101, 1993.
80. Chen, Z. H., Zhang, H., and Savarese, T. M. Gene deletion chemoselectivity: codeletion of the genes for $p16^{INK4}$, methylthioadenosine phosphorylase, and the _- and _-interferons in human pancreatic cell carcinoma lines and its implications for chemotherapy. Cancer Res., 56:1083-1090, 1996.
81. Batova, A., Diccianni, M. B., Omura, Minamisawa, M., Yu, J., Carrera, C. J., Bridgeman, L. J., Kung, F. H., Pullen, J., Amyulon, M. D., and Yu, A. L. Use of alanosine as a methyladenosine phosphorylase—selective therapy for T-cell acute lymphoblastic leukemia in vitro. Cancer Res. 59:1492-1497, 1999.
82. Li, W. W., Cole, P., Martin, D., Banerjee, D., and Bertino, J. R. Methylthioadenosine phosphorylase (MTAP) status determines sensitivity to L-alanosine in human soft tissue sarcoma cell lines and is enhanced by 6-methylmercaptopurine riboside (MMPR). Proc. AACR (Abstract), to be presented, Apr. 1-5, 2000.
83. Chatterjee, S., Hirota, H., Belfi, C. A., Berger, S. J., and Berger, N. A. Hypersensitivity to DNA cross-linking agents associated with up-regulation of glucose-regulaed stress protein GRP 78. Cancer Res. 57:5112-5116, 1997.
84. Presto, M., Rusunati, M., Belleri, M., Morbedelli, L., Ziche, M., and Ribatti, D. Purine analog 6-methylmercaptopurine riboside inhibits early and late phases of the angiogenesis process. Cancer Res. 59:2417-2424, 1999.
85. Martin, D. S. Cancer chemotherapy: Past is prologue. Mt. Sinai. J. Med. 52:426-434, 1985.
86. Stolfi, R. L., Martin, D. S. and Fugman, R. A. Spontaneous murine mammary adecocarcinoma: Model system for the evaluation of combined methods of therapy. Cancer Chemother. Rep. Part !, 55:239, 1971.
87. Martin, D. S., Fugman, R. A., Stolfi, R. L. and Hayworth, .E. Solid tumor animal model therapeutically predictive for human breast cancer. Cancer Chemother. Rep. Part 2, 5:89, 1975.
88. Goldin, A., Kendetti, J. M., MacDonald, J. S. Mugggia, F., Henney, J. and DeVita, V. T. Current results of the screening program at the Division of Cancer Treatment, National Cancer Institute, Eur. J. Cancer 17:129, 1981.

Second Series of Experiments

Most anticancer agents (e.g., cisplatin; (1) effect cancer cell deaths as a consequence of interaction with DNA. As with all DNA-damaging agents the mode of cell death is then by necrosis or apoptosis. Importantly, whether these cell deaths—i.e. tumor regressions-can be enhanced or not is determined by intracellular ATP levels (2, 3). The latter intelligence is reviewed to facilitate an understanding of the great potential of an ATP-deleting strategy to improve cancer treatment.

DNA-damaging agents can kill cancer cells by either necrosis or apoptosis (2-6). Severe ATP depletion causes necrosis (2-7), whereas ATP is necessary for the initiation and progression of apoptosis induced by a DNA-damaging agent (8-12). For example, ATP is necessary for the activation of caspase-9 (8), and for chromatin condensation (9) in apoptosis. Despite this disparity in ATP needs—ATP depletion for necrosis and an ATP requirement for apoptosis—these two modes of cell death can occur simultaneously in tumors exposed to the same agent (2 6, 10, 12, 13). One reason is that the intensity of the primary drug-target interaction decides the prevalence of either apoptosis or necrosis. Low concentrations of drug induce apoptosis and higher concentrations necrosis (6, 10, 12, 13). Due to the distorted pathological architecture of a tumor in vivo, different concentrations of an anticancer agent reach different individual cells in different regions of the tumor. Thus, both necrotic and apoptotic dead cells are found in the same tumor treated by the same anticancer agent. The uneven "playing field" in vivo also explains why some cells are only slightly "hit" (i.e., only sublethally depleted of ATP), and therefore recover, and, hence, concomitant ATP-depleting treatment can "push" these cells to necrotic death.

There are other important reasons for the finding of both necrotic and apoptotic modes of cell death following DNA-damaging therapy. A DNA-damaging drug (such as cisplatin) activates the necrosis pathway concomitantly with the apoptosis pathway. In the necrosis pathway, DNA strand breaks activate a DNA repair enzyme, poly (ADP-ribose) polymerase (PARP), to cleave (i.e. destroy) NAD+ to form poly (ADP-ribose) moieties to temporarily link DNA strand breaks together to facilitate permanent DNA repair. Hyperstimulation of PARP as a consequence of overwhelming DNA damage (e.g., by a high dose of agent) causes rapid depletion of NAD+ pools, ultimately inhibiting glycolysis and thereby the glycolytic generation of ATP, causing a severe ATP depletion that effects cell death by necrosis (14-19) before caspases can effect apoptosis.

The apoptosis pathway is concomitantly activated along with the necrosis pathway in the same cells because the same DNA damage also induces mitochondrial injury that leads to mitochondrial rupture with consequent release of apoptogenic proteins that activate the caspase cascade to execute apoptotic cell death (8, 20-23). Caspases are proteolytic enzymes that dismantle the cell to the morphology of apoptosis (11). one of the caspases, caspase-3, cleaves PARP, destroying it, and thereby halts the PARP-induced NAD+ ATP-depleting necrosis pathway (24, 25). This destruction of PARP activity permits caspase activity to complete apoptotic cell death by preventing PARP-induced ATP depletion in that cell.

The above events occur under "normal" conditions; i.e., when no other factors are involved. The necrosis and apoptosis-inducing pathways are not completely isolated entities. There is an important "connection" between the two cell death modes at the level of ATP depletion.

The ATP-depleting "connection" was exposed by experiments in which the apoptotic mode of cell death was prevented by adminstration of an exogenous inhibitor of caspases, Z-VAD.fmk. Instead of the expected prevention of cell death, there was a shift from the apoptotic to the necrotic mode of cell death. The Z-VAD-fmk block to caspase activity allowed the necrotic pathway to continue because caspase cleavage of PARP was prevented and, therefore, PARP-induced ATP depletion continued to necrosis. Also, the Z-VAD-fmk inhibition of all caspase activity prevented completion of apoptosis, but allowed the ATP depletion due to the mitochondrial damage to continue. The unexpected result was a severe ATP depletion with a shift from the apoptotic to the necrotic mode of cell death (10, 12, 13, 26-28). Thus, despite the initiation of apoptosis, in the absence of caspase activity the cell dies a necrotic death.

There are natural intracellular factors that can bring about the same absence of caspase activity. Some cells may have genetic deletion of certain caspases (24, 29). Other cells may have endogenous inhibitors of apoptosis, IAPS, that inhibit caspases (30). Genetic deletion of caspases inhibits apoptosis (29, 31), as does the presence of the caspase inhibitors, the IAPs (32). Thus, there are natural intracellular conditions-namely, absent or blocked caspase activity due to genetic deletion or IAPs-that shift an anticancer agent-induced death mechanism to necrosis in such apoptosis-compromised cells.

Clearly, ATP depletion induced by DNA-damaging agents is an important cause of cell death. The heterogeneity of the neoplastic cell population may include cells with IAPs and genetic deletions of caspases. The heterogeneity must also embrace cells of lesser sensitivity to the anticancer agent. We hypothesize that these less sensitive cells escape anticancer agent-death because they do not received enough damage to reduce ATP to low enough levels to kill. It was further hypothesized that concurrent biochemical modulation of ATP to further depress the reduced intracellular ATP pool to still lower levels than that induced by the anticancer agent, should kill these cells, and markedly enhance the tumor regressions produced by the anticancer agent.

To enhance treatment-induced cancer cell kill by ATP depletion, we employed the biochemical modulatory regimen of 6-methylmercaptopurine ribose+6-aminonicotinamide+PALA, or MMPR+AN+PALA (referred to as MAP; in previous publications, a different acronym, PMA, was employed for the same three drugs in combination). The reasons for the selection of each component of MAP are discussed later but MAPIs primary mechanism of action, ATP depletion, is entirely due to MMPR+6-AN. MAP has markedly enhanced the preclinical tumor regression rates of many classic anticancer agents, including doxorubicin, taxol, 5-fluorouacil, phenylalanine mustard, cyclophosphamide, mitomycin, etoposide, and radiotherapy (33-40). In this review, unpublished efficacy and toxicity findings with still another mechanistically diverse anticancer agent, cisplatin (DDP), in combination with 6-AN alone and with MAP, is presented to illustrate (without need to search for the latter references) the potential of adjuvant ATP depletion to improve cancer treatment. The materials and methods employed in these DDP studies are detailed in the latter references.

Table 2 evaluates Saline-treated controls (Group 1), 6-AN (Group 2) and DDP (Group 3) as single agents, and in combination (Group 4), against 1st generation subcutaneous solid tumor transplants of advanced CD8F, spontaneous breast tumors. In the same experiment (i.e., same tumor transplants), is a group adding 6-AN to PALA and MMPR (MAP, Group 5), as well as a group with MAP administered prior to DDP (Group 6). Note that the schedule is intermittent and relatively infrequent (i.e., every 10-11 days), and, as a result, some treatments (Group 1, Saline-treated, and Group2, 6-AN-treated) are relatively ineffectual, and the tumors grow and kill their hosts (5/10 deaths in the saline treated Group I and 3/10 deaths in 6-AN-treated Group2). DDP alone (Group 3), and particularly the combination of 6-AN and DDP (Group 4), are more effective in anticancer activity, but their adverse effects are limited to inhibition of tumor growth. In contrast, the more effective ATP-depleting MAP treatment alone (Group 5) effects tumor regressions (20% PR, 2/10). The combination of MAP and DDP (Group 6) is still more effective, producing tumor regressions (i.e. reducing the average tumor size from 80 mgs when treatment was initiated to an average of 39 mg one month later after only three highly intermittent courses of therapy), and yielding a significant PR rate of 60% (6/10).

Note that there is a scheduling interval between the administration of 6-AN and DDP as well as MAP when combined with DDP. We have evaluated simultaneous and varying scheduling intervals up to 7½ hours, and found the interval of 2½ hours best. The timely prior administration of 6-AN before DDP enhances the therapeutic index.

Also note that the DDP dose of 7 mg/kg (the MTD in this 10-11 day schedule in CD8F$_1$ tumor-bearing animals) is reduced to only 4-5 mg/kg when combined with MAP.

The weight loss is due to anorexia induced by MAP; there is little histological evidence of tissue damage after MAP. The animals stop eating and drinking for 3-4 days after MAP (a long period without sustenance for small animals with a high BMR). This degree of anorexia should not be a problem at the clinical level. While severe weight loss can cause inhibition of tumor growth, weight loss per se never causes tumor regression. Thus, the 60% PR rate is a selective effect of the combination of MAP and DDP.

TABLE 2

Chemotherapeutic effect of the addition of cisplatin (DDP) to ATP-Depleting Therapy in first passage CD8F$_1$ advanced spontaneous breast tumors.[a]

| Group & Treatment[b] | Av. Tumor W't (mg) | Regressions/ Survivors[d] | Dead/Total[c] | % Weight Change |
|---|---|---|---|---|
| 1. Saline | 4,469 | 0/5 | 5/10 | +7 |
| 2. 6-AN$_{15}$ | 1,765 | 0/7 | 3/10 | +6 |
| 3. DDP$_7$ | 850 | 0/9 | 1/10 | −18 |
| 4. 6-AN$_{10}$- 2.5 hr->DDP$_7$ | 380 | 0/10 | 0/10 | −19 |
| 5. MAP | 265 | 2/10 | 1/10/ | +4 |
| 6. MAP-2.5 hr->DDP$_5$ | 39 | 6/10 | 0/10 | −15 |

[a]Exp.3069F. Tumors averaged 80 mg when treatment initiated.
[b]The indicated treatment was administered in three courses with a 10-day interval between the first and second courses and an 11 day interval between the second and third courses. Subscripts refer to doses in mg/kg. All doses are i.p., and are MTD for the 10-11 day schedule. MAP = PALA$_{100}$-17 hr-->MMPR$_{150}$ (6-methylmercaptopurine riboside) + 6-AN$_{10}$0 (6-Aminonicotinamide)
[c]Toxicity and therapeutic observations were recorded after the third course of treatment.
[d]regressions = partial tumor regressions (<50% tumor size when treatment initiated).

Table 3 presents the pooled tumor regression results of five separate experiments in animals bearing advanced 1st passage CD8F$_1$ spontaneous breast tumors. Without mortality, and despite receiving only three highly intermittent (10-11 day schedule) courses of MAP+DDP treatment, the MAP tumor regression rate of 24% was more than doubled to 54%.

TABLE 3

Chemotherapeutic effects of the addition of cisplatin (DDP) to MAP in first passage CD8F$_1$ advanced spontaneous breast tumors[a]

| Treatment[b] | Dead/Total[c] | Regressions/Survivors[c] |
|---|---|---|
| 1. MAP | 1/50 | 12PR/49 (24%) p < 0.01 |
| 2. MAP-2.5 hr->DDP$_4$ | 0/50 | 28PR/50 (54%) |

[a]Pooled results. Exp. 2489F, 2583F, 2616F, 3069F, 3076. Tumors averaged 100 mg when treatment was initiated.
[b]The indicated treatment was administered in three courses with a 10 day interval between the first and second courses and an 11 day interval between the second and third courses.
[c]Toxicity and therapeutic observations were recorded one week after the third course of treatment.

Our specific modulatory drug regimen to further reduce intracellular ATP was selected for the following reasons. Glycolysis, the intracellular conversion of glucose to pyruvate, is the only metabolic pathway that provides the cell with ATP in the absence of oxygen, and it has been shown that cancer cell lines with impaired mitochondrial function rely on glycolysis for their energy needs (41). Accordingly, 6-aminonicotinamide (6-AN), an inhibitor of the NAD-dependent enzyme, 6-phosphogluconate dehydrogenase, in the pentose phosphate pathway and thereby of the glycolytic generation of ATP (42), was administered concomitantly with apoptosis-inducing anticancer agents (33, 43-45). Thus, the two major pathways for the intracellular generation of ATP, mitochondrial oxidative phosphorylation (damaged by the anticancer agent) and glycolysis by 6-AN, are concomitantly inhibited (e.g., 6-AN+DDP).

Intracellular supplies of adenine produced by intracellular de novo and salvage pathway biosynthesis of purines (as well as by polyamine catabolism) is necessary for production and maintenance of ATP. Therefore, 6-methylmercaptopurine riboside, MMPR, a purine analog known to markedly inhibit purine biosynthesis (46-49) was administered concomitantly with the other two ATP-depleting agents; i.e., MMPR+6-AN+an apoptosis-inducing anticancer agent (e.g., DDP). Importantly, even without the ATP-depleting contribution of an apoptosis-inducing anticancer agent, the combination of just MMPR+6-AN has been shown to effect severe lowering of tumor ATP levels in tumor-bearing animals; specifically, 15% of normal 48 hrs after administration (50), along with tumor regressions (33, 43-45, 49). Moreover, NMR spectra, obtained from 1st passage breast tumors pre- and post-treatment with PALA+MMPR+6-AN demonstrated that both PCr/Pi and NTP/Pi ratios were decreased after treatment with the 3-drug combination, a finding clearly indicative of energy depletion (33).

ATP is not the only metabolite lowered as a result of the mitochondrial damage that occurs due to the anticancer agent-induced apoptotic biochemical cascade. Pyrimidine de novo synthesis is functionally linked to the respiratory chain in the inner mitochondrial membrane by membrane-bound dihydroorotate dehydrogenase (51), the fourth enzyme of de novo pyrimidine synthesis. Therefore, anticancer agent-induced mitochondrial damage should decrease de novo pyrimidine biosynthesis sufficiently to marginally limit pyrimidines. It has been shown that cells which had been completely depleted of mitochondria had become pyrimidine auxotrophs because of the deficiency of the respiratory-chain dependent dihydroorate dehydrogenase (41). To further decrease any limited reduction of pyrimidine levels by the mitochondrial damage effected by an anticancer agent-induced apoptotic biochemical cascade, PALA (N-phosphonoacetyl-L-aspartate) was added to the combination of MMPR+6+AN. The addition of PALA to MMPR+6-AN (at a dose that is biochemically active in reducing pyrimidine levels but not antitumor active when PALA is employed as a single agent) has been shown to effect significantly greater numbers of tumor regressions than MMPR+6-AN (52, 53).

Necrotic cell death is due to very low levels of ATP (2-7). These low levels of ATP must be in the range of 15% of normal or below, before cells lose viability (7, 54). Tumor growth, cellular proliferation requires ATP at a minimal level (54). Thus, if ATP does not fall to the severely low range of 15% or below, say only to 75%, there will be only tumor growth inhibition. Our previously published biochemical data in the same tumor model, and with the same dose of 6-AN (10 mg/kg) that is administered with DDP (Group 4) in Table 2, only reduced tumor ATP levels to 75% of normal (33), a level compatible with the finding of only tumor growth inhibition by the 6-AN+DDP combination in Table 2. In contrast, the tumor's ATP measurements following a single course of MAP treatment were 32% and 15% of normal at 24 and 48 hours, respectively (50). The latter levels are severely low cell-killing levels of ATP that are compatible with the enhanced cancer cell deaths (i.e. 60% tumor regressions) obtained with MAP+DDP (Group 6) in Table 2. The five experiments in Table 3 averaged a 54% tumor regression rate with 6-AN+DDP.

In a different tumor model, Budihardjo et al found that the above single dose of 6-AN alone, at 10 mg/kg, also reduced the tumor ATP levels to approximately 75-80% of normal (1). However, their 6-AN (10 mg/kg) schedules in vivo (q 3 hours×3 on days 1,3,5 or continuous infusion) were too toxic. Although their in vitro studies demonstrated enhanced efficacy of 6-AN+DDP, the toxicity of their in vivo schedules precluded further testing for in vivo efficacy in tumor-bearing mice (1). They did not evaluate MAP, or our 10-11 day intermittent schedule with 6-AN alone or 6-AN+DDP.

In our initial studies with the MAP combination, MAP was administered at 7-day intervals. More experience demonstrated that it is less toxic (i.e. only weight loss and essentially no mortalities) when the interval between courses is extended from 7 days to 10 or 11 days. Moreover, this change in the schedule of administration permitted the safe addition of other anticancer agents together with MAP (33-40). The relatively lengthy recovery periods (10-11 days) between intermittent treatments has allowed 6-AN alone at really high (16 mg/kg) dosage to be safely administered with radiotherapy, and to markedly enhance radiotherapy-induced tumor regressions (39). It appears that different schedules explain the 6-AN toxicity obtained in vivo by Budihardjo et al (1).

6-AN was abandoned after clinical trial in the early 1960's because of a lack of efficacy as a single agent. However, at that time, the daily administration of anticancer agents was in vogue. 6-AN was administered on a daily schedule that resulted in a cumulative toxicity of nictinamide deficiency that could be reversed merely by stopping treatment with 6-AN or by administering the antidote, nicotinamide (55). Today, the intermittent administration of anticancer drugs has proven practical utility in cancer treatment. As an intermittently administered biochemical modulator (i.e. once every 10-11 days), 6-AN should not produce signs of nicotinamide deficiency. In the present preclinical studies, an intermittent (once every 10-11 days) schedule rather than a daily administration schedule of 6-AN was employed successfully. In the early clinical trials it had been determined that a dose of 6-AN of 0.2 mg/kg/day for up to 28 consecutive days of treatment was safe (55). Using the equivalent surface area dosage conversion factor (56), this human dose was found to be equivalent to a cumulative dose of 24 mg/kg over 10 days in the mouse. Therefore, our intermittent low dose schedule(10 mg/kg every 10-11 days) is calculated to be less than half of the safe cumulative human equivalent dose of 6-AN every 10 days. The toxicity identified when 6-AN was administered on a daily schedule in early clinical studies should not impede the current clinical development of this agent in a therapeutic drug combination proven preclinically safe in an intermittent administration schedule.

Both the modest and severe levels of ATP depletion noted above effected preclinical anticancer activity. However, there is an important difference at the clinical level between tumor growth inhibition and tumor regression. Only tumor regressions, and not tumor inhibition, can be measured clinically. Therefore, evaluation of an ATP-depleting agent(s) at the clinical level should seek to achieve a severe degree of ATP depletion (>85%) in the cancer cells. Biochemically active high dosage administration that is safe due to appropriate periods of rest between injections should be built into the clinical protocol. The choice of clinical dosage should be scientifically determined. 6-AN for example, is known to effect its damage by block of 6-phosphogluconate dehydrogenase, and this parameter can be measured, either non-invasively by NMR, or in sequential biopsies of tumor tissue by biochemical assay. The known quantitative biochemical differences between mouse and man indicate that the interval between administration of agents will likely be different in the two species. In order to translate successful preclinical results in biochemical modulation into the clinic, it will be best to determine in patients (by direct biochemical measurements at the tissue level in Phase I studies only) the dose and temporal relationships between agents that produces the pertinent biochemical changes in human tumors that were associated with the therapeutic success of that particular drug combination in the murine tumor model.

Therapeutic activity has been measured in these studies using a stringent clinical criterion of tumor regression (i.e., 50% or greater drug-induced decrease in tumor size), rather than the more conventional animal model criteria of tumor growth inhibition. It should also be noted that the spontaneous, autochthonous, CD8F1 breast tumor model (57) has demonstrated a remarkable correlation with human breast cancer in terms of both positive and negative sensitivity to individual chemotheraoeutic drugs, using tumor regression as the criterion for evaluation (56). Viewed against the entire background of findings, it would appear reasonable to consider this drug combination for clinical evaluation.

Despite the impressive anticancer results (enhanced tumor regression and some cures) in vivo, the concept of combining ATP-depleting agents with anticancer agents considered to induce cancer cell deaths by apoptosis, a mode of cell death requiring ATP, has been controversial and viewed as a paradox. Apoptosis, although made known 28 years ago, did not have its exciting significance to biology and medicine became widely recognized until the early nineties, and then it pushed necrosis aside. An understanding of the interrelated ATP-depleting necrosis and ATP-requiring caspase-activating apoptosis cell death response systems have come slowly. However, there is now new insight. A late nineties article (32) states, "The emergent view is that once cytochrome c is released, this commits the cell to die by either a rapid apoptotic mechanism involving Apaf-1-mediated caspase activation or a slower necrotic process due to collapse of electron transport which occurs when cyto c is depleted from mitochondria, resulting in . . . decreased production of ATP".

Moreover, the late nineties have seen many reports of inhibition of caspase activity not conferring a survival advantage because the result is a shift from apoptotic cell death to necrotic cell death (1-13, 26-28). These recent facts provide insights to clarify the apparent paradox noted above, and, this understanding should enable consideration of the ATP-depleting strategy, and a MAP clinical trial.

Significance: ATP production has long been a target for drug development in cancer. Over the years many agents have been suggested but none have received general acceptance for clinical treatment. The usual preclinical concept is simple. Since energy is important for cellular function, limiting it will injure the cell, and particularly by inhibiting DNA repair following DNA damage induced by an anticancer agent. The critical determinants of success in preclinical studies are not identified, and hence the choice of these parameters are left to arbitrary decision for clinical trial, the results of which have been disappointing.

The concept proposed here differs in being scientifically based on the knowledge of the relationship of ATP depletion to the cell death induced by an anticancer agent, whether that death is by necrosis or apoptosis. This concept is the first to recognize that anticancer agents initiate ATP depletion by inducing the necrosis and apoptosis pathways of cell death in their sublethally-affected cells, and that this therapy-induced ATP depletion creates a therapeutic opportunity for enhancing treatment. It is the primary reason for the administration of ATP-depleting agents concomitantly with anticancer agents. This concept stipulates that ATP depletion therapy achieve approximately an 85% reduction in ATP level in the cancer cells to further lower the ATP reduction induced in cancer cell sublethally injured by anticancer agents, and thereby convert the sublethal injury to lethality to enhance the agent-induced tumor regressions. To achieve this severe degree of ATP depletion, since multiple biochemical substrates are employed for the synthesis and generation of ATP, a combination of ATP-depleting agents that block enough of the concerned metabolic pathways to achieve the ATP objective of <20% of normal is stipulated to be administered concomitantly with the anticancer agent. Thus, this concept differs from past ATP depletion proposals in establishing, not only a precise understanding of the "why and how" ATP depletion enhances anticancer therapy, but precise scientific guidelines to enable successful translation to the clinic.

The appropriate use of combination ATP-depletion therapy as adjuvant treatment to effective cytotoxic cancer chemotherapy and radiotherapy is relevant to the problem of residual disease following present therapy for dancer. Present therapy may be quite effective as treatment, but often falls short of cure. The proposed ATP depletion strategy could result in the elimination of those residual cancer cells left after present treatment failure, and thus yield cures instead of temporary remissions. In the context of metastatic disease, this new therapeutic strategy could markedly enhance the antitumor response rates with reduction of the dose of the cytotoxic agent, and consequent reduction of toxicity, but nevertheless with gain of efficacy. Therapeutically-induced partial tumor regressions, and or complete tumor regressions that eventually recur, can be sensitive to severe ATP depletion.

REFERENCES

1. Budihardjo, II, Walker, D. L., Svingen, P. A., Buckwalter, C. A., Desnoyers, S., Eckdahl, S., Shah, G. M., Poirier, G. G., Reid, J. M., Ames, M. M., and Kaufmann, S. H. 6-Aminonicotinamide sensitizes human tumor cell lines to cisplatin, Clinical Cancer Research. 4: 117-30, 1998.
2. Eguchi, Y., Shimizu, S., and Tsujimoto, Y. Intracellular ATP levels determine cell death fate by apoptosis or necrosis, Cancer Res. 57: 1835-40, 1997.
3. Leist, M., Single, B., Castoldi, A. F., Kuhnle, S., and Nicotera, P. Intracellular adenosine triphosphate (ATP) concentration: a switch in the decision between apoptosis and necrosis, J. Exp. Med. 185: 1481-6, 1997.
4. Shimizu, S.', Eguchi, Y., Kamiike, W., Waguri, S., Uchiyama, Y., Matsuda, H., and Tsujimoto, Y. Bcl-2 blocks loss of mitochondrial membrane potential while ICE inhibitors act at a different step during inhibition of death induced by respiratory chain inhibitors, Oncogene. 13: 21-9, 1996.
5. Shimizu, S., Eguchi, Y., Kamiike, W., Itoh, Y., Hasegawa, J., Yamabe, K., Otsuki, Y., Matsuda, H., and Tsujimoto, Y. Induction of apoptosis as well as necrosis by hypoxia and predominant prevention of apoptosis by Bcl-2 and Bcl-XL, Cancer Res. 56: 2161-6, 1996.
6. Huschtscha, L., Andersson, C., Bartier, W., and Tattersall, M. Anti-cancer drugs and apoptosis. In: M. Lavin and D. Watters (eds.), Programmed Cell Death, The Cellular and Molecular Biology of Apoptosis, pp. 269-279., Harwood Academic Publishers, GinbH, Poststrasse 22, 700 Chur, Switzerland, 1993.
7. Nieminen, A. L., Saylor, A. K., He=an, B., and Lemasters, J. J. ATP depletion rather than mitochondrial depolarization mediates hepatocyte killing after metabolic inhibition, Am. J. Physiol. 267: C67-74, 1994.
8. Liu, X., Kim, C. N., Yang, J., Jemmerson, R., and Wang, X. Induction of apoptotic program in cell-free extracts: requirement for DATP and cytochrome c, Cell. 86: 147-57, 1996.
9. Kass, G. E., Eriksson, J. E. Weis, M., Orrenius, S., and Chow, S. C. Chromatin condensation during apoptosis requires ATP, Biochem. J. 318: 749-52, 1996.
10. Mehmet, H., Yue, X., Penrice, J., Cady, E., Wyatt, J. C., Sarraf, C., Squier, M., and Edwards, A. D. Relation of impaired energy metabolism to apoptosis and necrosis following transient cerebral hypoxia-ischaemia, Cell Death Differ. 5: 321-9, 1998.
11. Schmitt, E., Sane, A., and Bertrand, R. Activation and role of caspases in chemotherapy-induced apoptosis., Drug Resistance Updates. 2: 21-29, 1999.
12. Nicotera, P. and Leist, M. Energy supply and the shape of death in neurons and lymphoid cells, Cell Death Differ. 4:435-442, 1997.
13. Nicotera, P. and Leist, M. Mitochondrial signals and energy requirement in cell death, Cell Death Differ. 4: 516, 1997.
14. Berger, N. A. and Berger, S. J. Metabolic consequences of DNA damage: the role of poly (ADP-ribose) polymerase as mediator of the suicide response, Basic Life Sciences. 38: 357-63, 1986.
15. Tanizawa, A., Kubota, M., Hashimoto, H., Shimizu, T., Takimoto, T., Kitoh, T., Akiyama, Y., and Mikawa, H. VP-16-induced nucleotide pool changes and poly(ADP-ribose) synthesis: the role of VP-16 in interphase death, Exp. Cell Res. 185: 237-46, 1989.
16. Carson, D. A., Seto, S., Wasson, D. B., and Carrera, C. J. DNA strand breaks, NAD metabolism, and programmed cell death, Exp. 1 Cell Res. 164: 273-81, 1986.
17. Schraufstatter, I. U., Hinshaw, D. B., Hyslop, P. A., Spragg, R. G., and Cochrane, C. G. Oxidant injury of cells. DNA strand-breaks activate polyadenosine diphosphate-ribose polymerase and lead to depletion of nicotinamide adenine dinucleotide, J. Clin. Invest. 77: 1312-20, 1986.
18. Marks, D. I. and Fox, R. M. DNA damage, poly (ADP-ribosyl)ation and apoptotic cell death as a potential common pathway of cytotoxic drug action, Biochem. Pharmacol. 42:1859-67, 1991.
19. Gaal, J., Smith, K., and Pearson, C. Cellular euthanasia mediated by a nuclear enzyme: A central role for nuclear ADP-ribosylation in cellular metabolism, Trends Biochem. Sci. 12:129-132, 1987.
20. Zamzami, N., Susin, S. A., Marchetti, P., Hirsch, T., Gomez-Monterrey, I., Castedo, M., and Kroemer, G. Mitochondrial control of nuclear apoptosis (see co=ents], J. Exp. Med. 183: 1533-44, 1996.
21. Hirsch, T., Marchetti, P., Susin, S. A., Dallaporta, B., Zamzami, N., Marzo, I., Geuskens, M., and Kroemer, G. The apoptosis-necrosis paradox. Apoptogenic proteases activated after mitochondrial permeability transition determine the mode of cell death, Oncogene. 15: 1573-81/1997.

22. Kroemer, G., Zamzami, N., and Susin, S. A. Mitochondrial control of apoptosis, Immunol. Today. 18: 44-51, 1997.
23. Kroemer, G. Mitochondrial implication in apoptosis. Towards and endosymbiont hypothesis of apoptosis evolution, Cell DeatH Differ. 4: 443-456, 1997.
24. Janicke, R. U., Ng, P., Sprengart, M. L., and Porter, A. G. Caspase-3 is required for alpha-fodrin cleavage but dispensable for cleavage of other death substrates in apoptosis, J. Biol. Chem. 273: 15540-5, 1998.
25. Boulares, A. H., Yakovlev, A. G., Ivanova, V., Stoica, B. A., Wang, G., Iyer, S., and Smulson, M. Role of poly (ADP-ribose) polymerase (PARP) cleavage in apoptosis. Caspase 3-resistant PARP mutant increases rates of apoptosis in transfected cells, Journal of Biological Chemistry. 274: 22932-40, 1999.
26. Amarante-Mendes, G. P., Finucane, D. M., Martin, S. J., Cotter, T. G., Salvesen, G. S., and Green, D. R. Anti-apoptotic oncogenes prevent caspase-dependent and independent commitment for cell death, Cell Death & Differentiation. 5:298-306, 1998.
27. Sane, A. T. and Bertrand, R. Caspase inhibition in camptothecin-treated U-937 cells is coupled with a shift from apoptosis to transient G1 arrest followed by necrotic cell death, Cancer Res. 59: 3565-9, 1999.
28. Lemaire, C., Andreau, K., Souvannavong, V., and Adam, A. Inhibition of caspase activity induces a switch from apoptosis to necrosis, FEBS Lett. 425: 266-70, 1998.
29. Kuida, K., Haydar, T. F., Kuan, C. Y., Gu, Y., Ta'ya, C., Karasuyama, H., Su, M. S., Rakic, P., and Flavell, R. A. Reduced apoptosis and cytochrome c-mediated-caspase activation in mice lacking caspase 9, Cell. 94: 325-37, 1998.
30. Roy, N., Deveraux, Q. L., Takahashi, R., Salvesen, G. S., and Reed, J. C. The c-IAP-1 and c-IAP-2 proteins are direct inhibitors of specific caspases, EMBO J. 16: 6914-25, 1997.
31. Yoshida, H., Kong, Y. Y., Yoshida, R., Elia, A. J., Hakem, A., Hakem, R., Penninger, J. M., and Mak, T. W. Apaf1 is required for mitochondrial pathways of apoptosis and brain development, Cell. 94: 739-50, 1998.
32. Green, D. R. and Reed, J. C. Mitochondria and apoptosis, Science. 281: 1309-12, 1998.
33. Stolfi, R. L., Colofiore, J. R., Nord, L. D., Koutcher, J. A., and Martin, D. S. Biochemical modulation of tumor cell energy: regression of advanced spontaneous murine breast tumors with a 5-fluorouracil-containing drug combination, Cancer Res. 52: 4074-81, 1992.
34. Koutcher, J. A., Alfieri, A. A., Stolfi, R. L., Devitt, M. L., Colofiore, J. R., Nord, L. D., and Martin, D. S. Potentiation of a three drug chemotherapy regimen by radiation, Cancer Res. 53: 3518-23, 1993.
35. Stolfi, R. L., Colofiore, J. R., Nord, L. D., and Martin, D. S. Enhanced antitumor activity of an adriamycin+5-fluorouracil combination when preceded by biochemical modulation, Anti-Cancer Drugs. 7: 100-4, 1996.
36. Martin, D. S., Stolfi, R. L., Colofiore, J. R., Nord, L. D., and Sternberg, S. Biochemical modulation of tumor cell energy in vivo: II. A lower dose of adriamycin is required and a greater antitumor activity is induced when cellular energy is depressed, Cancer Invest. 12: 296-307, 1994.
37. Martin, D., Stolfi, R., and Colofiore, J. Apoptosis resulting from anti-cancer agent activity in vivo is enhanced by biochemical modulation of tumor cell energy. In: M Lavin, D. Watters (eds.), Programmed Cell Death, The Cellular and Molecular Biology of Apoptosis, 2-19-296, Harwood Academic Publishers, 1993.
38. Martin, D. S., Stolfi, R. L., Colofiore, J. R., and Nord, L. D. Marked enhancement in vivo of paclitaxel's (taxol's) tumor-regressing activity by ATP-depleting modulation, Anti-Cancer Drugs. 7: 655-9, 1996.
39. Martin, D., Matei, C., and Koutcher, J. Marked enhancement of radiotherapy-induced tumor regression by an NAD antagonist, 6-aminonicotinamide (6-AN)., Proc. Am. Assoc. Cancer Res. 41:283 (Abstract 1800):, 2000.
40. Martin, D., Stolfi, R., Nord, L., and Colofiore, J. Enhancement of chemotherapeutically-induced apoptosis in vivo by biochemical modulation of poly (ADP-ribose) polymerase, Oncol. Rep. 3: 317-322, 1996.
41. King, M. P. and Attardi, G. Human cells lacking mt] DNA: repopulation with erogenous mitochondria by complementation, Science. 246: 500-3, 1989.
42. Street, J. C., Mahmood, U., Ballon, D., Alfieri, A. A., and Koutcher, J. A. 13C and 31P NMR investigation of effect of 6-aminonicotinamide on metabolism of RIF-1 tumor cells in vitro, J. Biol. Chem. 271: 4113-9, 1996.
43. Colofiore, J. R., Stolfi, R. L., Nord, L. D., and Martin, D. S. Biochemical modulation of tumor cell energy. IV. Evidence for the contribution of aden.osine triphosphate (ATP) depletion to chemotherapeutically-induced tumor regression, Biochem. Pharmacol. SO: 1943-8, 1995.
44. Nord, L. D., Stolfi, R. L., Alfieri, A. A., Netto, G., Reuter, V., Sternberg, S. S., Colofiore, J. R., Koutcher, J. A., and Martin, D. S. ApopL@.osis induced in advanced CD8F1-murine mammary tumors by the combination of PALA, MMPR and 6AN precedes tumor regression and is preceded by ATP depletion, Cancer Chemother. Pharmacol. 40: 376-84, 1997.
45. Colofiore, J., Stolfi, R., Nord, L., and Martin, D. On the relationship of ATP depletion to chemotherapeutically-induced tumor regression, Int. J. Oncol. 7: 1401-1404, 1995.
46. Shantz, G. D., Smith, C. M., Fontenelle, L. J., Lau, H. K., and Henderson, J. F. Inhibition of purine nucleotide metabolism by 6-methylthiopurine ribonucleoside and structurally related compounds, Cancer Res. 33: 2867-71, 1973.
47. Woods, R. A., Henderson, R. M., and Henderson, J. F. Consequences of inhibition of purine biosynthesis de novo by 6-methylmercaptopurine ribonucleoside in cultured lymphoma L5178Y cells, Euro. J. Cancer. 14: 765-70, 1978.
48. Warnick, C. T. and Paterson, A. R. Effect of methylthioinosine on ni-1-cleotide concentrations in L5178Ycells, Cancer Res. 33: 1711-5, 1973.
49. Nord, L. D., Stolfi, R. L., Colofiore, J. R., and Martin, D. S. Correlation of retention of tumor methylmercaptopurine riboside-5'-phosphate with effectiveness in CD8F1 murine mammary tumor regression, Biochem. Pharmacol. 51: 621-7, 1996.
50. Martin, D. S., Stolfi, R. L., and Colofiore, J. R. Perspective: the chemotherapeutic relevance of apoptosis and a proposed biochemical cascade for chemotherapeutically induced apoptosis, Cancer Invest. 15: 372-81, 1997.
51. Jones, M. Pyrimidine nucleotide biosynthesis in animals: Genes, enzymes, and regulation of UMP synthesis, Ann. Rev. Biochem. 49: 253-279, 1980.
52. Martin, D. S. Purine and pyrimidine biochemistry and some relevant clinical and preclinical cancer chemotherapy research. In:. G. Powis, R A. Prough,(eds.), Metabolism and action of anti-cancer Drugs 91-140, 1987.
53. Martin, D. S. Cancer chemotherapy: past is prologue, Mt Sinai J. Med. 52: 426-34, 1985.

54. Sweet, S. and Singh, G. Accumulation of human promyelocytic leukemic (HL-60) cells at two energetic cell cycle checkpoints, Cancer Res. 55: 5164-7, 1995.
55. Herter, F., Weissman, S., Thompson, H., Hyman, G., and Martin, D. Clinical experience with 6-aminonicotinamide, Cancer Res. 21: 31-37, 1961.
56. Stolfi, R. L., Stolfi, L. M., Sawyer, R. C., and Martin, D. S. Chemotherapeutic evaluation using clinical criteria in spontaneous, autochthonous murine breast tumors, J. Nat. Cancer Inst. SO: 52-5, 1988.
57. Martin, D., Fugmann, R., Stolfi, R., and Hayworth, P. Solid tumor animal model therapeutically predictive for human breast cancer, Cancer Chemmother. Rep. 5: 89-109, 1975.

Third Series of Experiments

As reported previously (Cancer Res., 53:3518-3823, 1993), the ATP-depleting/pyrimidine-depleting three-drug combination, MAP, when combined with radiation, produced cures for the first time in a murine spontaneous breast cancer system. Cures are claimed because the advanced murine breast tumors, after treatment with three courses of MAP+radiation (15 Gy), underwent complete tumor regressions which continued in 25% of the mice for over a year (380 days). No complete regressions were obtained with MAP alone, and only one short-lived complete tumor regression was obtained in animals treated with radiation alone. The data demonstrate the potential of this new therapeutic approach to convert merely palliative (i.e., temporary tumor remissions) treatment to curative therapy, albeit only a 25% cure rate.

Question was then raised as to whether the MAP therapeutic strategy would improve radiation efficacy on human breast cancers. Accordingly, human breast cancer xenografts (MCF-7) were treated in mice with MAP+an even lesser amount of radiation (10Gy). For this pilot study, a small number of xenograft-bearing mice were employed for each of the following groups: 5GY radiation alone; MAP+5 Gy; 10 Gy radiation alone; MAP+10Gy. Three courses of MAP+radiation were administered on a q 10-11 day schedule. Final measurements were taken 66 days after the third course.

| Group | Response Rate (PR + CR) | PR* | CR** |
|---|---|---|---|
| 1. 5Gy | 1/26 (4%) | 1/26 (4%) | 0 |
| 2. MAP + 5Gy | 7/8 (88%) | 7/8 (88%) | 0 |
| 3. 10 Gy | 6/10 (60%) | 6/10 (60%) | 0 |
| 4. MAP + 10Gy | 7/7 (100%) | 4/7 (57%) | 3/7 (43%) |

*PR = partial tumor reduction (50% or greater regression).
**CR = complete tumor reduction; no measurable tumor.

It is more convenient to discuss the findings of this pilot study by expressing the results in percentages. 10 Gy of radiation (60% response rate) is much more effective than the poor response rate (4%) to 5Gy. However, the partial response rate of the combination of MAP+5Gy, 88% PR, is better than that of 10Gy alone (60%). Thus, MAP+5Gy was more effective than 10Gy alone (as was also noted in measurements of delayed tumor growth; data not presented). Significantly, MAP+10Gy produced a 100% response rate, and, strikingly, there were 3/7 (43%) complete tumor regressions. It was also noted that tumor volume of the 57% partial tumor regressions continued to regress despite no further treatment after the third course of MAP+radiation, whereas, in contrast, mice receiving 10Gy alone had tumor regrowth.

Conclusions—MAP is a very effective potentiating treatment to enhance the tumor response to radiation. Although this pilot experiment with human breast cancer xenografts (MCF-7) is short-term (66 days), in contrast to the above-noted published 380 day experiment with a 25% cure rate in a murine breast cancer, the results demonstrate a striking complete response rate (43%) that augurs well for an eventual cure rate. MAP clearly is a radiation response potentitor in both the murine and human tumor models.

These enhanced MAP+radiation therapeutic results, along with other published preclinical in vivo tumor studies demonstrating that MAP potentiates the cytotoxic efficacy of many anticancer chemotherapeutic agents, suggest that in clinical trials this novel therapeutic strategy will lengthen survival of patients with advanced cancer, and even produce some cures.

Fourth Series of Experiments

NOTE: The abbreviations used are: PARP, poly (ADP-ribose) polymerase; 6-AN, 6-aminonicotimide; MMPR, 6-methylmercaptopurine riboside; PALA, N-(phosphonacetyl)-L-aspartic acid; PR, partial regression; MAP, MMPR+6AN+PALA; 5-FU, 5-fluorouracil; NAD+ nicotinamide adenosine dinucleotide; ATP, adenosine triphosphate; MDR, multidrug resistance; DOX, doxorubicin.

Abstract

Purpose: To present—1). The facts supporting a novel concept for killing drug-resistant cancer cells; 2). The in vivo preclinical findings utilizing this new strategy that combines a focused ATP-depleting regimen with conventional anticancer agents; and 3). The therapeutic potential for clinical advance.

Experimental Design: The focus of the ATP-depleting regimen is to lower the average ATP level in cancer cells to, or at least close to, the cell viability ATP threshold of 15% of normal. This regimen is administered concomitantly with anticancer agents, and requires reduction of the dosage of anticancer agents by at least half.

Results: The reduced dose of the anticancer agent kills sensitive cancer cells, and causes sublethal injury to lesser sensitive (i.e., drug-resistant) cancer cells. The sublethal injury causes substantial, but not critical reduction of the ATP levels. The concurring ATP-depleting effect of the combined ATP-depleting regimen plus that of each of nine anticancer agents in the drug-resistant sublethally injured cancer cells lowers their ATP levels to or below 15% of normal, a threshold level of ATP insufficient to sustain cell life. The therapeutic result is enhanced tumor cell death. (i.e., greater tumor regressions) in the in vivo-treated experimental tumors. In a tumor model that is very sensitive (e.g., 90-100% tumor regressions) to one particular anticancer agent, taxotere, equivalent antitumor effects were seen with this single agent alone at MTD versus this single agent at one half its MTD plus the ATP-depleting regimen in short-term experiments (e.g. 6 weeks), but after long term periods (e.g. 10-12 weeks), the tumor rate diminished in the taxotere at MTD group as some tumors begin to progress, but not in the combined ATP-depleting-half-dose taxotere group.

Conclusions: Since the toxic side effects of anticancer agents are linked to dosage, and the latter is substantially reduced by the concomitantly administered ATP-depleting strategy, there is a clinical prospect for a gain in therapeutic activity with markedly less toxicity. At a minimum, although the remarkable reduction of the doses of anticancer agents when combined with a focused ATP-depleting regimen may provide no less a therapeutic effect, there will be the important therapeutic advance that the reduced cytotoxic drug dose (at least half the MTD) will sharply decrease the serious side effects of standard-dose and high-dose chemotherapy.

The focused ATP-depleting concept has been proven preclinically to provide specific cytocidal therapy for drug-resistant cancer cells sublethally-injured by conventional anticancer agents. The present ATP-depleting regimen is now entering clinical trial.

The ATP-depleting compounds employed to prove the concept are off patent. New agents that accomplish more selective ATP depletion are therapeutically applicable to enhancing the anticancer efficacy of all clinically-effective anticancer agents. Drug-resistant sublethally-injured cancer cells will remain a problem. This mini-review hopes to stimulate exploration of new combinations of ATP-depleting agents that might provide a superior therapeutic index.

Background

Clinically effective combination cancer chemotherapy may cause a complete regression of a patient's cancer, but the cancer often recurs yielding only a short remission usually with little improvement in survival time. Although the complete tumor regression is due to the killing of most of the cancer cells by drug-induced necrosis and apoptosis, some cancer cells are intrinsically drug resistant (i.e., less sensitive) to certain cytoxic agents, and are only sublethally-injured. As a result, these cells recover and grow again leading to the patient's death. It is these residual, viable, sublethally-injured cancer cells that are the reason for therapeutic failure. Since high doses of cytotoxic agents kill more cancer cells, the therapeutic strategy for several decades has revolved around dose intensification. However, the accumulated clinical data over these decades has demonstrated at best, only a minor impact on treatment outcome and high dose chemotherapy is associated with more untoward toxicities. The collective experience with this approach suggests that future results with this strategy will likely be, to quote Yogi Berra, "déjà vu all over again." Moreover emerging information on the genetically-programmed nature of cell death (including molecular aspects of apoptosis) obviates the assumption that a future emphasis on high dose programs will eventually lead to the complete eradication of all sublethally-injured cells by integrating new anticancer agents with an improved therapeutic index. The genetic heterogeneity within each individual tumor mandates quantitative biochemical differences between cancer cells. Therefore, there are genetically related factors in many cancer cells that ensures that there will usually be a population of sublethally-injured cancer cells following effective cancer chemotherapy, regardless of the superiority of the therapeutic index of any new anticancer drugs.

For example, some cancer cells have biochemical factors that can adversely affect their drug sensitivity. High glutatathione levels may diminish the intracellular drug levels to ineffective cytotoxic species leading to decreased efficacy; while overexpression of p-glycoprotein may disallow adequate intracellular accumulate of a specific anticancer agent. High intracellular drug concentrations are required to cause cell death by the necrosis pathway since necrosis will not occur unless the drug-target "hit" is of sufficient magnitude (1-3). Such processes tend to strongly activate poly (ADP-ribose) polymerase (PARP) resulting in a depletion of glycolytic NAD+, thereby markedly inhibiting the glycolytic generation of ATP (4-8). This consequent severe depletion of ATP eventuates in cell death by necrosis (3, 9-10). Intracellular ATP levels cannot sustain cellular homeostasis and viability when reduced to 15% of normal or lower (12-13). Reductions above these levels only causes inhibition of cell proliferation followed by complete recovery (12-13). Thus, it is only this severe 85% depletion of intracellular ATP levels that determines whether cell death is by necrosis (9-10). Furthermore, some cancer cells have additional genetic barriers (i.e., other mechanisms of intrinsic drug resistance) that prevent cell death which cannot be overcome by dose intensification strategies. (Discussed later.)

Mechanism of Cancer Cell Death After Treatment: Necrosis vs. Apoptosis

By the early 1990's, necrosis as a mechanism of cancer cell death after effective cytotoxic treatment was not thought to be important in cancer therapy since clinically effective anticancer agents were considered to kill cells primarily by apoptosis (14). Since apoptosis (an ATP independent process), and necrosis (an ATP dependent process), were considered as two distinct mechanisms of cell death, each with distinctly different biochemical, morphological and functional characteristics (15-18), severe ATP depletion (as in effecting cell death by necrosis) was never thought to be important in the development of new anti-cancer strategies.

In contrast, cell death by both necrosis and apoptosis can be found simultaneously in different cells of the same tumor exposed to the same anticancer agent (2, 14, 19-20). Most anticancer agents effect DNA injury that simultaneously initiates both the necrosis and apoptosis modes of cell death in the same injured cancer cell. More specifically, DNA injury causing PARP activation leading to necrosis, while the same DNA injury in apoptosis induces mitochondrial damage (21-23) that causes release of cytochrome C leading to activation of the caspase cascade and apoptosis (24-25). If PARP cleavage occurs by an activated caspase, necrosis is prevented in that cell, and apoptosis prevails. (26-27, 8). If PARP cleavage is prevented by an endogenous intracellular caspase inhibitor (28), necrosis prevails in that cell, assisted by the ATP depletion from the apoptotically-damaged mitochondria (8). The purpose of PARP cleavage by a caspase is believed to prevent the induction of necrosis during apoptosis and ensure complete execution of caspase-mediated apoptosis. The initial intracellular ATP levels may govern whether an anticancer agent induces necrosis or apoptosis (9-10). Since both modes of cell death are simultaneously induced by the DNA damage, if the intracellular concentration of the cytotoxic is low, then DNA damage is reduced, resulting in poor stimulation of PARP. As a result, activation of caspases, before ATP depletion can fall to very low levels causing death by necrosis, results in caspase-executed apoptosis (30). If there is greater availability of endogenous caspase inhibitors versus caspases, this can favor cells to die from necrosis rather than apoptosis. There are many reports of inhibition of caspase activity not conferring a survival advantage following induction of apoptosis because the result is a "shift" from apoptotic cell death to necrotic cell death (9, 10, 15, 18, 10, 23, 32-38). This "shift" supports a connection between necrosis and apoptosis. Thus, contrary to reports primarily stressing apoptosis induction by anticancer drugs (14), it is becoming increasingly clear that anticancer agents kill cancer cells by both necrosis and apoptosis in the same tumor (but in different cancer cells) (2, 39). Indeed, classic apoptosis and necrosis apparently represent two extremes of a continuum of intermediate forms of cell demise (3, 39-41). Moreover, rather than viewing the two processes in functional opposition, the more realistic perspective likely involves a functional cooperativity between necrosis and apoptosis. For example, if apoptosis is blocked by caspase inhibitors, the apoptosis-induced mitochondrial damage results in lower ATP production, facilitating severe degrees of ATP depletion required for necrotic cell death (9, 12-13). There are also reports that failure to cleave PARP enhances the induction of both necrosis and apoptosis (29). The activation of cell death by necrosis or apoptosis is part of the normal course of events following cytotoxic therapy. Under certain circumstances, these two pathways share a common event, ATP depletion, that can be the "Achilles heel" of sublethally injured cells and result in cell death when strong ATP-depleting regimens are co-administered with the anticancer agents.

The anticancer agent-induced mode of cell death, necrosis or apoptosis, is initially dependent on the magnitude of the drug concentration reaching the cancer cell; that is, lower concentrations induce apoptotic cell death, while higher concentrations produce a necrotic cell death (2-3). However, drug concentration is not the only determinant. Some cancer cells in the heterogeneous neoplastic cell population may be intrinsically resistant to apoptotic cell death due to overexpression of antiapoptotic mediaters like bcl-2 (19), or underexpression of proapoptotic bax (22). Other cancer cells may only be sublethally injured because they have endogenous intracellular inhibitors of caspases (28) and/or possess genetic deletions of caspases (42-43). Because apoptosis is mediated by activated caspases, the genetic loss of caspases or the inhibition (block) of caspase activity prevents apoptotic cell death. Under these conditions, apoptosis can be initiated (i.e., mitochondria are damaged), but apoptosis is never fully executed. In apoptosis, the anticancer agent-induced DNA damage decreases mitochondrial permeability resulting in a cessation of the mitochondrial generation of ATP (9, 11, 21, 44). This mitochondrial damage usually activates the caspase cascade that mediates apoptosis (30), but apoptosis will not ensue if there is no caspase activation (i.e., high levels of intracellular endogenous caspase inhibitors (28); genetically-induced caspase deletions (42-43); high levels of antiapoptotic bcl-2 (19); or low levels of bax). As a result, continued PARP activity depletes ATP resulting in necrotic cell death (11-13). However, this chain of events will not occur unless the drug-target "hit" is sufficiently intense enough to strongly activate PARP, an event that will not occur in cells with high intracellular glutathione, P-glycoprotein overexpression, or where poor intracellular transport exists. Clearly, there are many reasons for cells to be only sublethally-injured (Table 4).

TABLE 4

Some Barriers to the Completion of Cell Death
Pathways* in Cancer Cells Sublethally-Injured
by High Dose Combination Chemotherapy

| High Glutathione | High levels of antiapoptotic bcl-2 |
|---|---|
| P-glycoprotein | Low levels of proapoptotic bax |
| Reduced intracellular transport | Endogenous caspase inhibitors |
| | Gene deletions (apaf-1;caspases) |

*Both necrosis and/or apoptosis

Concept: ATP Depletion Auguments Treatment-Induced Cell Killing

The most fundamental aspect of the concept states that a substantial degree of ATP depletion will always occur in anticancer agent-induced sublethally-injured cancer cells if there is only initiation, but not completion, of the necrosis and apoptosis pathways of cell death. (8). The fact that all anticancer agents induce depletion of a metabolite necessary for cell viability in their sublethally-injured cancer cells presents a unique therapeutic opportunity. Targeting the sublethally-injured cells for death through the concomitant administration of ATP-depleting agents to further reduce the anticancer agent-induced ATP to cell-killing levels of 15% of normal or below (12-13) represents a potentially new therapeutic approach to cancer treatment.

The ATP-Depleting Strategy Obviates the Need for High Dose Cytotoxic Therapy

Multiple biochemical pathways contribute to the synthesis, generation and maintenance of ATP. Therefore, a combination of ATP-depleting agents that sufficiently block the ATP-generating pathways to achieve 85% or more reduction in the ATP pools can be achieved when co-administered with anticancer agents. Since the sublethal injury to cancer cells by anticancer agents alone lowers ATP levels, the overall combination of an ATP-depleting regimen plus cytotoxic agents can collectively result in 85% or more reduction in ATP. These strategies are synergistic, resulting in increased cancer cell deaths (i.e., significantly greater tumor regression rates) over that seen with either the anticancer agents alone at high dosage (i.e., MTD), or with the ATP-depleting regimen alone. When combined with an ATP-depleting regimen, all anticancer agents had their effective doses reduced to approximately half their MTD as single agents. In a tumor model (MDA-MB-468) that is very sensitive (e.g., 90-100% tumor regressions) to a single agent (e.g., taxotere) equivalent antitumor effects were seen initially (i.e., over 6 weeks) with this single agent alone at the MTD versus this single agent at one half the MTD plus the ATP-depleting regimen. However, over longer observation periods (e.g., 12 weeks), the tumor regression rate diminished in the taxotere at MTD group, but not in the combined ATP-depleting-half-dose taxotere group. As summarized in Table 5, the ten anticancer agents which were co-administered with an ATP-depleting regimen all had their effective therapeutic doses reduced to approximately half of their MTD as single agents. Since the toxic side effects of anticancer agents are linked to high dosage, the ATP-depleting therapeutic strategy presents the exciting clinical prospect of a gain in therapeutic activity with less toxicity. If confirmed by clinical trial, such ATP-depleting strategies may appreciably lessen the morbidity and mortality faced by cancer patients in receiving combination chemotherapy. The strikingly reduced dosage (half the MTD) of the anticancer agents that is required by the ATP-depleting therapeutic strategy should markedly ameliorate, if not obviate, most side effects of conventional high dose cancer chemotherapy (e.g., emesis, diarrhea, alopecia, asthenia, fatigue, myelosuppression, febrile neutropenia requiring hospitalization, neurosensory and neuromotor disturbances, arthralgias/myalgias, heart failure and occasional deaths).

TABLE 5

Anticancer Agents Which, When Co-administered
with an ATP-depleting Regimen*, Reduce Their
Optimal Therapeutic Dose[1] by Half

| Doxorubicin | Etoposide |
|---|---|
| Cyclophosphamide | Cisplatin |
| Taxotere | Mitomycin |
| Paclitaxel | Phenylalanine Mustard |
| 5-Fluorouracil | Radiation |

*MMPR + 6-AN (+a pyrimidine antagonist, PALA) aimed at reducing ATP levels in cancer to 15% of normal or below, when administered with an anticancer agent.
**MTD = Maximal Tolerated Dose
[1]MTD When In The Overall Combination Is Approximately Half the MTD of The Agent Alone.

MAP—An Appropriate ATP-Depleting Combination

Two ATP-depleting agents, 6-methylmercaptopurine riboside, (MMPR), a known inhibitor of de novo adenine biosynthesis required for ATP generation (46), and, 6-aminonicotinamide, (6-AN), a known inhibitor of glycolysis and thus ATP generation (47-49), and an inhibitor of de novo pyrimidine biosynthesis, N-(phosphonacetyl)-L-aspartic acid (PALA) (50), have been evaluated in vivo in mice bearing advanced tumors. Collectively, these three agents are referred to by the acronym, MAP (8). Interestingly, pyrimidines may also be reduced in the cancer cells sublethally injured by cytotoxic agents. Because the de novo pyrimidine biosynthesis pathway partly occurs in mitochondria (51), it was reasoned that the anticancer agent-induced mitochondrial damage (11,21,44) could decrease de novo pyrimidine production, which could be lowered further by the concomitant administration of an inhibitor of de novo pyrimidine biosynthesis (e.g., PALA). Depletion of ATP would then lead to the inhibition of the salvage pathway formation of di-and triphosphate pyrimidines at the kinase step.

6-Aminonicotinamide alone only reduced ATP to 69% of normal while MMPR alone reduced ATP levels to 34% of normal. More importantly however, the combination (MMPR plus 6-AN) reduced ATP to 15% of normal (8). PALA, as expected, had no effect on ATP levels (8), but the UTP pools in the in vivo MAP-treated tumors (which were severely ATP-depleted to 15% of normal) were greatly reduced to 14% of normal (52). Neither 6-AN plus PALA, nor MMPR plus PALA had tumor-regressing activity, though the addition of PALA to MMPR and 6-AN, i.e., MAP, significantly enhanced tumor-regressing activity over that of MMPR+6-AN (52-53). Thus, it is the presence of severe lowering of ATP levels (to 15% or less of normal) by MMPR and 6-AN that is the basis for the PALA-induced pyrimidine depletion which appears to greatly augment the antitumor activity of the MAP regimen.

The MMPR and 6-AN induced depletion of ATP to 15% of normal (8) is only an average. While some individual tumors likely have ATP levels <15% of normal, and regress, other MAP-treated tumors may not develop a greater than 15% depletion of ATP, and do not regress as a result. However, since anticancer agents themselves can cause a reduction in ATP (8, 45), the ATP-depleting effect of anticancer agents plus MAP's reduction of ATP together deplete the ATP levels below the critical 15% level in more cells, thereby augmenting tumor regressions.

Preclinical In Vivo Evidence in Support of the Concept

MAP, when co-administered with anticancer agents to tumor-bearing mice, can significantly enhance response rates for the following agents: doxorubicin (54-55), paclitaxel (56), 5-fluorouracil (57), phenylalanine mustard (55), mitomycin C (58), cyclophosphamide[1], cisplatin (45), etoposide[1], taxotere[1], and radiation (55,58). As an example of the marked enhancement in therapeutic efficacy that can be achieved by this ATP-depleting strategy, it is interesting to note the following. In a series of advanced breast cancer experiments, cisplatin (CDDP) at 7/mg/kg (the MTD) significantly inhibited tumor growth but produced no partial (i.e., greater than 50% shrinkage of tumors), or complete response, whereas the combination of CDDP at 4 mg/kg (a 43% dose reduction) plus MAP produced a striking 54% partial tumor regression rate (45).

There is in vivo data (59, 60) confirming that therapeutic responses to ATP-depleting regimens plus an anticancer agent combination results in changes in cellular ATP levels. Both the depletion of ATP and the percent tumor regressions by MAP plus Doxorubicin (DOX) were significantly greater than those of MAP alone (59). Perhaps even more importantly, ATP depletion and tumor response rates become more profound as treatment is progressed from MAP, to MAP plus 5-Fluourouracil, to MAP plus DOX, and eventually to MAP plus 5-FU and DOX. The latter combination, MAP plus 5-FU and doxorubicin, depleted ATP levels the most, and resulted in tumor regression rates significantly higher than those seen in any of the former combinations (MAP plus 5-FU, or MAP plus DOX) (60). Thus, correlative biochemical data supports ATP depletion as a significant factor in the regression of these tumors.

[1]Unpublished studies

MAP "Works" with Combination Chemotherapy

The latter combination chemotherapy data cited above with MAP, 5-Flourouracil and doxorubicin also demonstrated that this ATP-depleting strategy would not necessitate a significant reduction in dose of these anticancer agents in combination. Combinations of cytotoxic agents are considered essential in the treatment of cancer due to considerable molecular heterogeneity of neoplastic cells in the tumor, and the variable intrinsic resistance seen among these cells. Dose reduction would likely compromise therapeutic efficacy.

The combination of an ATP-depleting regimen, MAP, has been evaluated with two anticancer agents, 5-fluorouracil and doxorubicin, in breast cancer-bearing mice (63). Table 6 demonstrates that it was not necessary to reduce the anticancer drug doses beyond that typically used as a single agent when each drug was combined with MAP. There was only a 3% mortality in the MAP plus 5-FU plus DOX group of 60 mice. In fact, the toxicity (i.e., weight loss) was not increased beyond the level seen in the combination of MAP plus FU or MAP plus DOX. In addition, there was a statistically significant increase in the tumor regression rate following treatment with MAP plus the combination chemotherapy of 5-FU plus DOX over that of MAP plus either of the single agents, including complete tumor regressions not previously achieved. These results suggest that the addition of perhaps other anticancer agents, (e.g., cyclophosphamide) may be "safe" with MAP, with the potential of effecting even greater anticancer results (i.e., after increased complete tumor regressions comes cures).

We have demonstrated previously that MAP plus 5-FU (57), or MAP plus DOX (54), produced greater antitumor activity than could be attained with either single agent at MTD. Moreover, various dosage ratios of the combination of 5-FU plus DOX (without MAP), up to and including higher doses that produce excessive mortality, produced tumor regression only at toxic doses, and even then, the rate of tumor regression did not approach that obtained with MAP plus the two agent in combination.

The increased antitumor activity without increased toxicity (and without the need to reduce the drug doses) when the drugs are used in combination suggests that the sublethal-effects of the combination of 5-Fluorouracil plus DOX are only minimally overlapping in normal tissues, and "selectively" target the tumor cell population. Therefore, a greater number of cancer cells are killed by the combined ATP-depleting activity of MAP plus the two anticancer drugs without increased host toxicity.

TABLE 6

The Effects Of MAP Plus Cytotoxic Drugs In
$CD_8F_1$ Mice Bearing Advanced Breast Tumors

| Treatment | % Body w't change | Regressions/survivors | Dead/total |
|---|---|---|---|
| 1. MAP | −17 | 1 PR/45 = (2%) | 5/50 = (10%) |
| 2. MAP-$FU_{75}$ | −19 | 30 PR + 1 CR/52 = (60%) | 7/59 = (2%) |
| 3. MAP-$Adr_6$ | −25 | 33 PR + 1 CR/57 = (60%) | 3/60 = (5%) |
| 4. MAP-$FU_{75}$+$Adr_6$ | −25 | 41 PR + 5 CR/58 = (79%) | 2/60 = (3%) |

Pooled results of 6 experiments: 2718F, 2777F, 2796F, 2813F, 2815M, 2816M. MAP = MMPR + 6AN + PALA. Three courses with a 10-11 day interval between courses. Observations 7 days after last treatment. Subscripts = mg/kg. CR = (complete regression). PR = (partial regression), i.e., reduction in tumor size of 50% or greater, when compared with tumor size at initiation of treatment. (1 st passage from brei of 4 spontaneous breast cancers.)

It is particularly important to note that the enhanced rate of tumor regressions produced by MAP plus 5-FU plus DOX was accomplished with doses of these later two agents that were essentially one-half their MTD as single agents in the q 10-11 day schedule (54, 57). At the clinical level, this would allow for a safer and longer period of doxorubicin administration, theoretically minimizing the potential for anthracycline-induced heart failure.

Preclinical Toxicity: MAP+AN Anticancer Agent

The combination of MAP plus an anticancer agent(s) causes body weight loss in the tumor-bearing mice, not accompanied by diarrhea or by histopathological changes in organs (such as the intestine). The cause seems to be severe anorexia and/or poor energy leading to a rigorous decrease in eating and drinking for a number of days after each of the three courses of intermittently-administered (e.g., q 14 days) therapy. Treatment-conditioned weight loss because of failure to eat or drink is not unusual for animals (or cancer patients) receiving intensive chemotherapy.

Weight loss can cause inhibition of tumor growth, but does not produce tumor regression. The therapeutic activity measured in all of our studies employs the stringent clinical criterion of tumor regression; specifically, 50% or greater decrease in tumor size. We have conducted experiments demonstrating that weight loss does not cause tumor regression. This fact is also apparent in some of our published studies with MAP. For example, in Table 6 (a pooled series of six experiments), groups 1 and two have similar weight loss (−17% and −19%), but group 1 evidence 60% tumor regressions whereas group 2 has only 2% tumor regressions. Also, groups 3 and 4 in Table 6 have identical weight loss (−25%), but statistically significant different tumor regression rates (60% versus 79%).

Weight loss per se is not expected to be a problem in cancer patients treated with the ATP-depleting strategy, because patients, unlike animals, can be persuaded to drink and eat, or can be supported intravenously, or by enteral-inserted tubes. However, the weight loss is a life-threatening problem for the treated tumor-bearing mice, particularly after three intermittently-spaced injections. After each treatment, the animals eat and drink very little for 5 or more days, a long period without sustenance for small animals with a high BMR. The weight loss has occasionally resulted in excess mortality after three intermittent injections in tumor-bearing athymic nude mice, although not in tumor-bearing normal mice.

Recently, we have made progress in preventing the mortality of severe weight loss by the administration of pyruvate, a natural by-product of glucose metabolism. Pyruvate diminishes the degree of weight loss, and is administered for 1 day only on the $5^{th}$ day after each ATP-depleting treatment (i.e., MAP+an anticancer agent) to avoid interference with the ATP-depleting efficacy of the treatment.

The Difference Between this and Former ATP-Depleting Attempts

The idea to use ATP depletion as a therapeutic strategy has been around for decades. Due to past failures at the clinical level, there is skepticism about ATP-depleting strategies. However, new information providing guidelines for its use have begun to emerge. There is now recognition that severe reduction of intracellular ATP concentrations to 15% of normal is the threshold level that induces cell death by necrosis, whereas lesser reductions only result in transient cessation of proliferation with eventual recovery. [The latter tumor growth inhibition is a therapeutic endpoint discernible in experimental tumors but not in the clinic where tumor regression, partial or complete, are the therapeutic endpoints (along with survival time)]. There is new information that the mechanism of cell death switches from apoptosis to necrosis when ATP levels are suppressed below this threshold. There is also new information that the interrelationships of apoptosis and necrosis result in a substantial, although non-lethal, reduction of ATP in cancer cells sublethally-injured by anticancer agents. These findings provide the rationale for the administration of various ATP depleting agents with anticancer drugs to further effect a reduction in ATP in sublethally-injured cancer cells. The expectation is that this further ATP reduction below the threshold in the sublethally-injured cancer cells would be cytocidal, whereas in normal tissues it would be only cytostatic allowing recovery. There is no equivalence between the former ATP-depleting efforts and the focused ATP-depleting strategy now proposed.

Is this ATP-Depleting Strategy "Selective"?

Perhaps the "selectivity" documented preclinically in vivo of this novel therapeutic approach is simply that energy requirements for cancer cells are higher and render them more sensitive to ATP depletion. Another conjecture is that the "selectivity" is determined by the anticancer agent, and not by the ATP-modulating agents. Tumor cells are inherently more sensitive to treatment-induced cell death than most normal tissues. Molecular alterations, which may increase cancer cell susceptibility to activation of cell death pathways, may enhance the therapeutic index of agents (61). If for example, the ATP-depleting agents effect a 45% (tolerable) reduction of ATP in both normal and cancer cells, and the anticancer agent effects a 45% (tolerable) reduction of ATP preferentially ("selectively") in the sublethally-injured cancer cells, the combination of the ATP-depleting agents and the anticancer agent would result in a 90% (and lethal) reduction of ATP only in the sublethally-injured cancer cells resulting in the death of the cancer cells (12-13). As discussed, cell metabolism and maintenance require a minimal level of ATP. For example, cell cycle events require a minimal ATP content to undergo proliferation (13). If ATP levels are reduced to levels above 15% of normal in the normal tissues, and below the minimal level necessary for cell division, only cell-cycle arrest, and not cell death, will ensue in the normal tissues. The ATP-depletion regimen plus the anticancer agent, by producing ATP reduction above 15% of normal in normal tissues, but below 15% of normal or below in the sublethally-injured cancer cells, could transiently damage the normal tissues but kill the sublethally-injured cancer cells. Quantitative comparison of ATP levels in multiple normal tissues and tumors following in vivo treatment with this therapeutic strategy should validate this "selectivity" explanation.

Essential Points to Consider
1. The major cause of treatment failure following effective anticancer treatment remains the survival and re-growth of sublethally-injured cancer cells.
2. Some cancer cells, genetically precluded from death by high dose therapy because they have molecular barriers to the completion of the cell death pathways of necrosis and apoptosis, can only be sublethally-injured.
3. Sublethally-injured cancer cells have substantial, but not lethal-inducing, reductions of ATP (and pyrimidines).
4. Intracellular ATP levels must be reduced to 15% of normal or below to kill cells.
5. This cytocidal effect of severe ATP depletion in cancer cells requires, since multiple biochemical pathways contribute to intracellular ATP generation, a combination of ATP-depleting agents that block enough of the ATP-generating pathways to reduce ATP levels in sublethally-injured cancer cells close to a level of 15% of normal.
6. Since sublethally-injured cancer cells also have reduction of pyrimidines, a non-toxic dose of a de novo pyrimidine inhibitor, when included with the ATP-depleting combination, enhances cell killing.
7. Since anticancer agents produce a substantial, but non-lethal, reduction of ATP levels in their sublethally-injured cells, biochemical modulation (62) by the combination of ATP-depleting agents (plus an inhibitor of pyrimidine biosynthesis), is co-administered with anticancer agents. The overall combination further reduces tumor ATP to even lower levels.
8. The therapeutic result of the concomitant administration of the ATP-depleting regimen (plus an inhibitor of pyrimidine synthesis) with each of nine different anticancer agents produces significant enhancement of each of their individual tumor regression rates.
9. These improved therapeutic results were obtained with approximately one-half the MTD of each of the nine anticancer agents studied as single agents.
10. Combination chemotherapy with an ATP-depleting regimen plus two agents (at their required half-dosage), resulted in increased tumor-regressing activity without need for additional reduction of drug doses, demonstrating no overlapping toxicity in normal tissues, and "selective" targeting of the tumor cell population.
11. The strikingly reduced dosage (half the MTD) of the anticancer agents that is required by the ATP-depleting therapeutic strategy could markedly ameliorate most side effects of conventional cancer chemotherapy, which in and of itself would be a beneficial gain in the treatment of cancer patients.
12. The more important potential for clinical benefit is that this detailed method of combining ATP-depleting agents with cytotoxic therapy is directed at killing the sublethally-injured cancer cells left after present treatment failures, and could yield markedly improved treatment outcomes.

Clinical Trial
Together, the summarized facts establish the concept that a detailed ATP-depleting strategy can improve cancer treatment in vivo at the preclinical level. The emphasis in this review has been on the general concept that therapeutic advance can be achieved by combining ATP-depleting agents with anticancer treatment, and not on the particular ATP-depleting agents, (MMPR and 6-AN and PALA). These compounds have no sponsor as they are all off patent. Clearly, this preclinically established concept requires clinical validation. Clinical supplies of MAP, to be provided by the National Cancer Institute through its RAID (Rapid Access to Intervention Development) program, have just been approved.

Possible Outcomes of a MAP Clinical Trial
The primary purpose of the proposed clinical trial is to validate the ATP-modulatory concept, and not simply the effects of the specific ATP-depleting regimen of MAP. The fact that all of the MAP components have been evaluated for toxicity in clinical trials previously should allow for more rapid hypothesis testing. The clinical results with MAP could differ from the preclinical results in certain aspects. The ATP-modulatory concept requires combination with an anticancer agent that has activity against the particular target tumor. In the preclinical results selected experimental tumors always had some sensitivity to the selected anticancer agents. Therefore, the ATP-modulatory effect on therapeutic efficacy could be consistently evaluated. In contrast, in the clinical situation, it is less likely that a particular anticancer agent will consistently effect a predictable response against the cancer. In the relatively small numbers of patients typically evaluated in such early phase clinical trials, it is likely that the clinical results with MAP plus an anticancer agent will generate some uncertainty with regard to its impact on therapeutic efficacy. This inherent uncertainty will not necessarily indicate that the concept is wrong.

Concepts of chemotherapy derived from experimental tumor model systems in almost every instance have been applicable to the clinical situation-if and when these concepts have been tested appropriately (64). In this clinical situation, "appropriately" means that the "proof-of-principle" ATP measurement studies should find that the combination of the ATP-depleting regimen plus the anticancer agent lowers the human tumor ATP content to levels of 15% of normal or below. Such "proof-of-principle" clinical studies are subject to uncertainties: (1), availability of tumor tissue for biochemical ATP assay, or NMR quantitative ATP measurements; (2) the appropriate timing for the post-treatment determination of the nadir of ATP depletion. In the preclinical studies, it is possible to take tumor ATP measurements 1-5 days post-treatment and determine the nadir of ATP depletion. In the clinical situation, patients agree to a pre-and a post-treatment measurement. Selecting the "appropriate" post-treatment day for the ATP nadir is uncertain [for correlation with evidence of cancer cell deaths (i.e., tumor regression)]. There are studies that show that cell killing by apoptosis and by necrosis occurs for up to six days after treatment (69). Measuring ATP in tumors up to 3 days after treatment is appropriate for those human tumors whose cells undergo rapid ATP depletion and therefore early cell death, but obviously not for the human tumor whose cells reach their nadir of ATP depletion much later after treatment. Selecting the wrong day (time) for the ATP assay can lead to the wrong conclusion of "proof-of-principle" studies.

Pointing out these uncertainties are not caveats to prepare acceptance of the "concept" regardless of such possible findings. Overall, given that the considerable preclinical in vivo data have demonstrated that the MAP regimen sensitizes advanced murine tumors to conventional therapeutics, it is anticipated that the MAP clinical trials will yield encouraging clinical results. At a minimum, it is anticipated that a marked reduction of the dose of anticancer agents in combination with MAP will provide no less a therapeutic effect, but the important therapeutic advance that reducing cytotoxic drug dose may decrease the serious side effects of standard-dose and high-dose chemotherapy.

A Better ATP-depleting Combination

Other combinations of ATP-depleting agents besides MAP can accomplish the same therapeutic objective of enhancing anticancer agent-induced tumor regressions when co-administered with clinically-effective anticancer agents[1]. Some of these combinations may be better than MAP, but require additional studies, and longer delay of a clinical trial of the concept. The MAP preclinical data appear convincing and presage promising clinical applications. The MAP regimen seems to be a reasonable first choice for clinical evaluation of the concept.

However, a new ATP-depleting regimen that had a superior therapeutic index (i.e., cytostatic to normal cells and selectively cytocidal to tumor cells) would transcend uncertain "proof-of-principle" findings, and potentially enhance therapeutic results. The components of MAP are off patent, and previous publications preclude a use patent. Better and patentable ATP-depleting agents can likely be developed by the pharmaceutical industry. Sublethally-injured cancer cells following therapy that survive, recur, and kill the patient are well-recognized as the problem to successful treatment, and a specific therapy (the ATP-modulatory concept) may be part of the answer. Clearly, there is much to learn, both by trial and error, and by employing comparative ATP measurements in normal tissues and tumors. New agents that accomplish ATP-depletion will be therapeutically applicable to enhancing the anticancer efficacy of all clinically-effective anticancer agents. This market is larger and more attractive than identifying a new drug for a molecular target that may affect only a relatively few sub-types of disease. Of course, the development of new molecular targeting agents continues to be important and, certainly, the ATP-depleting strategy requires the co-administration of effective anticancer agents. But the drug resistance of sublethally-injured cancer cells is a devastating therapeutic problem in the clinic that will remain even after the development of more rational and less toxic therapeutics. There are presently few new opportunities for enhancing cancer treatment in general. This review hopes to stimulate exploration of different combinations of ATP-depleting agents which might provide a superior therapeutic index.

This paper does not seek to promote necrosis and dismiss apoptosis as relevant to cell killing in cancer therapy. Apoptosis is considered the main cause of killing of tumor cells after treatment with anticancer agents, although the issue is now being debated (65-67). Regardless, disruption of apoptosis by whatever cause is a valid mechanism of drug resistance. We agree with the NIH Consensus Conference Statement For Breast Cancer (68), that there is no convincing evidence to demonstrate that more intensive dose-intensive treatment regimens result in improved outcomes compared with the administration of polychemotherapy programs at standard-dose levels. However, the latter programs have serious side-effects, and the proposed ATP-depleting strategy requires a marked reduction of dosage levels with the clear potential of ameliorating or obviating these toxicities, plus the promise of greater, or at least no less efficacy. The problem of combating drug resistance, killing the sublethally-injured cells following treatment, and preventing cancer recurrence after treatment-induced tumor regression, requires consideration of the limitations of present approaches, and a more balanced view of the field with new thinking. Every few years, the direction of cancer medicine should be reevaluated for the integration of science and medicine (70). The advent of targeted therapy with targets identified that may be useful in treatment (71) is exemplified by the identification of the reduction of ATP in cancer cells sublethally injured by anticancer agents. Thus, genetic information informs how to choose therapies based on genetic changes and specific aspects of the phenotype (71)—in this instance, by the genetically-induced vulnerability of the sublethally-injured cancer cell to focused therapy on a single molecule, ATP, whose further depletion can have profound effects on the progress of cancer (70). The accumulated evidence suggests that a focused ATP-depleting regimen that is very selective for cancer cells can be developed.

REFERENCES

1. Bonfoco, E, Krainc, D, Ankarcrona, M, Nicotera, P and Lipton, S A. Apoptosis and necrosis: two distinct events induced, respectively, by mild and intense insults with N-methyl-D-aspartate or metric oxide/superoxide in cortical cell cultures. Proc Natl Acad Sci., USA 92:7162-7166, 1995.
2. Huschtscha, L. I., Anderson, C. E., Bartier, W. A., and Tattersall, M. H. N. Anti-cancer drugs and apoptosis. In: M. Lavin and D. Walters (eds.), Programmed Cell Death, the Cellular and Molecular Biology of Apoptosis, pp. 269-278. New York: Harwood Academi, 1993.
3. Fromigli, L., Papucci, L., Tani, A, Schivone, N, Tempestine, A, Orlandini, G. E., Capaccioli, S, and Orlandini, S. Z. Aponecrosis: Morphological and biochemical exploration of a syncretic process of cell death sharing apoptosis and necrosis. J. Cell Physiol 182: 41-49, 2000.
4. Carson, D. A., Seto, S., Wasson, B., and Carrera, C. DNA strand breaks, NAD metabolism, programmed cell death. Exp. Cell Res., 164:273-281, 1986.
5. Gaal, J. C., Smith, K. R. and Pearson, C. K. Cellular euthanasia mediated by a nuclear enzyme: A central role for nuclear ADP-ribosylation in cellular metabolism. Trends Biochem. Sci., 12: 129-132, 1987.
6. Schraufstaffer, I. U., Hinshaw, D. B., Hyslop, P. S., Spragg, R. H., and Cochrane, C. G. Oxidant injury of cells DNA stand-breaks activate polyadenosine diphosphate polymerase and lead to depletion of nicotinamide adenine dinucleotide. J. Clin. Investig. 77:1312-1320, 1986.
7. Tonegawa, A., KUB Ota, M., Hashimoto, H., Shimadzu, T., Sakamoto, T., Kith, T., Akiyama, Y., and Mikamo, H. VP-16-induced nucleotide pool changes and poly (ADP-ribose) synthesis: the role of VP-16 in interphase death. Exp. Cell Res. 185:237-246, 1989.

8. Martin, D. S., Bertino, J. R. and Koutcher, J. A. ATP depletion pyrimidine depletion can markedly enhance cancer therapy: Fresh insight for a new approach. Cancer Res. 60:6776-6783, 2000.
9. Eguchi, Y., Shimizu, S., and Tsujimoto, Y. Intracellular ATP levels determine cell fate by apoptosis or necrosis. Cancer Res., 57:1835-1840, 1997.
10. Leist, M., Single, B., Castoldi, A. F., Kuknle, S., and Nicotera, P. Intracellular triphosphate (ATP) concentration: A switch in the decision between apoptosis and necrosis. J. Exp. Med., 185: 1835-1840, 1997.
11. Green, D. R. and Reed, J. C. Mitochondria and apoptosis. Science (Washington D.C.), 281: 1309-1312, 1998.
12. Nieminen, A. L., Saylor, A., Herman, B., and Lemasters, J. J. ATP depletion rather than mitochondrial depolarization mediates hepatocyte killing after metabolic inhibition. Am. J. Physiol., 267: C67-C74, 1994.
13. Sweet, S., and Singh, G. Accumulation of human promyelocytic leukemic (HL-60) cells at two energetic cell cycle checkpoints. Cancer Res., 55:5164-5167, 1995.
14. Hickman, J. A. Apoptosis induced by anticancer drugs. Cancer Mestasis Rev. 11:121-139, 1992.
15. Nicotera, P., and Leist, M. Energy supply and the shape of death in neurons and lymphoid cells. Cell Death Differ., 4:435-442, 1997.
16. Cotter, T. G., Lenon, S. V., Glynn, J. G and Martin, S. J. Cell death via apoptosis and its relationship to growth, development and differentiation of both tumor and normal cells. Anticancer Res. 10:1153-1160, 1990.
17. Wyllie, A. H. Apoptosis. Br. J. Cancer. 67:205-208, 1993.
18. Nicotera, P., and Leist M. Mitochondrial signals and energy requirement in cell death. Cell Death Differ, 4:516, 1997.
19. Reed. J. C. Regulation of apoptosis by bcl-2 family proteins and its role in cancer and drug resistance. Curr. Opin. Oncol. 7:541-546, 1995.
20. Shimizu, S., Eguchi, V., Kamike, W., Itoh, Y., Hasgawa, J., Yamabe, K., Otusid, Y., Matusada, H and Tsujimoto, Y. Induction of apoptosis as well as necrosis by hypoxia and predominant prevention of apoptosis by bcl-2 and bcl-x. Cancer Res. 56:2161-2166, 1997.
21. Kroemer, G., Zamzami, N. and Susin, S. A. Mitochondrial control of apoptosis Immunol. Today, 18, 18:44-51, 1997.
22. Green, D. R. Apoptoic pathways: The roads to ruin. Cell 94:695-695, 1998
23. Green, D. R. and Reed, J. C. Mitochondria and apoptosis. Science (Washington D.C.) 281:1309-1312, 1998.
24. Liu, X, Kim, C. N., Yang, J., Jemmerson, R and Wang, X. Induction of apoptotic program in cell-free extracts requirement for DATP and cytochrome c. Cell 86:147-157, 1996.
25. Zou, H., Li, Y., Liu, X., and Wang, X. An apaf-1-cytochrome c multimeric complex is a functional apoptosome that activates procaspase 9. J. Biol. Chem, 274: 11549-11556, 1999.
26. Boulares, A. H., Yokovlev, A. G. Ivanova, V., Stoica, B. A. Wang, G., Iyer, S, and Smulson, M. Role of poly (ADP-ribose) polymerase (PARP) cleavage in apoptosis. Caspase-3 resistant PARP mutant increases rates of apoptosis in transfected cells. J. Biol Chem. 274:22932-22940, 1999.
27. Janicke, R. V. Sprengart M. L., Wati, M. R. and Porter, A. G. Caspase-3 is required for DNA fragmentation and morphological changes associated with apoptosis. J. Biol. Chem., 273:9357-9360, 1998.
28. Roy, N., Deveraux, Q. L. Takahashi, R., Salvesen, G. S., and Reed J. C. The c-IAP-1 and c-IAP-2 proteins are direct inhibitors of specific caspases. EMBO J., 16:6914-6925, 1997.
29. Herzog, Z, and Wang Z. Q. Failure of poly (ADP/ribose) polymerase cleavage by caspases leads to induction of necrosis and enhanced apoptosis. Mol. Cell Biol. 19:5124-5133, 1999.
30. Schmitt, E., Sane, A. T., and Bertrand, R., Activation and role of caspases in chemotherapy-induced apoptosis. Drug Resistance Updates, 2:21-29, 1999.
31. Amarante-Mendes, G. P., Finucane, D. M., Martin, S. J., Cotter, T. G., Salvesen, G. S., and Green, D. R. Anti-apoptotic oncogenes prevent caspase-dependent and independent commitment for cell death. Cell Death Differ. 5:298-306, 1998.
32. Sane, A. T. Bertrand, R., Caspase inhibition in camptothecin-treated U-937 cells is completed with a shift from apoptosis to transient $G_1$, arrest followed by necrotic cell death. Cancer Res., 59:3565-3569, 1999.
33. Lemaire, C., Andreau, K., Souvannavong, K., and Adam, A. Inhibition of caspase activity induced a switch from apoptosis to necrosis. FEBS Lett. 425:266-270, 1998
34. Cappola, S., Nosseri, C., Maresco, V., and Ghibelli, L., Different basal NAD levels determine opposite effects of poly (ADP-ribosyl) polymerase inhibitors on $H_2O_2$-induced apoptosis. Exp. Cell Res., 221:462-469, 1995.
35. Kiang, J., Chao, T., and Korsmyer, S. G., Bax-induced cell death may not require interleukin 1-converting enzyme-like proteases. Proc-Natl. Acad. Sci. USA, 93:14359-14563, 1996.
36. Shimizu, S., Eguchi, Y., Kamuake, W., Waguris, S., Vchaiyama, Y., Matasuda, H. and Tsujimto, Y. Bcl-2 blocks loss of mitochondrial membrane potential with ICE inhibitors act at a different step during inhibition of death induced by respiratory change inhibitors, Oncogene 13:21-29, 1996.
37. Hirsch, T., Marchetti, P., Susin, S., Delaporta, B., Zamzami, N, Marzo, I., Geuskens, M., and Kroemer, G. The apoptosis-necrosis paradox. Apotgenic proteases activated after mitochondrial permeability transition determine the mode of cell death. Oncogene 15: 1573-1581, 1997.
38. Mehmet, H., Yue, X., Penrice, J., Cady, E., Wyatt, J. S. Surraf, C., Squier, M. and Edwards, A. D. Relaxation of impaired energy metabolism to apoptosis and necrosis following transient cerebral hypoxia-ischemia. Cell Death Differ. 5:321-329, 1998.
39. Staunton, M. J. and Gaffney, E. F. Apoptosis: basic concepts and potential significance in human cancer Arch Pathol. Lab. Med. 122:310-319, 1998
40. Lemasters, J. J. Necraptosis and the mitochondrial permeability transition: shared pathways to necrosis and apoptosis. Am. J. Physiol 296: G1-6, 1999.
41. Raffrey, M and Cohen, G. M. Apoptosis and necrosis in toxicology: a continuum or distinct modes of cell death? Pharmacol Ther. 75:153-177, 1997.
42. Kuida, K., Hayder, T. F. Kuan, C. Y., Gu, Y., Taya, C., Karasuyama, H., Su, M. S. S., Radic, P., and Flavell, R. A. Reduced apoptosis and cytochrome c-mediated caspase activation in mice lacking caspase 9. Cell, 94:3258-337, 1998.
43. Yoshida, H., Kong, Y. Y. R., Elia, A. J. Hakem, R., Penniger, J. M. and Mak, T. W. Apaf-1 is required for mitochondrial pathways of apoptosis and brain development. Cell, 94: 739-750, 1998.

44. Serefino, A, Sinibaldi-Vallebono, P, Lazzarino, G, Tavazzi, B., DiPierro, D, Rosi, G, and Ravagnan, G. Modifications of mitochondria in human tumor cells during anthracycline-induced apoptosis. Anticancer Res. 20: 3383-3394, 2000.
45. Martin, D. S., Spriggs, D and Koutcher, J. A. A concomitant ATP-depleting strategy markedly enhances anticancer agent activity. Apoptosis 6:125-131, 2001.
46. Shantz, G. D., Smith, C. M., Fontenella, L. J., Lau, H. K. F., and Henderson, J. F. Inhibition of purine nucleotide metabolism by 6-methylmercaptopurine ribonucleoside and structurally related compounds. Cancer Res. 33:2867-2871, 1973.
47. Hunting, D., Gowans, B. and Henderson, J. F. Effects of 6-AN on cell growth, poly (ADP-ribose) synthesis and nucleotide metabolism. Biochem. Pharmacol. 34:3999-4003, 1985.
48. Street, J. C., Mahmoud, V., Ballon, D., Alfieri, A. A. and Koutcher, J. A. $^{13}$C and $^{31}$P NMR investigation of effect of 6-aminonicotinamide on metabolism of RIF-1 tumor cells in vitro. J. Biol. Chem. 271:4113-4119, 1996.
49. Koutcher, J. A., Alfieri, A. A., Matei, C., Zakian, K. L., Street, J. C. and Martin, D. S. In vivo PNMR detection of pentose phosphate pathway block and enhancement of radiation sensitivity with 6-aminonicotinamide. Magn. Reson. Med. 36:887-892, 1996.
50. Martin, D. S., Stolfi, R. L., Sawyer, R. C., Spiegelman, S., Casper, E. S. and Young, C. W. Therapeutic utility of utilizing low doses of N-(phosphonoacetyl)-L-aspartic acid in combination with 5-fluorouracil: a murine study with clinical relevance. Cancer Res. 43:2317-2321, 1983.
51. Jones, M. Pyrimidine nucleotide biosynthesis in animals: Genes, enzymes and regulation of UMP synthesis. Ann Rev. Biochem. 49:253-279, 1980.
52. Martin, D. S., Purine and pyrimidine biochemistry and some relevant clinical and preclinical cancer chemotherapy research. In: G. Powis and R.A. Prough (eds) Metabolism and Action of Anti-Cancer Drugs, pp. 91-140. London: Taylor & Francis, 1987.
53. Martin, D. S. Cancer chemotherapy: past is prologue. Mt. Sinai, J. Med., 52:426-434, 1985.
54. Martin, D. S., Stolfi, R. L., Colofiore, J. R. Nord, L. D. and Sternberg, S. Biochemical modulation of tumor cell energy in vivo. II. A lower dose of Adriamycin is required and a greater antitumor activity is induced when cellular energy is depressed. Cancer Investig. 12:296-307, 1994.
55. Martin, D. S., Stolfi, R. L., Colofiore, J. C., Koutcher, J. A., Alfieri, A., Sternber, S., and Nord, L. D. Apoptosis resulting from anti-cancer agent activity in vivo is enhanced by biochemical modulation of tumor cell energy. In: M Lavin and D. Walters (eds.) Programmed Cell Death. The Cellular and Molecular Biology or Apoptosis, pp. 279 296, New York: Harwood Academic, 1993.
56. Martin, D. S., Stolfi, R. L., Colofiore, J. R., and Nord, L. D. Marked enhancement in vivo of paclitaxel's (Taxol's) tumor-regressing activity by ATP-depleting modulation. Cancer Drugs, 7:655-659, 1996
57. Stolfi, R. L., Colofiore, J. R., Nord, L. D., Koutcher, J. A. and Martin, D. S. Biochemical modulation of tumor cell energy: regression of advanced spontaneous murine breast tumors with a 5-fluorourcil containing drug combination. Cancer Res. 52: 4074-4981, 1992.
58. Koutcher, J. A., Alfieri, A., Stolfi, R. L. Devitt, M. L. Colofiore, J. R. Nord, L. D. and Martin, D. S. Potentiation of a three drug chemotherapy regimen by radiation. Cancer Res., 53:3518-3823, 1993.
59. Colofiore, J. R. Stolfi, R. L., Nord, L. D. and Martin, D. S. Biochemical modulation of tumor cell energy IV. Evidence for the contribution of adenosine triphosphate (ATP) depletion to chemotherapeutically-induced tumor regression. Biochem Pharmacol. 50:1943-1948, 1995.
60. Colofiore, J. R., Stolfi, R. L., Nord, L. D., and Martin, D. S. On the relationship of ATP depletion to chemotherapeutically-induced tumor regression. Int. J. Oncol. 7:1401-1404, 1995,
61. Lowe, S. W. Cancer therapy and p53. Curr. Opin. Oncol. 7:547-553, 1995.
62. Martin, D. S. Biochemical modulation perspectives and objectives. In: K. R. Harrap (ed). New Avenues in Developmental Cancer Chemotherapy, pp. 113-162, London, Academic Press 1986, 1986.
63. Stolfi, R. L., Colofiore, J. R., Nord. L. D., and Martin, D. S. Enhanced antitumor activity of an Adriamycin+5-Fluorouracil combination when preceded by biochemical modulation. Anti-Cancer Drugs 7:100-104 1996.
64. Bertino, J. R. Editorial. J. Clin. Oncol. 8 (2): 193-195, 1990.
65. Brown, J. M. and Wouters, B. G. Apoptosis: mediator or mode of cell killing by anticancer agents? Drug Resistance Updates 4:129-130, 2001.
66. Borst, P., Borst, J., Smets, L. A. Does tumor cell resistance affect the outcome of chemotherapy? Drug Resistance Updates 4:129-130, 2001
67. Schmitt, C. A. and Lowe, S. W. Programmed cell death is critical for drug response in vivo. Drug Resistance Updates 4:132-134, 2001.
68. National Institute of Health Consensus Development Conference Statement. Adjuvant Therapy for Breast Cancer, Nov. 1-3, 2000. J. Natl. Cancer Inst. 93:979-989, 2001.
69. Forrester, H. B., Albright, N., Ling, C. C. and Dewey, W. C. Computerized video time-lapse analysis of apoptosis of REC: Myc cells X-radiated in different phases of the cell cycle. Radiat. Res. 154:625-639, 2000.
70. Norton, L. ASCO Presidential Address. OT ASCO Reporter, p. 4-5, July 2001.
71. Varmus, H. Special Session on the Biology of Cancer. OT ASCO Reporter, p. 22, July 2001.

Fifth Series of Experiments

MAPAL, A New Combination of ATP-Depleting Agents is Cytocidal for Anticancer Agent-Induced Sublethally-Injured (i.e., Drug-Resistant) Cancer Cells Clinically-effective combination cancer chemotherapy may cause complete regression of a cancer, but the cancer invariably recurs due to cancer cells that are only sublethally-injured, recover, and grow again. These drug-resistant cells are a fatal therapeutic problem that will remain even after the development of new anticancer agents that are more rational, more targeted, and less toxic. The reason is that the cancer cells that are less sensitive to anticancer drugs have genetically-induced biochemical barriers that prevent completing the cell death pathways of apoptosis and/or necrosis (1). Nevertheless, damage occurs: the interrelationship between apoptosis and necrosis cell death pathways, induced by chemotherapeutic agents in the sublethally-injured cancer cells, reduces the essential metabolite, ATP, but not to levels low enough to be cytocidal (2). We have demonstrated that further reduction of ATP to cytocidal levels (15% of normal and below) by a novel ATP-depleting regimen, MAP, co-administered with conventional anticancer agents, generally enhances tumor regression rates even over those induced by the anticancer agent at high doses (i.e., at the maximally tolerated dose, MTD (1-2). MAP is an acronym for the combination of 6-methylmercaptopurine riboside (MMPR) plus 6-Aminonicotinomide (6-AN) plus PALA.

MMPR, an inhibitor of de novo purine synthesis, limits adenine availability for ATP synthesis. L-alanosine, a drug that specifically blocks de novo AMP synthesis, should further deplete the ATP depletion induced by MMPR when co-administered with MMPR. Indeed, in vitro studies have shown the combination of L-alanosine+MMPR to significantly improve tumor growth inhibition (3). In another in vitro study of cancer cells (4), although alanosine alone, reduced the intracellular tumor cell ATP pool only to 63% of normal, and MMPR alone to 49% of normal, the combination of alanosine plus MMPR further depleted the ATP pool to 34% of normal. All of these ATP depletion levels (63%, 49% and 34% of normal) only adversely effect cell proliferation rates; i.e., cause various degrees of tumor growth inhibition (5). Thus, the combination of alanosine+MMPR only completely inhibited cell growth (4), but cell growth resumed immediately after removing the two drugs from the medium (4). But, if the ATP level in the cancer cells had been further reduced to the cell-killing threshold level of 15% of normal and less, cell viability would not be sustained (5-6), and tumor regressions would ensue (1-2). This reasoning suggested the addition of alanosine (AL) to MAP, creating the acronym of MAPAL.

The new ATP-depleting regimen, MAPAL, has a superior therapeutic index over MAP (i.e., cytostatic to most normal cells and more selectively cytotoxic to tumor cells). The components of MAP are off patent, and previous publications of MAP preclude a use patent. The combination of agents in MAPAL is new, has never been published, and warrants a use patent for co-administration with anticancer agents in conformity with our ATP-modulatory concept (now in the process of being patented). Sublethally-injured cancer cells following therapy survive, recur, and kill the patient. These drug-resistant cancer cells are well-recognized as the problem to successful treatment, and specific therapy with MAPAL may be an important part of the answer as a therapeutic enhancing addition to all clinically-effective anticancer agents.

REFERENCES

1. Martin, D. S., Bertino, J. R., Koutcher, J. A., Norton, L., and O'Connor, O. A. Cytocidal therapy for drug-resistant cancer cells. Cl. Cancer Res., submitted for publication.
2. Martin, D. S., Bertino, J. R., and Kouthcer, J. A. ATP depletion+pyrimidine depletion can markedly enhance cancer therapy: Fresh insight for a new approach. Cancer Res. 60:6776-6783, 2000.
3. Li, W. W, Cole, P., Martin, D. S., Banerjee, D. and Bertino, J. R. Methylthioadenosine phosphorylase (MTAP) status determines sensitivity to L-alanosine in human soft tissue sarcoma cell lines and is enhanced by 6-methylmercaptopurine riboside (MMPR). Proc. Am. Assoc. Cancer Res. 41:240, 2000.
4. Nguyen, B. T., El Sayed, Y. M. and Sadee, W. Interaction among the distinct effects of adenine and guanine in mouse lymphoma cells. Cancer Res. 44: 2272-2277, 1984.
5. Sweet, S. and Singh, G. Accumulation of human promyelocytic leukemic (HL-60) cells at two energetic cell cycle checkpoints. Cancer Res. 55:5164-5167, 1995.
6. Nieminem, A. L., Saylor, A., Herman, B., and Lemasters, J. J. ATP depletion rather than mitochondrial depolarization mediates hepatocyte killing after metabolic inhibition. Am. J. Physion, 267. 267 (Cell Physiol. 36): 67-74, 1994.

Sixth Series of Experiments

MAPAL Cytocidal Therapy for Drug-Resistant Human Breast Cancer Xenografts

Concomitant ATP depletion with conventional anticancer agents—focused to the intracellular ATP lethality threshold of $\leq 15\%$ of normal by MAP, an acronym for 6-methylmercaptopurine riboside+6-aminonicotinamide (6-AN)+PALA—has been uniformly successful in enhancing tumoricidal activity in experimental tumors. (Martin et al, Cancer Res. 60: 6776, 2000). The addition of alanosine (AL), an inhibitor of de novo AMP synthesis, to MAP (i.e., MAPAL) to further increase ATP depletion is a new strategy to the MAP program. The tumor-regressing activity of MAPAL with an anticancer agent is superior to that of MAP, as in the experiment below.

TABLE 7

The tumor-regressing activity of MAPAL with an anticancer agent is superior to that of MAP, as in the experiment below.

| Treatment[a] | % Partial Regressions[b] | % Tumors Progressing[c] |
|---|---|---|
| Taxotere$_{40}$ | 100% | 0% |
| MAP + Taxotere$_{20}$ | 60% | 40% |
| MAPAL + Taxotere$_{20}$ | 100% | 0% |

[a]Treatment q 2 weeks x 3; MDA-MB-468 tumors averaged 100 mg at initiation of therapy
[b]P.R. = Partial tumor regressions < 50% of initial tumor size.
[c]Progressing tumors are larger than P.R. tumors, and growing.

Table 8 presents results one month after completing a q 2 week×3 schedule with Taxotere (TXT$_{40}$ or TXT$_{20}$; subscript=mg/kg), initiated in mice (10/grp) with subcutaneous advanced (100+mg) MDA-MB 468 breast cancer xenografts, are as follows:

TABLE 8

ENHANCED LONG-TERM[+] RESULTS OF THERAPY WITH LOW DOSE TAXOTERE + AN ATP-DEPLETING REGIMEN (MAPAL) IN SUBCUTANEOUS ADVANCED HUMAN BREAST CANCER XENOGRAFTS[***]

| Group | Treatment[**] | Mortality | NR[*] | PR[*] | (CR)[*] |
|---|---|---|---|---|---|
| 1 | Taxotere$_{40}$ | 0% | 40% | 60% | (10%) |
| 2 | TXT$_{20}$ | 0% | 100% | 0% | (0%) |
| 3 | MAPAL | 0% | 70% | 30% | (0%) |
| 4 | MAPAL + TXT$_{20}$ | 30% | 0% | 100% | (0%) |
| 5 | MAPAL + TXT$_{20}$ + Pyruvate | 10% | 10% | 90% | (20%) |
| 6 | MAPAL + TXT$_{20}$ (6-AN after Taxotere) + Pyruvate | 0% | 0% | 100% | (20%) |

[*]NR = no tumor regression <50%; PR = partial tumor regression < 50%; (CR) = complete tumor regression included in PR rate.
[+]Results 69 days after initiating therapy
[**]Therapy every 2 weeks x 3. Subscripts = mg/kg. TXT = taxotere i.v. MAPAL i.p.: M = 6-methylmercaptopurine riboside; A = 6-aminonicotinamide (6-AN); P = PALA; AL = alanosine.
[***]MDA-MB 468 human breast cancer xenografts averaging 100 mg. when therapy initiated; 10-11 tumor-bearing mice per group.

Conclusion—MAPAL+low dose Taxotere has the potential to extend survival rates maintaining a 100% P.R. (Group 6) at 69 days after initiating treatment. In contrast full (MTD) dose Taxotere (Group 1), which initially effected a 100% P. R., has lost 40% of its P. R. activity at this same time point by tumor regrowth beginning 41 days after the third and last injection. MAPAL+combination chemotherapy has the potential to ameliorate (or likely obviate) drug resistance. Note that MAPAL+a single agent (TXT) effects a 20% CR. Moreover, Group 6 at this long-term observation period is the only group with 3 tiny nubbins measuring only 9, 9, and 11 mg.

Unacceptable mortality (e.g., 30%) is prevented by pyruvate "rescue" without interference with tumoricidal activity. MAPAL+Taxotere enhances tumor regressions, including complete regression. The markedly reduced dosage (half-MTD) of anticancer agents, co-administered with focused ATP-depleting strategy, could ameliorate many of the side-effects of conventional chemotherapy. MAPAL+combination therapy (i.e., a combination of anticancer agents) has potential to extend survival rates for almost all cancers, and achieve cure for some. Clinical trial of MAP is under way.

Seventh Series of Experiments

ATP Depletion+Pyrimidine Depletion can Markedly Enhance Cancer Therapy—A New Therapeutic Strategy Abstract This is a clinical proposal based on molecular biology findings that cancer cells sublethally injured by therapy are switched to the cell death pathway of necrosis because the apoptosis pathway is blocked by endogenous inhibitors of caspases and/or genetic deletions of caspases. Additional cancer cells also are sublethally damaged because they are of lesser sensitivity to the anticancer agent for a variety of other reasons. In all these sublethally-damaged cells ATP and pyrimidines are reduced to low levels but not to low enough levels insufficient to support cell viability, and these cells recover, grow, and kill the patient.

It was hypothesized that adjuvant biochemical modulation—a combination of two ATP-depleting compounds, 6-methylmercapstopurine riboside (MMPR) to limit adenine supplies, and 6-aminonicotinamide (6-AN) to inhibit the glycolytic generation of ATP, and an inhibitor of pyrimidine synthesis, PALA; all collectively referred to as MAP—in conjunction with standard anticancer agents or radiation would further depress the agent-induced ATP and pyrimidine pools to still lower levels that would kill these cancer cells, and significantly augment the agent's tumor regression rate. Strong evidence is shown that MAP depletes tumoral ATP (15% of normal) and pyrimidines, and markedly increases the tumor regressions induced by nine different anticancer drugs in preclinical tumor models; moreover, MAP+radiotherapy produce some (25%) cures.

The key details of the necrosis and apoptosis cell death pathways, and their interrelationship is presented. Severe ATP depletion causes necrosis, whereas ATP is required for apoptosis. The obtaining of greater anticancer activity by combining ATP-depleting therapy with anticancer agents that effect apoptosis, a mode of cell death that requires ATP, is clarified.

The hypothesis has been proven at the preclinical level, and now requires clinical trial; if successful, many cancer patients will benefit. The components of MAP are off patent, and thus, there is no industrial sponsor. Support is requested for clinical supplies of MAP, and for proof-of-principle studies. The preclinical evidence supporting the concept is strong, but the ultimate validation can come only from a confirmatory clinical trial.

Background

The proposed therapeutics strategy is new and is based on recent published facts of molecular biology, as follows:
1. Most anticancer agents damage DNA which activates both the necrosis and apoptosis pathways simultaneously in the same cancer cell. (1-3)
2. DNA damage activates poly (ADP-ribose) polymerase (PARP) which depletes NAD that in turn causes ATP depletion, which, if severe, causes necrosis (4-9). Apoptosis is executed by caspases (10).
3. Necrosis is caused by severe ATP depletion. ATP is necessary for apoptosis. Despite this disparity in ATP needs, cells dead by necrosis and apoptosis are present in the same tumor treated by the same anticancer agent. (1, 11-17)
4. The necrosis and apoptosis-inducing pathways are not completely isolated entities but have an interrelationship that is evoked when intracellular endogenous inhibitors of caspases and/or genetic deletions of key caspases are present. In the absence of caspase activity, necrosis is induced unless the damage is moderate (i.e., sublethal). (18)
5. Intracellular ATP levels determine cell death fate by necrosis or apoptosis. (11-12)
6. Endogenous caspase inhibitors (21-22) and genetic deletions of caspases (19-20) may be prevalent in the heterogeneous neoplastic cell population, and switch the decision from the apoptotic to the necrotic mode of cell death. (11-12, 23-24, 18). When the anticancer agent-induced damage is sublethal, this "switch" explains the improved therapeutic results obtained by adding ATP-depleting adjuvant therapy to the anticancer agent-induced ATP-requiring apoptotic process. (18, 25)
7. Other cancer cells of lesser sensitivity to the anticancer agent for a variety of reasons (e.g. lower levels of Bax, higher levels of agent-target enzymes and/or agent-catalyzing cytochrome P-450 enzymes, etc.) are only sublethally injured and do not receive enough damage to reduce ATP to levels low enough to be insufficient to support cell viability. (18) The insight provided by these molecular biology findings suggests that biochemical modulation to further depress ATP to still lower levels than that induced by the anticancer agent alone would kill these sublethally-injured cells, augment tumor regressions, and even yield some cures.

The above information is detailed, explained, well-referenced, and clarified in diagrams in a recent publication in Cancer Research (18; copy submitted in Appendix). This molecular biology knowledge is of great relevance to this therapeutic proposal. An appropriate understanding of the scientific molecular biology background from which the ATP-depleting therapeutic opportunity emerges is important to comprehending the "why and how" ATP-depleting agents that are concomitantly administered with anticancer agents markedly improve the preclinical therapeutic results of present cancer treatment.

Interest in ATP depletion as a therapeutic tool now might be evoked by the report (14) that manipulation of cellular energy (e.g. withdrawal of substrates for glycolysis; inhibition of the mitochondrial respiratory chain) shifts the balance between apoptosis and necrosis. Or, this interest might now be stimulated by the many reports (1,11-16, 23-26) demonstrating that severe ATP depletion can function as an important effector of cell death when the apoptotic mode of cell death is prevented and replaced by the ATP-depleting mode of cell death, necrosis. However, well before the above-noted molecular biology facts were reported, the notion of affecting energy production in tumor cells had a lengthy history. Hence, there is a substantial amount of previous information available to suggest that ATP depletion might be a target for antitumor therapy. It is clear from these previous studies that the ATP-depleting strategy "works" in tissue culture, and occasionally in tumor-bearing animal studies. Thus, preclinical claims for anticancer ATP-depleting agents have been made previously, but the clinical therapeutics results have been negative or uncertain. A review of the field of anticancer ATP-depletion therapy reveals the reasons for failure. Only a "general" approach has been tried before. Usually without measurement of ATP levels, known ATP-depleting agents have been tested in vitro and in vivo with findings of tumor growth inhibition. Unfortunately, only tumor regressions (i.e., tumor cell deaths), but not tumor growth inhibition, can be measured clinically. Cell cycle events (i.e., proliferation) require a minimal ATP content to undergo proliferation (27) but intracellular ATP levels must fall to 15% of normal or below before cells lose viability (27-28). For reason of these phosphorylation relationships to cell viability and proliferation, if ATP depletion is reduced only to levels above 15% of normal, and below the minimal necessary for cell division, only proliferation arrest (i.e. tumor growth inhibition), and not tumor cell death (i.e. tumor regression), will ensue. Since only tumor regressions, but not tumor growth inhibition, can be measured clinically, preclinical studies must seek to achieve a degree of ATP depletion in cancer cells sufficient to kill (i.e., 15% of normal or below). A striking illustration that even strong depletion of ATP with potent inhibition of tumor growth is unlikely evidence to warrant expectation of a successful clinical trial is manifest in an in vitro study on cancer cells with two inhibitors of intracellular ATP levels, 6-methylmercaptopurine riboside (MMPR) and L-alanosine (29). Single agent MMPR reduced ATP levels to 49% of control levels and cell growth to 25% of control, whereas alanosine alone depleted ATP to only 63% of control and cell growth to 59% of control. However, the combination of alanosine+MMPR effected very substantial depletion of the ATP pool to 34% of control and completely inhibited tumor growth. Nevertheless, normal cell growth resumed immediately after removing the drugs from the medium (29). Clearly, although both impressive depletion of ATP (34% of normal), and complete inhibition of tumor growth was achieved, this ATP-depleting combination of two ATP-depleting agents was unable to achieve the all-important goal of effecting tumor cell deaths in the preclinical tumor. It is, therefore, doubtful that a clinical trial of this combination would demonstrate discernible clinical activity (i.e., cause tumor regressions, the only clinical endpoint for documenting anticancer activity).

Our ATP-depleting Background—Turning now to our own background of ATP-depleting agents and their effect on preclinical tumors, a combination of ATP-depleting agents appears required to reduce tumoral intracellular ATP content to the severely low levels of $\geq 15\%$ of normal which cannot sustain cell viability (27-28). As presented earlier, all cytotoxic anticancer agents produce a substantial degree of ATP depletion in their sublethally-injured cancer cells due to damage to the glycolytic generation of ATP by the activation of poly (ADP-ribose) polymerase following anticancer agent-induced DNA damage (18). Therefore, an anticancer agent that is cytotoxic to the particular tumor being treated is considered part of our ATP-depleting regimen. Anticancer agents produce a tumor regression rate by killing cancer cells by either necrosis or apoptosis, but they also effect sublethal injury to less sensitive cancer cells from which they will recover, grow again and kill the patient. It is the anticancer agent-induced reduction of ATP to low, but still life-sustaining levels in sublethally-injured cancer cells that creates the therapeutic opportunity for biochemical modulation by ATP-depleting agents to further deplete ATP to lethal-inducing (i.e., $\geq 15\%$ of normal) ATP levels (27-28) before the sublethally-injured cells can recover. Therefore, our ATP-depleting therapeutic strategy requires that a combination of ATP-depleting agents is administered concomitantly with the cytotoxic anticancer agent.

Our combination of ATP-depleting agents includes 6-methylmercaptopurine riboside (MMPR), known to inhibit de novo purine biosynthesis (30-31) and thereby limit adenine supplies for ATP production, and 6-aminonicotinamide, known to inhibit glycolytic production of ATP (32). The double combination of MMPR+6-AN can successfully achieve cancer cell-killing ATP levels of .ltoreq.15% of normal (Table 9, Group 4, 48 hours; ref.18). The de novo pyrimidine synthesis inhibitor, PALA, was also added to the ATP-depleting combination. PALA, in low, non-toxic dosage can selectively lower pyrimidine levels in tumors (33). The triple combination of MMPR+6-AN+PALA (acronym: MAP) is concomitantly administered with the cytotoxic anticancer agent. One reason for adding a pyrimidine antagonist is that, in high dosage, MMPR alone had been reported (34) to decrease pyrimidine ribonucleotide concentrations (probably because the MMPR-lowered ATP levels limited the anabolic conversion of pyrimidines to ribonucleotides). However, the primary reason for including PALA is that cytotoxic anticancer agents cause mitochondrial damage in sublethally-injured cancer cells. Pyrimidine de novo synthesis is functionally linked to the respiratory chain in the inner mitochondrial membrane by mitochondrial-bound dihydroorotate dehydrogenase, the fourth enzyme of de novo pyrimidine synthesis. PALA should further lower the reduction of pyrimidine levels due to the mitochondrial damage effected by an anticancer agent-induced apoptotic biochemical cascade in surviving but sublethally-injured cancer cells. It had been shown previously that cells that had been completely depleted of mitochondria become pyrimidine auxotrophs because of the deficiency of the mitochondrial respiratory-chain dependent dihydroorotate dehydrogenase (35). A minimal level of pyrimidine nucleotides is essential to sustain cell life. Pyrimidine nucleotides serve essential functions in nucleic acid metabolism and sugar nucleotide formation for glycosylation of proteins and lipids. It is, therefore, not surprising that severe inhibition of pyrimidine biosynthesis occurs due to PALA+the loss of the dihydrooratate dehydrogenase enzyme in the damaged mitochondria of cancer cells sublethally-injured by the anticancer agent. However, even without a cytotoxic anticancer agent, MAP alone causes a marked decrease of pyrimidine nucleotides due to PALA+high-dose MMPR, as well as to severe ATP depletion (15% of normal, group 4, 48 hours, Table 9) due to MMPR+6-AN. Severely depleted ATP pools inhibit the salvage pathway formation of pyrimidine di-and triphosphates at the kinase step. UTP pools in in vivo MAP-treated tumors were greatly reduced to 14% of normal (36).

Anticancer Effects of MAP Alone—For all of the above biochemical relationships, the three agents—MMPR, PALA and 6-AN—were evaluated alone, in various double combinations, and as a triple combination against advanced breast cancers ($CD_8F_1$) in mice. Three published pooled experiments (Table 10) demonstrated that neither the maximum tolerated dose of MMPR alone, 6-AN alone, nor the double combination of PALA+6-AN (respectively, Groups 1, 2 and 3, Table 10) produced cell kill (37). There were no partial regressions of tumors (PR, .gtoreq.50% tumor shrinkage in the volume of the initially measured tumor), but tumor growth was inhibited in these groups as compared with saline controls. Table 9 records that MMPR alone (Group 1) and 6-AN alone (Group 2) depress tumor ATP levels 48 hours after treatment to 34% and 69%, respectively, compared with saline-treated control tumors. These are ATP levels compatible with the tumor growth inhibitions produced by MMPR alone and 6-AN alone in Table 10. PALA does not affect ATP depletion, and in the low dosage that was administered reduces pyrimidine biosynthesis but does not have anticancer activity (33). Hence, the combination of low dose PALA+6-AN (Group 4, Table 10) only inhibited tumor growth due to the 6-AN which, alone, only reduced ATP to 69% of normal (48 hours, Group 2, Table 9).

The double combination of MMPR (a strong ATP depleter, 34% of normal, 48 hours, Group 1, Table 9) plus PALA (which is devoid of an ATP-depleting effect) produced a very few partial tumor regressions, 7% PR (Group 5, Table 10). The MMPR-induced depletion of ATP to 34% is an average; hence, a few individual tumors in the group of 28 tumor-bearing mice (specifically, 2/28) likely have an ATP level $\leq 15\%$ of normal, a level shown to be insufficient to sustain cell viability (27-28).

In the series of three pooled experiments of Table 10, the double combination of MMPR+6-AN (Group 6, Table 10) produced a 17% PR (37) an increase over the 7% PR of MMPR+PALA. The MMPA+PALA average ATP level is only 34% of normal. The improved therapeutic result with MMPR+6-AN is explained by the MMPR+6-AN-induced cell-killing average ATP level of 15% of normal (Table 9, Group 3, 48 hours). Apparently, a few more individual tumors in this group of 29 tumor-bearing mice (specifically, 5/29) had ATP levels that were 15% of normal or below.

Note that the MMPR+6-AN induced ATP level of 15% of normal is, as expected, unchanged (still 15%) by the addition of PALA to MMPR+6-AN (Group 4, 48 hours, Table 9). However, in the presence of this severe limitation to ATP availability, the addition of pyrimidine depletion by PALA to the MMPR+6-AN combination (i.e., MAP) enhanced the PR rate to 61% (Group 7, Table 10). The limited availability of ATP for the conversion of the PALA-reduced pyrimidines to pyrimidine nucleotides doubtless explains the improved therapeutic result.

Pyrimidine depletion makes a substantial contribution to the MMPR+6-AN ability to effect more cancer cell deaths. (i.e., greater tumor regressions) due to the presence of severe ATP depletion. Note that PALA alone reduces tumor pyrimidine levels, but neither reduces tumor ATP levels nor inhibits tumor growth, and that PALA+MMPR causes a substantial ATP reduction (34% of normal) but only effects inhibition of tumor growth. MMPR+6-AN and MMPR+6-AN+PALA effect the same degree of severe ATP depletion, but the number of tumor regressions are much improved by treatment with the triple combination of MAP. It is the severe depletion of ATP levels (15% of normal) that limits the conversion of pyrimidines to nucleotides (UTP pools in MAP-treated tumors are only 14% of normal; (36), and thereby appreciably augments the anticancer activity of MMPR+6AN+PALA (61% PR, Table 10) over that of MMPR+6-AN (17% PR, Table 10). Since anticancer agents reduce ATP and pyrimidines, two metabolites that are essential for cell viability, to low levels in sublethally-injured cancer cells, all cytotoxic anticancer agents create a therapeutic opportunity for biochemical modulation (e.g., MAP) to further reduce them to lower levels insufficient to sustain the recovery of these injured cancer cells.

Preclincial Therapeutic Results of MAP+Various Anti-cancer Agents—MAP+various anticancer agents was evaluated in advanced tumor-bearing mice with a variety of tumor types (murine breast cancer, colon cancer, leukemia, and human breast cancer xenografts. The data to be presented is largely in first passage subcutaneous transplants from the $CD_8F_1$ breast tumor model included previously in the National Cancer Drug Screening Program (38). The transplants are made from a tumor brei made by mixing the cancer cells of three or four single spontaneous, autochthonous $CD_8F_1$ breast tumors. All spontaneous tumors, whether human or murine, have a heterogeneous neoplastic cell population. Each experiment is from a different brei (i.e., each from a different group of 3-4 spontaneous tumors) and, therefore, each transplant group contained a different number of chemotherapeutically sensitive and/or resistant tumor cells. Hence, the individual transplants in each experiment developed from a single brei that, although common to all the mice in that experiment, had a neoplastic cell population that was somewhat different from that in another experiment, resulting in some quantitative differences between experiments. However, each experiment has its own control, each tumor-bearing mouse within the same experiment carries the same transplant, and the therapeutic results are quantitatively relevant within individual experiments, as are trends among experiments.

TABLE 9

Effect of MMPIR + 6-AN + PALA (MAP) on tumor ATP pools in $CD_8F_1$ mice[d].

| Group | Treatment | 6 HW[b] ug A TPI mq ± S.E | % Saline Control | 24 HR[a] ug A TPI mg ± S.E | % Saline Control | 48 HR[a] ug A TPI mg ± S.E | % Saline Control | 72 HR[a] uglA TP mg ± S.E | % Saline Control |
|---|---|---|---|---|---|---|---|---|---|
| 1 | MMPR$_{150}$ | 3.3[c] ± 0.32 | 47 | 3.3[b] ± 0.96 | 47 | 1.6[b] ± 0.59 | 34 | 9.0[d] ± 2.4 | 127 |
| 2. | 6-AN$_{10}$ | 5.5[b] ± 0.21 | 77 | 5.3[b] ± 0.136 | 75 | 4.9[b] ± 0.16 | 69 | 12.0[c] ± 3.9 | 169 |
| 3. | MMPR$_{150}$ + 6-AN$_{10}$ | 4.1[b] ± 0.49 | 58 | 2.2[b] ± 0.08 | 31 | 1.1[b] ± 3.6 | 15 | 16.0[c] ± 3.6 | 225 |
| 4. | MAP | 3.9[b] ± 0.11 | 55 | 2.3[b] ± 0.31 | 32 | 1.1[b] ± 0.14 | 15 | 8.1[c] ± 0.7 | 114 |

[a]Mean ± S. E. of 10 tumors/group (11 experiments)
[b]Statistical comparison to group 1 (saline control), Significant = P value less than or equal to 0.05
[c]Mean ± S.E. of 6 tumors group (4 experiments)
[d]Subscript = mg/kg body weight; i.p. injections; 1st passage tumor transplants of $CD_8F_1$ spontaneous breast tumors.

TABLE 2

Combination Therapy with N-(Phosphonacetyl)-L-Aspartate (PALA), 6-Aminonicotinamide (6-AN), and 6-Methyl-Mercaptopurine riboside (MMPR)

| Treatment* | | Tumor wt (mg) | | Partial regression | | Percentage body wt change | Dead/total |
|---|---|---|---|---|---|---|---|
| 1. | Saline | 5,301 | } $p = 1.2 \times 10^{-11}$ | 0/29 | | +17 | 4/29 |
| 2. | MMPR$_{175}$ | 505 | | 0/30 | | -3 | 0/30 |
| 3. | 6-AN$_{25}$ | 1,369 | | 0/30 | | -25 | 5/30 |
| 4. PALA$_{100}$ $\xrightarrow{18\ hr}$ | 6-AN$_{10}$ | 2,765 | } $p = 0.03$ | 0/30 | | -3 | 10/30 |
| 5. PALA$_{100}$ $\xrightarrow{18\ hr}$ | MMPR$_{150}$ | 454 | | 2/28 (7%) | | -14 | 2/28 |
| 6. | 6-AN$_{150}$ + MMPR$_{150}$ | 261 | } $p = 0.01$ | 5/29 (17%) | } $p = <0.01$ | -11 | 0/29 |
| 7. PALA$_{100}$ $\xrightarrow{18\ hr}$ | 6-AN$_{10}$ + MMPR$_{150}$ | 100 | | 17/28 (61%) | | -22 | 0/28 |

Pooled data from three experiments in first-generation CD8F1 advanced breast tumors (Experiments 1164, 1170, 1171) averaging 150 mg when therapy was initiated.
*Three courses of the indicated treatment were administered with a 1-week interval between courses. Subscripts = mg/kg. Observations 5 days after third course of treatment.

Anticancer Effect of MAP Alone in Spontaneous Murine Breast Tumors (Ref. 39)—Table 11 records that MAP produced a partial tumor regression rate of 38% in mice bearing large spontaneous, autochthonous breast tumors. There were 24 partial tumor regressions in 64 surviving mice with acceptable toxicity (4% mortality, 3 deaths in 67 treated mice). Spontaneous regression of these spontaneous breast cancers has never been observed.

Fura+MAP (Ref. 39)—Table 11 documents a statistically significant enhancement of the partial tumor regressions (PR rate) from 38% to 67% by the addition of FUra at 75 mg/kg to MAP in mice bearing spontaneous autochthonous tumors. FUra alone at 75 mg/kg produced less than 5% regressions of spontaneous autochthonous breast tumors, and alone at its MTD of 100 mg/kg, produces no more than a 20% PR rate. Thus, the combination of MAP+FUra produces a markedly enhanced PR rate (67%).

TABLE 11

Therapeutic comparison of MAP, with and without the addition of 5-fluorouracil (FUra), in mice bearing spontaneous, autochthonous CD$_8$F$_1$ breast tumors[2]

| Treatment | Percent Body Weight Change | Dead/Total | Partial Regressions |
|---|---|---|---|
| 1. MAP | -10 | 3/67(4%) | 24(38%) |
| 2. MAP + Fura$_{75}$ | -10 | 5/66(7%) | 41(67%) |

[a]Pooled data: Experiments R536, R537, R538, R539, R540, R541, Spontaneous, autochthonous CD8F1 breast tumors averaging 260 mg of initiation of treatment.
[b]The indicated treatment was administered at 10-11 day intervals. Subscripts refer to doses in mg/kg. Observations were recorded 6 weeks after initiation of treatment (i.e. approximately 9 days after the fourth course of treatment)

Adriamycin+5-Fluorouracil (FU)+MAP (Ref. 40)—Table 12 records the averaged results of six separate experiments in advanced 1$^{st}$ generation breast tumors. MAP (Group 1) has a PR (partial tumor regression) rate of only 2%, MAP+FU (Group 2) a 60% PR, MAP+Adria (Group 3) a 60% PR, and the overall combination of MAP+FU+Adria (Group 4) a 79% PR, which is statistically significant when compared to Group 2 (PMA+FU) or to Group 3 (MAP+Adria). Various dosage ratios of FU+Adria (without MAP) produced only tumor growth inhibition (no regressions), or a markedly inferior rate of tumor regression compared with the MAP+FU+Adria combination, even when high doses of FU and Adria (doses producing excessive mortality) were employed as a double combination.

TABLE 12

Enhanced therapeutic activity of 5-FU plus Adr in conjunction with MAP in CD$_8$F$_1$ mice bearing advanced first passage breast tumors[2]

| Treatment | % Body w't change | Regressions/survivors[c] | Dead/total |
|---|---|---|---|
| 1. MAP | -17 | 1 PR/45 = 2% | 5/50 = 10% |
| 2. MAP-FU$_{75}$ | -19 | 30 PR + 1 CR/52 = 60% | 7/59 = 12% |
| 3. MAP-Adr$_6$ | -25 | 33 PR + 1 CR/57 = 60% | 3/60 = 5% |
| 4. MAP-FU$_{75}$ + Adr$_6$ | -25 | 41 PR + 5 CR/58 = 79% | 2/60 = 3% |

[a]Pooled results: experiments 2718F, 2777F, 2796F, 2813F, 2815M, 2816M.
[b]Three courses with a 10-11 day interval between courses. Observations 7 days after last treatment. Subscripts = mg/kg
[c]CR (complete regression), PR (partial regression), i.e., reduction in tumor size of 50% or greater, when compared with tumor size at initiation of treatment. (1 st passage from brei of 4 spont. tumors, are more resistant then individual spont. tumors.)

MAP+taxol (Ref. 41)—Table 13 documents a significantly increased PR rate of 56% in the MAP+taxol (Group 2) tumor-bearing animals compared to MAP alone (Group 1) with a PR=5%. The weight loss was essentially identical in the two groups, and note that weight loss never produces tumor regressions. Taxol alone at its MTD (80 mg/kg q 10-11 days×3) produces statistically significant inhibition of tumor growth compared to saline-treated tumors, but no tumor regressions. The superior antitumor activity of the MAP+taxol combination was achieved with a dose of taxol (25 mg/kg) that was less than one-third that of the MTD of taxol alone (80 mg/kg).

TABLE 13

Enhanced activity of paclitaxel (taxol) when administered following MAP + ATP-depleting chemotherapy in the treatment of advanced first passage CD8FI marine breast tumors[a]

| Treatment | Body weight change % | Dead/total | PR/survivors |
|---|---|---|---|
| 1. MAP | −16 | 6/49 (12%) | 2/43 (5%) |
| 2. MAP + taxol$_{25}$ | −18 | 0/48 (0%) | 27/48 (56%)[c] |

[a]PALA administered i.p. 17 h before i.p. MMPR (150 mg/kg) + 6-AN (10 mg/kg) and paclitaxel (25 mg/kg) administered i.p. 2.5 h after MMPR + 6-AN. Subscript mg/kg. Observations recorded 6 days after the third course of treatment.
[b]Pooled results: exps 2659F, 2662F, 2675F with initial tumor weights averaging 180, 172, 130, 155 and 122 mg. respectively.
[c]Statistical significance of PR rate between group 1 and 2: p < 0.001.

MAP+Phenylalanine Mustard (PAM: Ref. 42)—Table 14 documents the pooled results of three experiments. The addition of MAP to PAM (Group 2) markedly increased the PR rate to 74% from 14% with MAP alone. PAM alone at 18 mg/kg in the same schedule did not produce tumor regressions in this series of experiments. Again, as in all experiments combining MAP with an anticancer agent, note that the superior antitumor activity of the combination is achieved with a low dose of the anticancer agent (e.g., PAM is at only 7 mg/kg in combination with MAP).

TABLE 14

Therapeutic evaluation of phenylalanine mustard (PAM) administered following MAP.

| Treatment | Percent Body Weight Change | Dead/total | Partial Regressions |
|---|---|---|---|
| 1. MAP | −17 | 2/30(7%) | 4/28(14%) |
| 2. MAP + PAM$_7$ | −21 | 3/30(10%) | 20/27(74%)[c] |

[a]Pooled results: Exps 2489F, 2541 M, 2552 M. 1 st generation tumor transplants of CD8F1 spontaneous, autochthonous breast tumors averaging 125 mg when treatment initiated. Three courses of the indicated treatment were administered with a 10-11 day interval between courses. Observations were recorded one week after the third course of treatment. Note that PAM alone, in doses from 7 to 18 mg/kg, did not produce any tumor regressions in this series of experiments.
[b]PR = partial tumor regressions (No. of regressions/survivors).

Summary of Preclinical Therapeutic Results with MAP+ Cancer Chemotherapy—MAP+each of nine mechanistically-different apoptosis-inducing anticancer agents was administered to advanced tumor-bearing mice with a variety of tumor types (murine breast cancers, colon tumors and leukemia, and human breast cancer xenografts). MAP dramatically enhanced treatment of preclinical tumors with doxorubicin, taxol, cisplatin, 5-fluorouracil, phenylalanine mustard, cyclophosphamide, mitomycin, etoposide and radiotherapy (18). The antitumor results demonstrated safe and impressive significant augmentation of tumor regression, including complete regressions. ("Cures" (25%) were produced with MAP+radiotherapy in our usual schedule of three intermittent courses; the tumor-bearing mice were followed for over 380 days.)

Moreover, the addition of MAP to combination chemotherapy with FU+Adria was safe without need for dose reduction, and yielded enhanced antitumor activity, including CRs not previously achieved. The results encourage the prospect of the safe addition of MAP to combination chemotherapy with the likelihood of even greater anticancer results (e.g., after increased CRs comes cures). The therapeutic activity measured in all of our studies employed the stringent clinical criterion of tumor regression (i.e., 50% or greater chemotherapy-or radiotherapy-induced decrease in tumor size).

MAP can cause body weight loss. However, this weight loss is not accompanied by diarrhea or by histopathologic changes in organs (such as the intestine). It was demonstrated to be due to severe anorexia for 3-4 days after each of the three courses of intermittent chemotherapy. Treatment-conditioned weight loss due to failure to eat or drink is usual for animals receiving intensive chemotherapy, and has been found by other investigators (Drs. Beverly Teicher and Emil Frei, a personal communication). Importantly, weight loss, which can indeed cause inhibition of tumor growth, does not produce tumor regression. We have done separate experiments (unpublished) demonstrating that weight loss does not cause tumor regression. This fact is also clearly apparent in some of our published studies with ATP-depleting therapy. For example, in a pooled series of six experiments, Table 12, two groups have similar weight loss (−17% and −19%), but one group has 60% tumor regressions and the other has only 2% tumor regressions. Also, in that same series of experiments, two other groups have identical weight loss (−25%) but different tumor regression rates (60% versus 79%) that are statistically significant. (Weight loss would not be a problem in patients who, unlike animals, can be persuaded to drink and eat, or can be supported intravenously).

ATP Depletion in Tumors with Methylthioadenosine Phosphorylase (MTAP) Deficiency—MTAP, an enzyme involved in purine metabolism is present in normal tissues, but frequently is deleted (deficient) in leukemias, brain tumors, non-small cell lung cancers, breast cancers, melanomas, and pancreatic cancers (44-45), Methylthioadenosine is produced during polyamine synthesis and cleaved to adenine (and 5-methylthioribose-1phosphate) by MTAP. The adenine is reconverted to AMP and then to ATP. The deletion of the MTAP gene in many tumors results in the inability of these cancer cells to salvage adenine; therefore, the ATP pools in these cells must be marginalized. L-Alanosine, a potent inhibitor of de novo AMP synthesis has demonstrated anticancer activity in vivo in MTAP-negative cell lines (46).

An examination of MTAP expression in ten human soft tissue sarcoma cell lines found MTAP not detectable in four of the ten cell lines. These four cell lines were sensitive to L-alanosine. The addition of the de novo purine synthesis inhibitor, MMPR, further enhanced the cells lacking MTAP activity to L-alanosine.

These results provide the basis of selective therapy using L-alanosine+MMPR to treat patients with soft tissue sarcomas, and are another example of the therapeutic utility of the ATP-depleting strategy.

Proposed Clinical Trial of MAP—The MSKCC proposed clinical trial of MAP has potential for gain in patient survival time, and the possibility of increased cures. Single agent 6-AN has been previously administered in three Phase 1 clinical trials in patients with disseminated cancer (47-49). 6-AN toxicity takes two clinical forms; at low dose a mixed B complex vitamin deficiency, and at high dose CNS toxicity. The FDA has informed us they would waive further preclinical toxicity studies since there is previous clinical experience with 6-AN. Of note in these studies, 6-AN was given daily, whereas the proposed MSKCC clinical trial for MAP is an infrequent intermittent schedule q 2 weeks. A clinical trial is necessary to either confirm or not the successful preclinical findings with an intermittent schedule of MAP. The MSKCC clinical investigators (Ilson, D, Koutcher, J, Martin, D, O'Reilly, E, Kemeny, N, Norton, L, Ochoa, M, Jr., Saltz, L, Schwartz, G, Scher, H, Spriggs, D, Sternberg, S, Reuter, V, Hudis, C, Gorlick R, and Bertino, J.) who wish to evaluate a MAP clinical protocol at MSKCC are well-experienced at conducting safe clinical trials. The preclinically proven biochemical modulatory concept of ATP-depletion as therapy, if substantiated clinically, should be applied to patient care as soon as possible. RAID assistance can enable entry into the clinic of a promising novel therapeutic strategy that is not otherwise likely to receive a timely test.

It is the preclinically-proven ATP-depleting modulatory concept that requires appropriate clinical exploration, and not specific drugs (e.g. MAP), Thus, the clinical trial need not necessarily be done with the MAP regimen to prove the therapeutic value of the ATP depletion concept at the clinical level. However, the MAP regimen seems the best choice, not only for the scientific molecular biology findings already given, and the successful preclinical tumor regression data with MAP, but because a MAP clinical trial should be completed in a relatively short time frame. All three of the MAP drugs have been independently evaluated clinically, and therefore, their toxicities and some schedules are known. Cancer patients have received MMPR+PALA combined in a single regimen with a concomitantly administered anticancer drug, 5-fluorouracil (75). (The combination of all three drugs (MAP) has never been evaluated). Thus, evaluating the MAP regime in the clinic merely requires integration of 6-AN into the clinically established MMPR+PALA regimen. Clearly, less time would be required for evaluating MAP in the clinic compared to new agents.

The very potent, but demonstrated safe, ATP-depleting effects of the infrequently intermittently administered (q10-11 day) MAP regimen in advanced preclinical tumors, and the strong preclincal antitumor effects of MAP (i.e. enhanced tumor regressions including some cures), with the mechanism of action now established that ATP depletion can be an important necrotic-apoptotic death factor (26), has engaged the interest of the MSKCC clinical staff and the writing of a MSKCC MAP clinical protocol. Funding for clinical supplies of MAP is needed. The MAP clinical trial should be begun (and completed) as soon as possible. If the trial is confirmatory many cancer patients can be markedly benefited by MAP.

Clinical Supplies of MAP—A major problem with obtaining clinical supplies of MAP is that its components (MMPR+6-AN+PALA) are "old" drugs that are all off patent. Usually the cancer drugs that go into clinical trial are sponsored by pharmaceutical companies. Their drugs have patents, and are specially formulated for clinical use. In contrast, none of the MAP components are still patented, and none are available in a clinical formulation.

Hypothesis

Most anticancer agents are DNA-damaging, kill cancer cells by inducing necrosis or apoptosis, and leave a residual problem—cancer cells of lesser sensitivity are only sublethally injured, recover, and re-grow to kill the patient. The sublethal cellular damage by the anticancer agents reduces ATP and pyrimidines, two metabolites that are essential for cell viability, to low levels, thereby creating a therapeutic opportunity for their further reduction by biochemical modulation to lower levels insufficient to sustain the recovery of these injured cells. Our hypothesis that adjuvant therapy—a combination of two ATP-depleting compounds (6-methylmercaptopurine riboside, MMPR, and 6-aminonicotinamide, 6-AN), and an inhibitor of pyrimidine synthesis, PALA; all three agents collectively referred to by the acronym, MAP—administered concomitantly with standard anticancer agents would increase cancer cell kill, enhance tumor regressions, lengthen survival, and even produce some cures, has been proven at the preclinical level. This RAID application provides a preclinically proven hypothesis-driven therapeutic strategy with the opportunity for hypothesis-based testing in the clinic. This testing will include evaluation of tumor response (with and without MAP) and "proof-of-principle" testing (e.g., ATP and pyrimidine nucleotide measurements in tumors before and after therapy).

The RAID Brochure stipulates that "Proposals must meet the Developmental Therapeutics Program's criteria for targeted therapies "that are discussed in a recent NCI publication "(51). This proposal meets these criteria. The article states that "the elements for success in cancer drug discovery efforts - - - first, investigative efforts establishing a potential drug discovery target can have as their focus any aspect of cancer cell biology that may create a vulnerability in the cancer cell . . . . Molecular targets that comes with a 'mature' biologic pedigree as likely affecting important aspects of cell function. (51).

Our mechanism-based targets of ATP depletion and pyrimidine depletion have that 'mature' biologic pedigree. Our Background section presents findings that cytotoxic anticancer agents create a vulnerability in the cancer cell to our mechanism-based targets of ATP depletion and pyrimidine depletion.

The NCI publication (51) further notes of the need for "molecular and imaging assays of drug effects on specific targets in proof of principle laboratory models . . . (and that the) . . . physiological effects of the drug on its target need to be assessed in vivo, and correlated with the . . . (therapeutic) . . . effect".

Our Background section and a number of our publications (e.g., 36, 39, 43, 52-53) report NMR and HPLC ATP and pyrimidine measurements in vivo demonstrating that MAP depletes these target metabolites in the treated cancer cells and correlate these findings with enhanced therapeutic results. If RAID provides the opportunity for the hypothesis-based testing of MAP in the clinic we will do these assays and make the appropriate correlations in proof-of-principle clinical studies.

Specific Requests

Clinical supplies of MMPR, 6-AN, and PALA. Support for NMR techniques in cancer patients, pre-and post-treatment, to detect changes in ATP and 6-phosphogluconate, 6-PG, in large tumors (at least 3×3×3). Support for HPLC ATP measurements on sequential biopsies of accessible tumor tissue before and after treatment. 6-PG will be measured by published methods (Methods of Enzymatic Analysis (2 sided.), H. V. Bergmeyer (ed.) Vol. III, pp. 1238-1243, New York: Academic Press, 1974. 6-PG measurements following the administration of 6-AN will establish the effective dose of 6-AN. The applicant institution, Memorial Sloan Kettering Cancer Center (MSKCC) will conduct the clinical trial.

Justification

This proposal represents a particularly innovative approach to the treatment of cancer. The MAP drugs per se are not innovative. It is the concept of employing biochemical modulation with a combination of at least two ATP-depleting agents plus a pyrimidine antagonist as adjuvant therapy to kill cancer cells sublethally injured by anticancer agents that is a novel and promising approach to cancer treatment.

The notion of affecting energy production in tumor cells has a long history. The "general" approach was to administer an ATP-depleting agent without measurements of the level of ATP depletion achieved, without recognition that cell kill depended on achieving a severe degree of ATP depletion, and without recognition that the appropriate target for cell kill by ATP-depleting agents would be the cancer cells sublethally injured by anticancer agents because ATP depletion was ongoing as a result of the sublethal injury. Our ATP-depleting therapeutic strategy differs from that of the past, as follows:

1. The ATP-depleting agents aim to reduce ATP levels in cancer cells severely (15% of normal or below) because these are levels that cannot sustain cell viability.
2. A combination of ATP-depleting agents is required to achieve severe ATP depletion because there are many generating paths to ATP.
3. The ATP-depleting agents are administered concomitantly with cytotoxic anticancer agents because the anticancer agents sublethally-injured cancer cells have reduced ATP levels (although not to low levels insufficient to sustain cell viability).
4. An inhibitor of de novo pyrimidine biosynthesis is also administered to further reduce the pyrimidine depletion in the sublethally-injured cancer cells.

Severe pyrimidine depletion has been shown to markedly enhance cancer cell deaths in the presence of severe ATP depletion. Pyrimidine depletion occurs in the sublethally-injured cancer cells because mitochondria are damaged and the de novo pyrimidine biosynthesis pathway is partly housed in mitochondria. Anticancer agents reduce ATP and pyrimidines, two metabolites that are essential for cell viability, to low levels in sublethally-injured cancer cells, and thereby create a therapeutic opportunity for biochemical modulation to further reduce them to lower levels insufficient to sustain the recovery of these injured cancer cells.

This proposal represents a particularly promising approach to improving the treatment of cancer. The proposed clinical study is relevant to the problem of residual disease following treatment of cancer, and has the potential for high impact. The proposed adjuvant treatment to cytotoxic therapy could result in the elimination of those residual cancer cells left after present treatment failures, and thus yield cures instead of temporary remissions. In the context of metastatic disease, this treatment could markedly enhance the efficacy of available chemotherapeutic agents with reduction of the dose of the cytotoxic agent, and reduction of toxicity with gain of efficacy. This clinical study, if successful, would enhance both initial adjuvant chemotherapy aimed at curing advanced metastic disease, and also treatment of advanced metastatic disease. The reason is that all the present therapeutically-induced partial tumor regressions, and/or complete tumor regressions that eventually recur, are vulnerable to further ATP/pyrimidine depletion.

It has been stated, "In almost every instance, concepts of chemotherapy derived from experimental tumor model systems have been applicable to the clinical situation—if and when these concepts have been tested appropriately. (54). The proposed project's rationale, supporting molecular biology background, and markedly enhanced preclinical tumor regression data are strong, justify a clinical trial, provide important guidelines for a successful clinical trial, and warrant the expectation that an appropriate clinical trial will be conducted.

Uniqueness

The RAID instructions request a discussion by the applicant of related or similar molecules already under development by NCI or known to be in development under industrial sponsorship, and why the NCI should undertake development in the light of this. MMPR, 6-AN and PALA are all off patent and not available in a clinical formulation. Thus, there is no pharmaceutical company sponsorship. The proposed innovative approach will likely not be explored for a long time without RAID assistance to obtain clinical supplies of these specific drugs. Time lost in terms of the clinical potential for treatment advance in patient care, gain in patient survival time, and the possibility of increased cures, is prohibitive.

It is the preclinically-proven biochemical modulatory concept that requires appropriate clinical trials, and not specific drugs. If clinically confirmed, better and patentable analogs of MMPR, 6AN, and PALA likely can, and will be, provided by the pharmaceutical industry. New agents that accomplish ATP and pyrimidine depletion will be therapeutically applicable to enhancing the therapeutic anticancer activity of all clinically important anticancer agents. This market is larger and more attractive than finding a new drug for a target interaction that adversely affects only a relatively few cancer.

A clinical trial that awaits the development of patentable potential candidate drugs to inhibit two or more pathways to ATP production must also await the preclinical development time to define the pharmacologic interrelationship between two or more patentable potential candidate drugs. The latter developmental research has already been done with MMPR and 6-AN. Except for clinical supplies, the proposed MMPR+6-AN+PALA regimen is ready now, has engaged the interest of clinical investigators at MSKCC and they have written a clinical protocol in which they participate as co-investigators. Importantly, a clinical trial with these agents should be completed in a relatively short time. All three drugs have been independently evaluated clinically, and therefore, their clinical toxicities and some schedules are known. Also, cancer patients have safely received MMPR+PALA combined in a single regimen with a concomitantly administered anticancer drug, 5-fluorouracil (50). Thus, evaluating the MAP regimen (i.e., the acronym for MMPR+6-AN+PALA) in the clinic merely requires integration of 6-AN into the clinically-established MMPR+PALA regimen. Clearly, less time would be required for evaluating MAP in the clinic compared to developing new agents.

The RAID brochure states, "it is intended to remove the most common barriers between laboratory discoveries and clinical trials . . . (when) . . . a new approach is a viable candidate for expanded clinical evaluation". This new "MAP" approach is, in the words of the NCI brochure, "NOT likely to be explored without RAID assistance", and particularly not in the desirable shortest time frame that the availability of MAP supplies would permit for a clinical trial of the successful laboratory discoveries. Obviously, the earlier clinical trial is done, if successful, the more cancer patients will benefit. The NCI should undertake development of clinical supplies of MAP because no one else will do so, the total data are compelling for a clinical trial, and the ultimate rejection or validation for the concept can come only from an appropriate clinical trial.

APPENDIX

1. Martin, DS, Bertino, JR, and Koutcher JA. Perspective: ATP depletion+ pyrimidine depletion can markedly enhance cancer therapy - Fresh insight for a new approach. Cancer Res 60:6776-6783, December 15, 2000.

2. Martin DS, Spriggs, D. and Koutcher JA. An ATP-depleting strategy with 6-aminonicotinamide (6-AN) alone, or in combination with 6-methylmercaptopurine riboside (MMPR) and PALA, markedly enhances cisplatin-induced anticancer activity. Apoptosis: Vol. 6 pp. 125-131, updated 2001.

REFERENECES

1. Shimizu, S., Equchi, V., Kamike, W., Itoh, Y., Hasegawa, J., Yamabe, K., Otsuid, Y., Matsuda, H., and Tsujiimoto, Y. Induction of apoptosis as well as necrosis by hypoxia and predominant prevention of apoptosis by bcl-2 and bcl-x. Cancer Res., 56:2161-2166, 1977.
2. Amarante-Mendes, G. P., Finucane, D. M., Martin, S. J., Cotter, T. G., Salvesen, G. S., and Green, D. R. Anti-apoptotic oncogenes prevent caspase-dependent and independent commitment for cell death. Cell Death Differ., 5:298-306, 1998.
3. Huschtscha, L. I., Anderson, C. E., Bartier, W. A., and Tattersall, M. H. N. Anti-cancer drugs and apoptosis. In: M. Lavin and D. Walters (eds), Programmed Cell Death, the Cellular and Molecular Biology of Apoptosis, pp. 269-278. New York: Harwood Academic, 1993.
4. Berger, N. A., and Berger, S. J. Metabolic consequences of DNA damage: the role of poly (ADP-ribose) polymerase as mediator of the suicide response. In: L. Grossman and A. C. Upton (eds.), Mechanisms of DNA Damage and Repair, pp 357-363. New York: Plenum Publishing Corp., 1986.
5. Tanizawa, A., Kubota, M., Hashimoto, H., Shimizu, T., Takimoto, T., Kitoh, T., Akiyama, Y., and Mikama, H. VP-16-induced nucleotide pool changes and poly (ADP-ribose) synthesis: the role of VP-16 in interphase death. Exp. Cell Res., 185: 237-246, 1989.
6. Carson, D. A., Seto, S., Wasson, B., and Carrera, C. DNA strand breaks, NAD metabolism programmed cell death. Exp. Cell. Res., 164:273-281, 1986.
7. Schraufstaffer, I. U., Hinshaw, D. B., Hyslop, P. S., Spragg, R. H., and Cochrane, C. G. Oxidant injury of cells DNA strand-breaks activate polyadenosine diphosphate polymerase and lead to depletion of nicotinamide adenine dinucleotide. J. Clin. Investig., 77:1312-1320, 1986.
8. Gaal, J. C., Smith, K. R., and Pearson, C. K. Cellular euthanasia mediated by nuclear enzyme: a central role for nuclear ADP-ribosylation in cellular metabolism, Trends Biochem. Sci., 12: 129-132, 1987.
9. Marks, D. I., and Fox, R. M. DNA damage, poly (ADP-ribosyl)ation and apoptotic cell death as a potential common pathway of cytotoxic drug action. Biochem. Pharmacol., 42:1859-1867, 1991.
10. Schmitt, E., Sane, A., and Bertrand, R. Activation and role of caspases in chemotherapy-induced apoptosis. Drug Resistance Updates. 2:21-29, 1999.
11. Eguchi, Y., Shimizu, S., and Tsujimoto, Y. Intracellular ATP levels determine cell death fate by apoptosis or necrosis. Cancer Res. 57: 1835-40, 1997.
12. Leist, M., Single, B., Castoldi, A. F., Kuhnle, S., and Nicotera, P. Intracellular adenosine triphosphate (ATP) concentration: a switch in the decision between apoptosis and necrosis. J. Exp. Med. 185:1481-6, 1997.
13. Schimizu, S., Eguchi, Y., Kamiike, W., Waguri, S., Uchiyama, Y., Matsuda, H., and Tsujimoto, Y. Bcl-2 blocks loss of mitochondrial membrane potential while ICE inhibitors act at a different step during inhibition of death induced by respiratory chain inhibitors. Oncogene 13:21-9, 1996.
14. Nicotera, P. and Leist, M. Energy supply and the shape of death in neurons and lymphoid cells, Cell Death Differ. 4: 435-442, 1997.
15. Nicotera, P. and Leist, M. Mitochondrial signals and energy requirement in cell death. Cell Death Differ. 4:516, 1997.
16. Mehmet, H., Yue, X., Penrice, J., Cady, E., Wyatt, J. C., Sarraf, C., Squirer, M., and Edwards, A. D. Relation of impaired energy metabolism to apoptosis and necrosis following transient cerebral hypoxia-ischaemia. Cell Death Differ. 5: 321-9, 1998.
17. Huschtscha, L., Andersson, C., Bartier, W., and Tattersall, M. Anti-cancer drugs and apoptosis. In: M Lavin and D. Watters (eds.), Programmed Cell Death, The Cellular and Molecular Biology of Apoptosis, pp. 269-279., Harwood Academic Publishers, (GmbH, Poststrasse 22, 700 Chur, Switzerland., 1993.
18. Martin, D. S., Bertino, J. R., and Koutcher, J. A. Perspective: ATP depletion+pyrimidine depletion can markedly enhance cancer therapy—Fresh insight for a new approach. Cancer Res. 60: 6776-6783, Dec. 15, 2000.
19. Kuida, K., Haydar, T. F., Kian, C. Y., Gu, Y., Taya, C., Karasuyama, H., Su, M. S., Rakic, P., and Flavell, R. A. Reduced apoptosis and cytochrome c-mediated caspase activation in mice lacking caspase 9, cell. 94:325-37, 1998.
20. Yoshida, H., Kong, Y. Y., Yoshida, R., Elia, A. J., Hakem, R., Penniger, J. M., and Mak, T. W. Apaf-1 is required for mitochondrial pathways of apoptosis and brain development. Cell, 94:739-750, 1998.
21. Roy, N. Dverauz, Q. L., Takahashi, r., Salvesen, G. S., and Reed, J. C. The c-IAP-1 and c-IAP-2 proteins are direct inhibitors of specific caspases. EMBO J., 16:6914-6925, 1997
22. Droin, N., Beauchemin, M., Solary, E. and Bertrand, R. Identification of a caspase-2 isoform that behaves as endogenous inhibitor of the caspase cascade. Cancer Res. 60:7039-7047, 2000.
23. Sane, A. T., and Bertrand, R. Caspase inhibition in camptothecin-treated U-937 cells is completed with a shift from apoptosis to transient $G_1$, arrest followed by necrotic cell death. Cancer Res., 59: 3565-3569, 1999.
24. Lemaire, C., Andreau, K., Souvannavong, K., and Adam, A. Inhibition of caspase activity induces a switch from apoptosis to necrosis. FEBS Lett, 425:266-270, 1998.
25. Hirsch, T., Marchetti, P., Susin, S. A., Dallaporta, B., Zamzami, N., Marzo, I., Geuskens, M., and Kroemer, G. The apoptosis-necrosis paradox. Apoptogenic proteases activated after mitochondrial permeability transition determine the mode of cell death. Oncogene. 15: 1573-81, 1997.
26. Green, D. R. and Reed, J. C. Mitochondria and apoptosis. Science. 281:1309-12, 1998.
27. Sweet, S. and Singh, G. Accumulation of human promyelocytic leukemic (HL-60) cells at two energetic cell cycle checkpoints. Cancer Res. 55:5164-5167, 1995.
28. Nieminen, A. L., Saylor, A. K., Herman, B., and Lemarsters, J. J. ATP depletion rather than mitochondrial depolarization mediates hepatocyte killing after metabolic inhibition. A J. Physiol. 267: C67-74, 1994.
29. Nguyen, B. T., El Sayed, Y. M., and Sadee, W. Interaction among the distinct effects of adenine and guanine depletion in mouse lymphoma cells. Cancer Res. 44:2272-2277, 1984.
30. Shantz, H. F., Smith, C. M. Fontenella, L. J., Lau, H. K. F., and Henderson, J. F. Inhibition of purine nucleotide metabolism by 6-methylmercaptopurine ribonucleoside and structurally related compounds. Cancer Res., 33:2867-2871, 1972.
31. Warnick, C. T., and Patterson, A. R. P. Effect of methylthioinosine on nucleoside concentration in L5158 cells. Cancer Res., 33:1711-1715, 1973.

32. Street, J. C. Mahmood, U., Ballon, D., Alfieri, A. A., and Koutcher, J. A. 13C and 31P NMR investigation of effect of 6-aminonicotinamide on metabolism of RIF-1 tumor cells in vitro. J. Biol. Chem. 271:4113-9, 1996.
33. Martin, D. S., Stolfi, R. L., Sawyer, R. C., Spiegelman, S., Casper, E. S., and Young, C. W. Therapeutic utility of utilizing low doses of N-(phosphonacetyl)L-aspartic acid in combination with 5-fluorouracil: a murine study with clinical relevance. Cancer Res, 43: 2317-2321, 1983.
34. Grindey, G. B., Lowe, J. K., Divekey, A. Y., and Hakala, M. T. Potentiation by guanine nucleosides of the growth-inhibitory effects of adenosine analogues on L1210 and Sarcoma 180 cells in culture. Cancer Res., 36: 379-383, 1976.
35. King, M. P. and Attardi, G. Human cells lacking mtDNA: repopulation with exogenous mitochondria by complementation. Science. 246: 500-3, 1989.
36. Martin, D. S. Purine and pyrimidine biochemistry, and some relevant clinical and preclinical cancer chemotherapy research. In: G. Powis and R. A. Prough (eds.), Metabolism and Action of Anti-Cancer Drugs, pp 91-140, London: Taylor & Francis, 1987.
37. Martin, D. S. Cancer chemotherapy: past is prologue. Mt. Sinai J. Med., 52: 436-434, 1985.
38. Goldin, A., Kendetti, J. M. MacDonald, J. S., Muggia, F., Henney, J., and Devita, V. T. Current results of the screening program at the Division of Cancer Treatment, National Cancer Institute. Eur. J. Cancer, 17: 129, 1981.
39. Stolfi, R. L., Colofiore, J. R., Nord, L. D., Koutcher, J. A., and Martin, D. S. Biochemical modulation of tumor cell energy: regression of advanced spontaneous murine breast tumors with a 5-fluorouracil containing drug combination. Cancer Res., 52: 4074-4981, 1992.
40. Stolfi, R. L., Colofiore, J. R., Nord, L. D., Martin, D. S. Enhanced antitumor activity of an Adriamycin+5-fluorouracil combination when preceded by biochemical modulation. Anti-Cancer Drugs, 7:100-104, 1996.
41. Martin, D. S., Stolfi, R. L., Colofiore, J. R. and Nord, L. D. Marked enhancement in vivo of paclitaxel's (Taxol's) tumor-regressing activity by ATP-depleting modulation. Anti-Cancer Drugs, 7:655-659, 1996.
42. Martin, D. S., Stolfi, R. L., Colofiore, J. C., Koutcher, J. A., Alfieri, A., Sternberg, S., and Nord, L. D. Apoptosis resulting from anti-cancer agent activity in vivo is enhanced by biochemical modulation of tumor cell energy. In: M. Lavin and D. Walters (eds.), Programmed Cell Death. The Cellular and Molecular Biology of Apoptosis, pp 279-296. New York: Harwood Academic, 1993.
43. Koutcher, J. A., Alfieri, A., Stolfi, R. L., Devitt, M. L., Colofiore, J. R., Nord., L. D., and Martin, D. S. Potentiation of a three drug chemotherapy regimen by radiation. Cancer Res. 53: 3518-3823, 1993.
44. Kamatami, N., Nelson-Rees, W. A., and Carson, D. A. Selective killing of human malignant cell lines deficient in methylthioadenosine phosphorylase, a purine metabolic enzyme. Proc Natl. Acad. Sci. USA 78 (2):1219-1223, 1981.
45. Nobori, T., Szinai, I., Amoz, D., Parker, B. I, Olopade, O. I., Buchagen, D. L., and Carson, D. A. Methylthioadenosine phosphorylase deficiency in non-small cell lung cancers. Cancer Res. 53:1098-1101, 1993.
46. Batova, A., Diccianni, M. B., Omura-Minimisaswa, M., Yu, J., Carrera, C. J., Bridteman, L. J., Kung, F. H., Pullen, J., Amylon, M. D., and Yu, A. L. Use of Alanosine as a methylthioadenosine-selective therapy for T-cell acute lymphoblastic leukemia in vitro. Cancer Res. 59:1492-1497, 1999.
47. Taylor, S. G., Korman, S., Sky-Peck, H. H., and Perlia, D. 6-Aminonicotinamide in disseminated human cancer. Lab. Clin. Med., p. 950, 1958.
48. Herter, G., Weissman, S. G, Thompson, H. G., Hyman, G., and Martin, D. S. Clinical experience with 6-aminonicotinamide. Cancer Res. 21:31-37, 1961.
49. Perlia, C. P., Kofman, S., Sky-Peck, H., and Taylor, S. Clinical use of 6-aminonicotinamide in patients with disseminated neoplastic disease. Cancer, 14: 644-648, 1961.
50. O'Dwyer, P. J., Hudas, G. R., Colofiore, J., Walczak, J., Hoffman, J., LaCreta, F. P., Comis, R. L., Martin, D. S., and Ozols, R. F. Phase I trial of fluorouracil modulation by N-phosphonacetyl-L-aspartate and 6-methylmercaptopurine riboside: optimization of 6-methylmercaptopurine dose and schedule through biochemical analysis of sequential tumor biopsy specimens. J. Natl. Cancer Inst. 83:1235-1240, 1991.
51. Sausville, E. A. and Feigal, E. Evolving approaches to cancer drug discovery and development at the National Cancer Institute, USA Ann. Oncol. 10:1287-1291, 1999.
52. Colofiore, J. R., Stolfi, R. L., Nord, L. D., and Martin, D. S. On the relationship of ATP depletion to chemotherapeutically-induced tumor regression. Int. J. Oncol., 7:1401-1404, 1995.
53. Colofiore, J. R., Stolfi, R. L., Nord, L. D., and Martin, D. S. Biochemical modulation of tumor cell energy. IV. Evidence for the contribution of adenosine triphosphate (ATP) depletion to chemotherapeutically-induced tumor regression. Biochem. Pharmacol., 50: 1943-1948, 1995.
54. Bertino, J. R. Editorial. J. Clin. Oncol. 8 (2): 193-195, 1990.

Eighth Series of Experiments

Progress in Formulating the "Best" ATP-Depleting Combination
(i.e., the ATP-depleting combination that, when co-administered with an anticancer agent effective against the target cancer, achieves cell-killing levels of ATP in drug-resistant cancer cells with the least toxicity to white blood cells and nerves.)
1. The initially employed ATP-depleting agents—6methylmercaptopurine riboside (MMPR)+6-aminonicotinamide (6-AN)—were administered in combination with N-(phosphonacetyl)-L-aspartic acid (PALA), and received the acronym: MAP. MAP enhanced anticancer agent activity against drug-resistant cancer cells.
2. Subsequently, MMPR and 6-AN were combined with alanosine (AL), and received the acronym:MAPAL (i.e., MMPR+6-AN+PALA+AL). MAPAL proved a more effective ATP-depleting agent than MAP. However, in in vivo studies in tumor-bearing animals, MAPAL, when co-administered with anticancer agents, evidenced greater anticancer activity than the same anticancer agents with MAP, but with occasional evidence of greater myelotoxicity. MAPAL, nevertheless, is better than MAP.
3. The combination of PALA+AL+MMPR without 6-AN (acronym: PALM), when co-administered with anticancer agents, appears to produce the same or better antitumor activity than MAPAL without this occasional toxicity. MAPAL needs to be compared with PALM under the same conditions.
4. 6-AN inhibits glycolysis (1), a desirable ATP-depleting effect since the vast majority of solid cancers depend on glycolysis as a source of ATP (2). 6-AN acts by inhibiting the oxidative portion of the Pentose Phosphate Pathway (PPP) via inhibition of the second enzyme of the PPP. DHEA (dehydroepiandrosterone) inhibits the first enzymes of the oxidated version of the PPP, and, although inferior as an inhibitor of glycolosis to 6-AN is less toxic than 6-AN. But since the glycolytic production of ATP receives substrate contributions (fructose-6-phosphate and glyceraldehyde-3-phosphate) from the PPP, the oxidative portion of the PPP, DHEA will likely produce the same inhibition of glycolysis when administered in combination with an inhibitor of the non-oxidative portion of the PPP, oxythiamine (OT). Thus, PALM+DHEA+OT; acronym: PALMDOT.

Nevertheless, a greater blockade of the PPP might be accomplished by inhibiting both the first and the second enzymes of the oxidative portion of PPP with DHEA+6-AN administration together with simultaneous inhibition of the non-oxidative portion of the PPP by OT; acronym: MAPAL-DOT. (If MAPALDOT is myelosuppressive, it may be made safe by a co-administration of G-CSF while affecting greater ATP depletion than PALMDOT.) PALMDOT and MAPAL-DOT need comparison.

5. In summary of our progress in formulating the "best" ATP-depleting combination for co-administration with anticancer agents for the circumvention of drug-resistance factors, depending on the specific anticancer agent(s) and the particular target tumor, one of the following ATP-depleting combinations may be "best": MAPAL, or PALM, or PALMDOT, or MAPALDOT.

Further Evaluation of the Differences Between ATP-Depleting Regimens of MAPAL, PALM, PALMDOT and MAPALDOT Tumor Differences—Different tumor types (e.g., breast cancer vs. ovarian cancer vs. pancreatic cancer) may differ materially in the quantitative contribution of ATP they receive from different ATP-producing metabolic pathways (e.g., from glycolysis as compared to de novo purine metabolism). If the major contribution is, for example, from de novo purine synthesis, then it may be best to employ PALM as the ATP-depleting regimen, for PALM has two inhibitors of de novo purine synthesis, AL (alanosine) and MMPR (6-methyl-mercaptopurine riboside), and no antiglycolysis component. However, while there are exceptions, the vast majority of solid cancers depend on glucose through glycolysis as an energy source, and it would be imprudent to neglect this information. Hence, there should be evaluation of MAPAL, which contains not only MMPR and AL, but also has 6-AN, a proven inhibitor of glycolysis via the oxidative portion of the Pentose Phosphate pathway (PPP). But 6-AN may have toxicities that are non-pertinent to the goal of ATP depletion (such as rare neuroparalyis) and, therefore, it may be best to use DHEA, a less toxic inhibitor of the oxidative PPP. DHEA may be inferior to 6-AN as an inhibitor of glycolytic ATP production, but DHEA and 6-AN have not been previously compared in regard to reduction of glycolytic ATP, and the combination of DHEA+an inhibitor for the non-oxidative portion of the PPP, OT (oxythiamine), has not been evaluated (in combination) as regards inhibition of glycolytic ATP production.

Greater understanding of the above potential interrelationships may be obtained by comparative studies on three different cancers (the human breast cancer xenograft resistant to Adriamycin, the NCI/Adr-Res; the cisplatin (DDP)-doxorubicin-resistant human ovarian cancer xenograft, the SKOV-3; and the S2 (TXT), a taxotere (TXT)-resistant human pancreatic cancer xenograft) as follows:

1. Controls
2. Cisplatin (DDP) MTD
3. Doxorubicin (DOX) MTD
4. Taxotere (TXT) MTD
5. MAP
6. MAPAL
7. PALM
8. PALMDOT
9. MAPALDOT
10. DDP half-MTD
11. DOX half-MTD
12. TXT half-MTD
13. MAP+DDP half-MTD; +DOX half-MTD; TXT half-MTD
14. MAPAL+DDP half-MTD; +DOX half-MTD; +TXT half-MTD
15. PALM+DDP half-MTD; DOX half-MTD; +TXT half-MTD
16. PALMDOT+DDP half-MTD; +DOX half-MTD; +TXT half-MTD
17. MAPALDOT+DDP half-MTD; +DOX half-MTD; +TXT half-MTD (The above 27 groups (10 tumor-bearing animals per group) cannot, practically-speaking, be included in a single transplant experiment, but can be judiciously covered in a number of smaller experiments.)

Myelotoxicity Differences—None of the above three anticancer agents alone at half-MTD, nor the various ATP-depleting regimens alone, cause myelosuppression in their tumor-bearing mice, but in combination (as in groups 13-17) occasionally do, including a rare fatality which can be prevented by either pyruvate administration, or omission of 6-AN, as in PALM. The indirect evidence, (myelosuppression only in combination, prevention by omission of 6-AN, or administration of pyruvate) suggests an adverse effect to a metabolic step of the glycolysis pathway in either the progenitor bone marrow cells or the peripheral blood leucocytes (PBL). Therefore, before treatment, and at intervals (24, 48, 72, and 96 hours) after treatment, bone marrow and PBL will be analyzed for changes in various steps of glycolysis and the PPP. An understanding of the changes may make it possible to identify a biomarker in glycolysis that will predict which tumor-bearing animal (i.e., patient) will undergo severe neutropenia and make possible early G-CSF administration for prevention as opposed to treatment by G-CSF. Such a biomarker in PBL might be glucose-6-phosphate dehydrogenase, known to be important for cell growth and in cell death (3-4).

The elaborate analysis of "best" ATP-depleting regimens, and control of PBL toxicity, detailed above is warranted by the importance of the drug resistance problem. Combination chemotherapy has been proven to cure the heterogeneity of a few types of cancer (e.g., testicular cancer), so there is clear evidence that it is possible to cure cancer with chemotherapy. But chemotherapy fails to cure most solid cancers because of drug resistance. Since there is strong scientific evidence in support of the ATP-depleting therapeutic strategy to circumvent drug resistance, the elaborate evaluation as planned above is because a careful application in the clinic of preclinical guidelines should enable clinical validation of the preclinically-proven strategy. Success is important, for the circumvention of drug resistance factors will clear the way for chemotherapeutic cure of many cancers.

REFERENCES

1. Street, J. C., Mahmoud, U., Ballon, D., Alfieri, A. A., and Koutcher, J. A. 13C and 31P NMR investigation of effect of 6-aminnicotinamide on metabolism of RIF-1 tumor cells in vivo. J. Biol. Chem. 271: 4113-9, 1996.
2. Dang, C. V. and Semenza, G. L. Oncogenic alterations of metabolism. Trends Biochem. Sci. 24: 68-92, 1999.
3. Tian, W-N., Braunstein, L. D., Pang, J., Stuhlmeier, K. M., Xi, Q-C., Tian, X., and Stanton, R. C. Importance of Glucose-6-phosphate dehydrogenase activity for cell growth. J. Biol Chem. 273: 10609-10617, 1998.
4. Tiam, W-N., Braunstein, L. D., Apse, K., Pang, J., Rose, M., Tian, X., and Stanton, R. C. Importance of glucose-6-phosphate dehydrogenase activity in cell death. Am. J. Physiol. 276 (Cell Physiol. 45): C1121-C1131, 1999.

Ninth Series of Experiments

An ATP-Depleting Regimen (e.g., MAPAL)+an Anticancer Agent (e.g., Taxotere) Induces Permanent Growth Arrest and a Senescence-Like Phenotype in Advanced Human Breast Cancer Xenografts (MDA-MB-468) that Results in Cure The induction of cell senescence, along with apoptosis, and other types of cell death (e.g., necrosis, mitotic catastrophe), can be a major response of cancer cells to cytotoxic and cytostatic agents. Thus, treatment conversion of cancer cells to senescent permanent proliferation arrest and subsequent cell death can add an important determinant of effective treatment outcome.

Neither the anticancer agent at MTD, nor the anticancer agent at half-MTD alone, nor the ATP-depleting regimen alone, effected senescence in the breast tumor xenografts. Therefore, this identification that only the combination of the ATP-depleting regimen with a moderate dose of anticancer agent can induce or facilitate senescence in tumor cells is an important finding for the improvement of cancer therapy.

Present Status of Cancer Chemotherapy and Drug Resistance

Chemotherapy is the primary treatment once cancer becomes systemic (i.e., metastasizes). Most anticancer agents damage DNA in their target cancer cells, but the post-damage responses of apoptosis, necrosis, mitotic catastrophe and senescence are thwarted in drug-resistant cancer cells. The drug resistance factors are multiple, and range from mechanisms that limit the drug-target interaction (e.g., overexpression of drug efflux pumps, as p-glycoprotein, and intracellular detoxifiers, as glutathione) to genetic disruption of the apoptotic and senescence pathways. Drug-induced senescence, although difficult to induce, is increasingly being considered an important consequence of effective treatment (2,3). Mitotic catastrophe is a form of programmed cell death when the DNA-damaged cells exit a cell cycle arrest and undergo fatal endomitosis (1). It is the contribution of apoptosis to therapy-induced cell death (the "apoptosis concept" that is considered by most as the pivotal response program in drug-treated tumor cells (4). And necrosis, although occasionally listed as a drug-induced response, is usually not considered.

Yet, necrosis is the cell death pathway simultaneously initiated with apoptosis by drug-induced DNA damage that, unlike apoptosis, can be restored to the completion of cell death (5). Necrosis is due to severe ATP depletion (15% of normal and below), a cell-killing level prevented from attainment by drug-resistant factors (5). However, ATP is nevertheless reduced due to the activation of PARP by anticancer agent-induced DNA damage (5). Thus, unlike "mitotic catastrophe" and the cell death mode of apoptosis, which are initiated but not completed in drug-resistant cancer cells, the necrosis pathway in drug-resistant cells is partially completed (5). The anticancer agent-induced DNA damage, even though lessened by drug-resistant factors, reduces ATP and thereby "chemosensitizes" the drug-resistant cancer cell for further reduction to cell-killing ATP levels by the co-administration of an appropriate ATP-depleting regimen (5). It does not matter whether one or multiple drug-resistant factors are involved in the limitation of the necrosis pathway because the treatment to circumvent the drug-resistant factors is aimed at bringing the product of their collective blocking action—i.e., the reduced ATP level—to cell-killing levels. The ability to kill drug-resistant cancer cells by an apoptotic independent mechanism—i.e., necrosis—has been preclinically demonstrated, and is receiving NCI support for validation of the ATP-depleting strategy by clinical trial.

As noted above, there is growing evidence that senescence of cancer cells can be induced following chemotherapy and can contribute to the success of chemotherapy (2,3). It is of great additional interest that the same ATP-depleting strategy that enhances cancer cell death by inducing necrosis, also can induce senescence in cancer cells in vivo. (The latter gratifying results require additional confirmation in other tumor models and with other anticancer agents.)

Chemotherapy has cured a few types of human tumors. However, many human advanced solid cancers respond poorly to chemotherapy because of drug-resistant cells. The ATP-depleting strategy could circumvent the latter problem, and thereby create the opportunity for chemotherapeutic cure of the more common human malignancies. The belief, and general consensus, that chemotherapy kills by apoptosis, and therefore that cells resistant to apoptosis are resistant to drug therapy, neglects the long-established fact that chemotherapy also kills by necrosis (5-7), and overlooks the evidence that cell death by blocked apoptosis can be "switched" to necrosis (7-9). Overcoming drug resistance is the most important obstacle to the success of chemotherapy in the cure of advanced human cancers.

REFERENCES

1. King, K. L. and Cidlowski, J. A. Cell cycle and apoptosis: common pathways to life and death. J. Cell Biochem 58: 175-180, 1995.
2. Berns, A. Senescence: A companion in chemotherapy? Cancer Cell: May, 2002; 309-311.
3. Schmitt, C. A., Fridman, J. S., Yang, M., Lee, S., Baranov, E., Hoffman, R. M., and Lowe, S. W. A senescence program controlled by p53 and p16 ink4a contributed to the outcome of cancer therapy. Cell 109:335-346, 2002.
4. Schmitt, C. A. and Lowe, S. W. Apoptosis and chemoresistance in transgenic cancer models. J. Mol. Med. 80: 137-146, 2002.
5. Martin, D. S., Bertino, J. R., and Koutcher, J. A. ATP depletion+pyrimidine depletion can markedly enhance cancer therapy: Fresh insight for a new approach. Cancer Res. 60: 6776-6783, 2000.
6. Eguchi, Y., Shimizu, S., and Tsujimoto, Y. Intracellular ATP levels determine cell fate by apoptosis or necrosis. Cancer Res. 57: 1835-1840, 1997.
7. Leist, M., Single, B., Castoldo, A. F., Kuknle, S., and Nicotera, P. Intracellular triphosphate (ATP) concentration: a switch in the decision between apoptosis and necrosis. J. Exp. Med. 185: 1481-1486, 1997.
8. Sane, A. T., and Bertrand, R. Caspase inhibition in camptothecin-treated U-937 cells is completed with a shift from apoptosis to transient G1 arrest followed by necrotic cell death. Cancer Res., 59: 3565-3569, 1999.
9. Lemaire, C., Andreau, K., Souvannavong, K., and Adam, A. Inhibition of caspase activity induced a switch from apoptosis to necrosis. FEBS Lett. 425: 266-270, 1998.

What is claimed is:

1. A method of treating a subject having a cancer selected from the group consisting of breast cancer, colon cancer and leukemia, comprising administering to the subject the following combination of agents:
   (i) 6-methylmercaptopurine riboside (MMPR);
   (ii) 6-aminonicotinamide (6-AN), wherein MMPR and 6-AN are administered together in an amount sufficient to reduce the adenosine 5'-triphosphate (ATP) level in the cancer cells to 15% of normal or below 15% of normal; and
   (iii) N-(phosphonacetyl)-L-aspartic acid (PALA);
   wherein said combination of agents is administered concurrently or sequentially with one or more anti-cancer agents and/or an anti-cancer treatment selected from the group consisting of 5-fluorouracil, phenylalanine mustard, doxorubicin, cisplatin, paclitaxel, radiation, cyclophosphoramide, mitomycin, etoposide, and docetaxel.

2. The method of claim 1, wherein the combination of agents and anti-cancer agent is 6-methylmercaptopurine riboside, 6-aminonicotinamide, N-(phosphonacetyl)-L-aspartic acid, and 5-fluorouracil.

3. The method of claim 1, wherein the combination of agents and anti-cancer agent is 6-methylmercaptopurine riboside, 6-aminonicotinamide, N-(phosphonacetyl)-L-aspartic acid, 5-fluorouracil, and doxorubicin.

4. The method of claim 1, wherein the combination of agents and anti-cancer agent is 6-methylmercaptopurine riboside, 6-aminonicotinamide, N-(phosphonacetyl)-L-aspartic acid, and phenylalanine mustard.

5. The method of claim 1 wherein the combination of agents 6-methylmercaptopurine riboside, 6-aminonucotinamide, and N-(phosphonacetyl)-L-aspatic acid further comprises the agent alanosine and an anti-cancer agent selected from the group consisting of docetaxel and doxorubicin.

6. The method of claim 5, wherein the minimum effective dosage of docetaxel is less than the therapeutically effective dosage when docetaxel is administered as the sole anti-cancer agent.

7. A method of treating a subject having a cancer selected from the group consisting of breast cancer, colon cancer and leukemia, comprising administering to the subject the following combination of agents:
   6-methylmercaptopurine riboside (MMPR),
   N-(phosphonacetyl)-L-aspartic acid (PALA), and
   alanosine (AL).

8. The method of claim 7, wherein the selected dosages of the combination of agents is sufficient to reduce the level of adenosine 5'-triphosphate in said cancer cells to 15% of normal or below 15% of normal.

* * * * *